(12) United States Patent
Brophy et al.

(10) Patent No.: US 7,381,699 B2
(45) Date of Patent: Jun. 3, 2008

(54) REAGENTS AND METHODS FOR SMOOTH MUSCLE THERAPIES

(75) Inventors: Colleen Brophy, Scottsdale, AZ (US); Padmini Komalavilas, Tempe, AZ (US); Alyssa Panitch, Higley, AZ (US); Brandon Seal, Mesa, AZ (US); Lokesh Joshi, Tempe, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 195 days.

(21) Appl. No.: 11/078,256

(22) Filed: Mar. 11, 2005

(65) Prior Publication Data

US 2006/0035814 A1 Feb. 16, 2006

Related U.S. Application Data

(62) Division of application No. 10/226,956, filed on Aug. 23, 2002, now Pat. No. 7,135,453.

(60) Provisional application No. 60/314,535, filed on Aug. 23, 2001.

(51) Int. Cl.
*A61K 38/10* (2006.01)
*A61K 38/16* (2006.01)

(52) U.S. Cl. ............................. 514/2; 514/12; 530/324

(58) Field of Classification Search ...................... None
See application file for complete search history.

(56) References Cited

U.S. PATENT DOCUMENTS

| 5,710,172 | A | | 1/1998 | Kukreja et al. |
| 5,985,635 | A | * | 11/1999 | Bandman et al. ........... 435/194 |
| 6,475,490 | B1 | | 11/2002 | Srivastava et al. |
| 2004/0192592 | A1 | | 9/2004 | Weiner et al. |

FOREIGN PATENT DOCUMENTS

| JP | 2001-278894 | * | 10/2001 |
| WO | WO 91/15219 | | 10/1991 |
| WO | WO 98/53061 | | 11/1998 |

OTHER PUBLICATIONS

Beall et al. The Smaall Heat Shcok Related Proteins, HSP20, is Phosphorylated on Serine 16 During Cyclic Nucleotide-Dependent Relaxation, J. of Biol. Chem. vol. 274, No. 16, pp. 11344-11351. 1999.*
Kato et al. "Purification and characterization of a 20-kDa protein that is highly homologous to aB crystallin," J. of Biol. Chem. vol. 269 No. 21, pp. 15302-15309. 1994.*
David Arthur Woodrum, (May 1999), Dissertation submitted to the Faculty of the School of Graduate Studies of the Medical College of Georgia in partial fulfillment of the Requirements of the Degree of Doctor of Philosophy, "The Role of the Small Heat Shock Proteins, HSP20 and HSP27, In Clyclic Nucleotide-Dependent Vasorelaxation".

Additions and Corrections, (1999), The Journal of Biological Chemistry, vol. 274 (39), p. 28058.
Brophy et al., 2002, J. Vasc. Res., "cGMP-Dependent Protein Kinase Expression Restores Contractile Function in Cultured Vascular Smooth Muscle Cells", vol. 39, pp. 95-103.
Rembold et al., 2001, BMC Physiology, "Localization of heat shock protein 20 in swine carotid artery", 1:10.
Mai, et al., (2002), The Journal of Biological Chemistry, "Efficiency of Protein Transduction is Cell Type-Dependent and Is enhanced by Dextran Sulfate", vol. 277 (33), pp. 30208-30218.
Beall, et al., (1999), Additions and Corrections to The Journal of Biological Chemistry, "The small heat shock-related protein, HSP20, is phosphorylated on serine 16 during cyclic nucleotide-dependent relaxation", vol. 274, (16), pp. 11344-11351. p. 28058.
Francy, et al., (1998), Eur. J. Biochem., "The mammalian small heat-shock protein Hsp20 forms dimmers and is a poor chaperone", vol. 258(3), pp. 1014-1021.
Brophy, et al., (2000), Am. J. Physiol. Heart Circ. Physiol., "Functional Expression of NOS 1 in Vascular Smooth Muscle", vol. 278, pp. H991-H997.
Akamatsu, et al., (1997), Bioorg Med Chem, "Potent Inhibition of Protein-Tyrosine Phosphatase by Phosphotyrosine-Mimic Containing Cyclic Peptides", vol. 5 (1), pp. 157-163.
Anderson, P., et al., (2000), Arterioscler Thromb Vasc Biol, Cyclic GMP-dependen protein kinase expression in coronary arterial smooth muscle in response to balloon catheter injury. , vol. 20, pp. 2191-2197.
Beall, A., et al., (1997), The Journal of Biological Chemistry, "Cyclic Nucleotide-dependent Vasorelaxation Is Associated with the Phosphorylation of a Small Heat Shock-related Protein", vol. 272, (17), pp. 11283-11287.
Beall, A., et al., (1999), The Journal of Biological Chemistry, "The small heat shock-related protein, HSP20, is phosphorylated on serine 16 during cyclic nucleotide-dependent relaxation", vol. 274, (16), pp. 11344-11351.
Bergh, C., et al., (1995), The American Physiological Society, "Impaired Cyclic Nucleotide-dependent Vasorelaxation in Human Umbilical Artery Smooth Muscle", vol. 268, pp. H202-H212.
Boerth, N., et al., (1997), J. Vasc. Res., Cyclic GMP-deendent protein kinase regulates vascular smooth muscle cell phenotype., vol. 34, p. 245-259.
Brophy, C., et al., (1999), The Journal of Biological Chemistry, "Phosphorylation of the Small Heat Shock-related Protein, HSP20, in Vascular Smooth Muscles is Associated with Changes in the Macromolecular Associations of HSP20", vol. 274, (10), pp. 6324-6329.

(Continued)

*Primary Examiner*—Anish Gupta
(74) *Attorney, Agent, or Firm*—McDonnell Boehnen Hulbert & Berghoff LLP; David S. Harper

(57) ABSTRACT

The present invention provides novel polypeptides comprising heat shock protein 20(HSP20)-derived polypeptides to treat or inhibit smooth muscle vasospasm, as well to treat and inhibit smooth muscle cell proliferation and migration.

33 Claims, 10 Drawing Sheets

OTHER PUBLICATIONS

Brophy, C., et al., (1998), Journal of reproduction and Fertility, "Heat shock protein expression in umbilical artery smooth muscle", vol. 114, pp. 351-355.
Brophy, C. et al., (1997), Biology of Reproduction, "Small Heat Shock Proteins and Vasospasm in Human Umbilical Artery Smooth Muscle", vol. 57, pp. 1354-1359.
Brophy, C., et al., (1997), The Basic Science of Vascular Disease, "Regulation of Vasomotor Tone and Vasospasm", Chapter 13, pp. 367-384.
Brophy, C., et al., (1997), Journal of Vascular Surgery, "Cellular mechanisms of cyclic nucleotide-induced vasorelaxation", vol. 25, (2), pp. 390-397.
Brophy, C., et al., (1999), Journal of Vascular Surgery, "The small heat shock-related protein-20 is an actin-associated protein", vol. 29(2), pp. 326-333.
Brophy, C., et al., (2000), Surgery, "The macromolecular associations of heat shock protein-27 in vascular smooth muscle", vol. 128 (2), pp. 320-326.
Brophy,C., (2000), Journal of Vascular Surgery, Invited Basic Science Review, "The dynamic regulation of blood vessel caliber", vol. 31 (2), pp. 391-396.
Brophy, C., et al., (2001), Journal of Vascular Research, Internet Discussion Forum, "cGMP-Dependent Protein Kinase Expression Restores Contractile Function in Cultured Vascular Smooth Muscle Cells", vol. 39, pp. 95-103.
Brophy, C., (2002), World J. Surg, "Stress and Vascular Disease at the Cellular and Molecular Levels", vol. 26, pp. 779-782.
Carpino and Han, (1972), J. Org. Chem., "The 9-Fluorencylmethoxycarbonyl Amino-Protecting Group", vol. 37, pp. 3403-3409.
Fawell, S., et al., (1994), Proc Natl Acad Sci USA, "Tat-mediated delivery of heterologous proteins into cells", vol. 91, pp. 664-668.
Francy, A., et al., (1999), Biochemical and Biophysical Research Communications, "Rat Hsp20 Confers Thermoresistance in a Clonal Survival Assay, but Fails to Protect Coexpressed Luciferase in Chinese Hamster Ovary Cells", vol. 254, pp. 164-168.
Frankel, A., et al., (1988), Cell, "Cellular uptake of the tat protein from human immunodeficiency cirus", vol. 55, 1189-1193.
Fuchs, L., et al., (2000), Am J. Physiol Regulatory Integrative Comp Physiol, "Stress cases decrease in vascular relaxation linked with altered phosphorylation of heat shock proteins", vol. 279, pp. R492-R498.
Green, M., et al., (1988), Cell, "Autonomous Functional Domains of Chemically Synthesized Human Immunodeficiency Virus Tat Trans-Activator Protein", vol. 55, pp. 1179-1188.
Hedges, J., et al., (1999), The Journal of Biological Chemistry, "A Role for p38$^{MAPK}$/HSP27 Pathway in Smooth Muscle Cell Migration", vol. 274, (34), pp. 24211-24219.
Ho, A., et al., (2001), Cancer Res., "Synthetic protein transduction domains: enhanced transduction potential in vitro and in vivo", vol. 61, pp. 474-477.
Inaguma, Y., et al., (1996), Gene, "cDNA cloning of a 20-kDa protein (p20) highly homologous to small heat shock proteins: developmental and physiological changes in rat hindlimb muscles", vol. 178, pp. 145-150.
Jerius, H., et al., (1999), J. Vasc. Surg, Endothelial-dependent vasodilation is associated with increases in the phosphorylation of a small heat shock protein (HSP20), vol. 29, pp. 678-684.
Kato, K., et al., (1994), The Journal of Biological Chemistry, Purification and Characterization of a 20-kDa Protein that is Highly Homologous to Crystallin, vol. 269, (21), pp. 15302-15309.
Knoepp, et al., (1999), Surgical Forum, "Cellular stress inhibits smooth muscle relaxation", *Surgical forum*, vol. 50, pp. 432-433.
Knoepp, et al., (1999), J. Vasc. Surg., "Cellular stress inhibits vascular smooth muscle relaxation", vol. 31, pp. 343-353.
Komalavilas, P., et al., (2001), J. Appl. Physiol, "PI3-kinase/Akt modulates vascular smooth muscle tone via camp signaling pathways", vol. 91, pp. 1819-1827.
Lavoie, J. et al., (1995), Molecular and Cellular Biology, "Modulation of Cellular Thermoresistance and Actin Filament Stability Accompanies Phosphorylation-Induced Changes in the Oligomeric Structure of Heat Shock Protein 27", vol. 15 (1), pp. 505-516.
Macomson, et. al., (2002), Neurosurgery, "Heat shock protein expression in cerebral vessels after subarachnoid hemorrhage", vol. 51, pp. 204-211.
Matsuno, H., et al., (1998), FEBS Letters, "A heat shock-related protein, p20, plays and inhibitory role in platelet activation", vol. 429, pp. 327-329.
Merrifield, R.B., (1963), J. Am. Chem. Soc., "Solid Phase Peptide Synthesis. I. The Syntheseis of a Tetrapeptide", vol. 85, pp. 2149-2154.
Niwa, M., et al., (2000), Elsevier Life Sciences, "Small Molecular Weight Heat Shock-related Protein, HSP20, Exhibits and Anti-Platelet Activity by Inhibiting Receptor-Mediated Calcium Influx", vol. 66 (1), pp. PL7-PL12.
O'Connor, M., et al., (2002), J. Appl. Physiol., "Heat-induced force suppression and HSP20 Phosphorylation in Swine carotid media", vol. 93, pp. 484-488.
Otaka, A., et al., (1995), Pergamon, Tetrahedron Letters, Elsevier Science Ltd., "Synthesis and Application of N-Boc-L-2-amino-4(diethylphosphono)-4,4-difluorobutanoic acid for Solid-Phase Synthesis of Nonhydrolyzable Phosphoserine Peptide Analogues", vol. 36, (6), pp. 927-930.
Rembold, C., et al., (2001), BMC Physiology, "Localization of heat shock protein 20 in swine carotid artery", vol. 1(10).
Rembold, C., et al., (2000), Elsevier Biochimica et Biophysica Acta, "Caldesmon and heat shock protein 20 phosphorylation in nitroglycerin and magnesium-induced relaxation of swine carotid artery", vol. 1500, pp. 257-264.
Rembold, C., et al., (2000), Journal of Physiology, "cGMP-mediated phosphorylation of hat shock protein 20 may cause smooth muscle relaxation without mysin light chain dephosphorylation in swine carotid artery", vol. 524 (3), pp. 865-878.
Rembold, C., et al., (2001), J. Appl. Physiol., "Signal Transduction in Smooth Muscle Selected Contribution: HSP20 phosphorylationin nitroglycerin-and forskolin-induced sustained reductions in swine carotid media tone", vol. 91, pp. 1460-1466.
Rembold, C., et al., (2001), BMC Physiology, "Localization of heat shock protein 20 in swine carotid artery", vol. 1, pp. 1-7.
Rembold, C., et al., (2002), J. Appl Physiol, "Letters to the Editor", vol. 92, pp. 890-891.
Schwarze, S., et al., (1999), Science, "In vivo protein transduction: delivery of a biologically active protein into the mouse.", vol. 285, pp. 1569-1572.
Tyagi, M., et al., (2001), J. Biol. Chem., "Internalization of HIV-1 tat requires cell surface heparan sulfate proteoglycans", vol. 276, pp. 3254-3261.
Wadia, J., et al., (2002), Curr Opin Biotechnol, "Protein transduction technology", vol. 13, pp. 52-56.
Wang, Y., et al., (1999), FEBS Letters, "Amylin evokes phosphorylation of P20 in rat skeletal muscle", vol. 457, pp. 149-152.
Wang, Y., et al., (1999), FEBS Letters, "Insulin and insulin antagonists evoke phosphorylation of P20 at serine 157 and serine 16 respectively in rat skeletal muscle", vol. 462, pp. 25-30.
Wang, Y., et al., (1999), Biochem. J., "Phosphorylation of P20 is associated with the actions on insulin in rat skeletal and smooth muscle", vol. 344, pp. 971-976.
Woodrum, D., et al., (1999), Am. J. Physiol., "Phosphorylation events associated with cyclic nucleotide-dependent inhibition of smooth muscle contraction", pp. H931-H939.
Woodrum, D., et al., (2001), Elsevier, Molecular and cellular Endocrinology, "The paradox of smooth muscle physiology", vol. 177, pp. 135-143.
Yamboliev, I., et al., (2000), Am. J. Physiol. Heart Circ. Physiol., "Evidence for Mosulation of Smooth Muscle Force by the p38 MAP kinase/HSP27 Pathway", vol. 278, pp. H1899-H1907.

* cited by examiner

REAGENTS AND METHODS FOR SMOOTH MUSCLE THERAPIES

CROSS REFERENCE

This application is a divisional of U.S. patent application Ser. No. 10/226~956 filed Aug. 23, 2002, which, now U.S. Pat. No. 7,135,453 claims priority from U.S. Provisional Patent Application Ser. No. 60/314,535 filed Aug. 23, 2001, the disclosure of which is incorporated by reference herein in its entirety.

STATEMENT OF GOVERNMENT FUNDING

The U.S. Government through the National Institute of Health, provided financial assistance for this project under Grant No. RO1 HL58027-06. Therefore, the United States Government may own certain rights to this invention.

FIELD OF INVENTION

This invention relates generally to the fields of cell biology, molecular biology, pharmaceuticals, and smooth muscle biology.

BACKGROUND

There are three types of muscles: cardiac, skeletal, and smooth. Smooth muscles are found in the walls of blood vessels, airways, the gastrointestinal tract, and the genitourinary tract. The caliber of tubes lined by these muscles is dependent on a dynamic balance between the state of contraction and the state of relaxation of the muscles in these organs. Contraction and relaxation of smooth muscles are mediated by different signaling pathways inside the muscles. Pathways which induce relaxation also inhibit contraction. Sustained contraction of muscle is a "spasm" of the muscle. This spasm can be prevented by activating pathways or systems which induce relaxation, or in other words, inhibit contraction.

For the most part, smooth muscles are unique in that they lack the ordered structure of cardiac and skeletal muscles and that they are able to maintain tonic contractions with minimal oxygen use. Pathologic tonic contraction is a state in which the muscles are in spasm.

Many pathological conditions are associated with spasm of vascular smooth muscle ("vasospasm"), the smooth muscle that lines blood vessels. Vasospasm, of the vessel causes narrowing of the vessel lumen, limiting blood flow. Spasm of any vessel leads to ischemia to the organ that the vessel supplies blood to. Ischemia is reversible lack of blood flow and oxygen supply to the tissues. In the case of spasm of the vessels in the heart it leads to cardiac ischemia and/or infarction; spasm of vessels in the brain leads to stroke; spasm of the vessels that supply the intestines leads to mesenteric ischemia, a lack of relaxation of the vessels in the penis leads to impotence, since erection requires vasodilation of the corpra cavernosal (penile) blood vessels; and spasm of the intracranial blood vessels leads to migraines.

Excessive vasoconstriction (or inadequate vasodilation) occur in other disease states as well. Hypertension (high blood pressure) is caused by excessive vasoconstriction, as well as thickening, of the vessel wall, particularly in the smaller vessels of the circulation. This process may affect the lung vessels as well and cause pulmonary (lung) hypertension and asthma (bronchospasm). Other disorders known to be associated with excessive constriction, or inadequate dilation of smooth muscles include toxemia of pregnancy, pre-term labor, pre-eclampsia/eclampsia, Raynaud's disease or phenomenon, anal fissure, achalasia, hemolytic-uremia, and Prinzmetal's angina, a form of coronary spasm that causes angina. Spasm in the coronary arteries also occurs during mechanical manipulation of coronary arteries, such as during angioplasty and stenting. This spasm can lead to ischemia and infarction.

Surgical procedures involving the vasculature are also complicated by vasospasm of smooth muscle, which may result in both short term and long term complications including restenosis and vascular occlusion. There is a general pattern in which vasospasm, if persistent, leads to constrictive remodeling/intimal hyperplasia, and ultimately vascular occlusion. Corrective surgical procedures, such as stenting of a blood vessel, angioplasty, and implanting prosthetic devices such as dialysis access fistulas and shunts, are accompanied by damage to the smooth muscle. This leads to smooth muscle cell proliferation and migration. This ultimately leads to constrictive remodeling and intimal hyperplasia. This process leads to restenosis, prosthetic graft failure, stent and stent graft failure, microvascular graft failure, atherosclerosis, and transplant vasculopathy.

While incompletely understood, intimal hyperplasia is mediated by a sequence of events that include endothelial cell injury and vascular smooth muscle proliferation and migration from the media to the intima. This is associated with a phenotypic modulation of the smooth muscle cells from a contractile to a synthetic phenotype. The "synthetic" smooth muscle cells secrete extracellular matrix proteins, which leads to pathologic vascular occlusion, as described above. Furthermore, increased proliferation and migration of smooth muscle cells can also lead to smooth muscle cell tumors, such as leiomyosarcomas and leiomyomas.

Thus, it would be of great benefit to identify new methods and therapeutics to treat or inhibit smooth muscle vasospasm, promote smooth muscle relaxation, improve other therapies involving smooth muscle, and to treat and inhibit smooth muscle cell proliferation and migration.

SUMMARY OF THE INVENTION

The present invention provides new methods and therapeutics to treat or inhibit smooth muscle vasospasm, promote smooth muscle relaxation, improve other therapies involving smooth muscle, and to treat and inhibit smooth muscle cell proliferation and migration.

In one aspect, the present invention provides polypeptides consisting of an amino acid sequence according to general formula I:

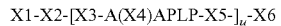

X1-X2-[X3-A(X4)APLP-X5-]$_u$-X6 wherein X1 is absent or is one or more molecules comprising one or more aromatic ring;

X2 is absent or comprises a transduction domain;

X3 is 0, 1, 2, 3, or 4 amino acids of the sequence WLRR (SEQ ID NO:1);

X4 is selected from the group consisting of S, T, Y, D, E, hydroxylysine, hydroxyproline, phosphoserine analogs and phosphotyrosine analogs;

X5 is 0, 1, 2, or 3 amino acids of a sequence of genus Z1-Z2-Z3, wherein Z1 is selected from the group consisting of G and D;

Z2 is selected from the group consisting of L and K; and

Z3 is selected from the group consisting of S and T;

X6 is absent or comprises a transduction domain; and wherein u is 1-5.

In a preferred embodiment, X4 is phosphorylated. In a further preferred embodiment, at least one of X2 and X6 comprises a transduction domain.

In another aspect, the invention provides polypeptides consisting of an amino acid sequence according to the general formula II:

X1-X2-[X3-A(X4)APLP-X5]$_n$-X6 wherein X1 is absent or is one or more molecules comprising one or more aromatic ring;

X2 is absent or comprises a cell transduction domain;

X3 is 0-14 amino acids of the sequence of heat shock protein 20 between residues 1 and 14 of SEQ ID NO:297;

X4 is selected from the group consisting of S, T, Y, D, E, hydroxylysine, hydroxyproline, phosphoserine analogs and phosphotyrosine analogs;

X5 is 0-140 amino acids of heat shock protein 20 between residues 21 and 160 of SEQ ID NO:297;

X6 is absent or comprises a cell transduction domain; and wherein at least one of X2 and X6 comprise a transduction domain.

In a preferred embodiment, X4 is phosphorylated.

In another aspect, the present invention provides pharmaceutical compositions, comprising one or more polypeptides of the present invention and a pharmaceutically acceptable carrier.

In another aspect, the present invention provides isolated nucleic acid sequences encoding a polypeptide of the present invention. In further aspects, the present invention provides recombinant expression vectors comprising the nucleic acid sequences of the present invention, and host cells transfected with the recombinant expression vectors of the present invention.

In another aspect, the invention provides improved biomedical devices, wherein the biomedical devices comprise one or more polypeptides of the present invention disposed on or in the biomedical device. In various embodiments, such biomedical devices include stents, grafts, shunts, stent grafts, angioplasty devices, balloon catheters, fistulas, and any implantable drug delivery device.

In another aspect, the invention provides methods for inhibiting smooth muscle cell proliferation and/or migration, comprising contacting the smooth muscle cells with an amount effective to inhibit smooth muscle cell proliferation and/or migration of one or more polypeptide of the present invention. In various preferred embodiments of this aspect of the invention, the method is used to treat or prevent a disorder selected from the group consisting of intimal hyperplasia, stenosis, restenosis, and atherosclerosis. In various other preferred embodiments of this aspect of the invention, the method is performed on a subject who has undergone, is undergoing, or will undergo a procedure selected from the group consisting of angioplasty, vascular stent placement, endarterectomy, atherectomy, bypass surgery, vascular grafting, organ transplant, prosthetic implant, microvascular reconstructions, plastic surgical flap reconstruction, and catheter emplacement. In a further embodiment of this aspect of the invention, the method is used to treat smooth muscle cell tumors.

In a further aspect, the present invention comprises methods for treating or inhibiting a disorder selected from the group consisting of intimal hyperplasia, stenosis, restenosis, and/or atherosclerosis, comprising contacting a subject in need thereof with an amount effective to treat or inhibit intimal hyperplasia, stenosis, restenosis, and/or atherosclerosis of HSP20, or a functional equivalent thereof.

In a further aspect, the present invention comprises methods for treating smooth muscle cell tumors comprising contacting a subject in need thereof with an amount effective to treat smooth muscle tumors of HSP20, or a functional equivalent thereof.

In a further aspect, the present invention provides a method for treating or preventing smooth muscle spasm, comprising contacting a subject in need thereof with an amount effective to inhibit smooth muscle spasm of one or more polypeptides of the present invention. In various preferred embodiments of this aspect of the invention, the muscle cell spasm is associated with a disorder or condition selected from the group consisting of angina, Prinzmetal's angina (coronary vasospasm), ischemia, stroke, bradycardia, hypertension, pulmonary (lung) hypertension, asthma (bronchospasm), toxemia of pregnancy, pre-term labor, pre-eclampsia/eclampsia, Raynaud's disease or phenomenon, hemolytic-uremia, non-occlusive mesenteric ischemia, anal fissure, achalasia, impotence, migraine, ischemic muscle injury associated with smooth muscle spasm, and vasculopathy, such as transplant vasculopathy.

In a further aspect, the present invention provides methods for promoting smooth muscle relaxation, comprising contacting smooth muscle with an amount effect effective to promote smooth muscle relaxation with one or more of the polypeptide of the present invention.

DETAILED DESCRIPTION OF THE INVENTION

Figure 1:
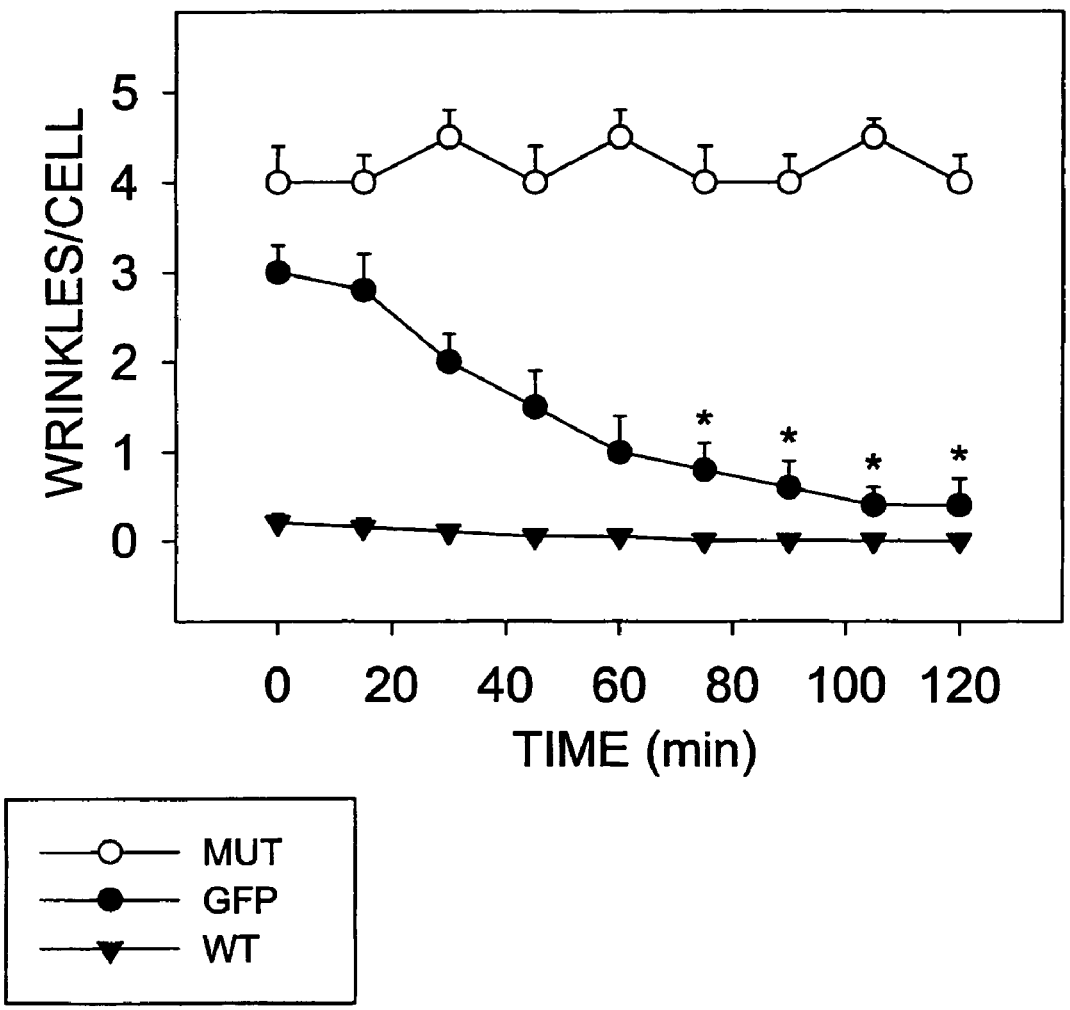
FIG. 1. Mesangial cells were transfected with vectors containing green fluorescent protein (GFP) alone, GFP fused to the 5' end of the wild type cDNA for HSP20 (WT), or GFP fused to an HSP20 construct in which the PKA phosphorylation site was mutated to an alanine (S16A-HSP20)(MUT) and the number of wrinkles under the cells was determined after treatment with dibutyryl cAMP (10 ΦM) for 0 minutes, 30 minutes, 60 minutes, or 90 minutes.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), and *Gene Transfer and Expression Protocols*, pp. 109-128, ed. E. J. Murray, The Humana Press Inc., Clifton, N.J.)

In one aspect, the present invention provides polypeptides consisting of an amino acid sequence according to general formula I:

$$X1\text{-}X2\text{-}[X3\text{-}A(X4)APLP\text{-}X5\text{-}]_u\text{-}X6$$

wherein X1 is absent or is one or more molecules comprising one or more aromatic ring;

X2 is absent or comprises a transduction domain;

X3 is 0, 1, 2, 3, or 4 amino acids of the sequence WLRR (SEQ ID NO:1);

X4 is selected from the group consisting of S, T, Y, D, E, hydroxylysine, hydroxyproline, phosphoserine analogs and phosphotyrosine analogs;

X5 is 0, 1, 2, or 3 amino acids of a sequence of genus Z1-Z2-Z3, wherein Z1 is selected from the group consisting of G and D;

Z2 is selected from the group consisting of L and K; and

Z3 is selected from the group consisting of S and T;

X6 is absent or comprises a transduction domain; and wherein u is 1-5.

Both single letter and three letter amino acid abbreviations are used within the application. As used herein, "norL" means norleucine and "Orn" means ornithine.

The term "polypeptide" is used in its broadest sense to refer to a sequence of subunit amino acids, amino acid analogs, or peptidomimetics. The subunits are linked by peptide bonds, except where noted (including when the X2 position is a non-amino acid molecule that contains an aromatic ring). The polypeptides described herein may be chemically synthesized or recombinantly expressed.

Preferably, the polypeptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile Nα-amino protected 9-fluorenylmethoxycarbonyl (Fmoc) amino acids first described by Carpino and Han (1972, J. Org. Chem. 37:3403-3409). Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers. The polypeptides of the invention may comprise D-amino acids (which are resistant to L-amino acid-specific proteases in vivo), a combination of D-and L-amino acids, and various "designer" amino acids (e.g., β-methyl amino acids, Cα-methyl amino acids, and Nα-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

According to various embodiments of the polypeptides of general formula I, the region $[X3-A(X4)APLP-X5-]_u$ may be present in 1, 2, 3, 4, or 5 copies. In a preferred embodiment, it is present in 1 copy. In other embodiments, it is present in multiple copies to provide increased efficacy for use of the polypeptides for inhibiting one or more of smooth muscle cell proliferation, smooth muscle cell migration, and smooth muscle spasm, and/or also for promoting smooth muscle vasorelaxation.

According to various embodiments of the polypeptides of general formula I, X4 is S, T, Y, D E, a phosphoserine mimic, or a phosphotyrosine mimic. It is more preferred that X4 is S, T, or Y; more preferred that X4 is S or T, and most preferred that X4 is S. In these embodiments where X4 is S, T, or Y, it is most preferred that X4 is phosphorylated. When X4 is D or E, these residues have a negative charge that mimics the phosphorylated state. The polypeptides of the invention are optimally effective in the methods of the invention when X4 is phosphorylated, is a phosphoserine or phosphotyrosine mimic, or is another mimic of a phosphorylated amino acid residue, such as a D or E residue. Examples of phosphoserine mimics include, but are not limited to, sulfoserine, amino acid mimics containing a methylene substitution for the phosphate oxygen, 4-phosphono(difluoromethyl)phenylanaline, and L-2-amino-4-(phosphono)-4,4-difluorobutanoic acid. Other phosphoserine mimics can be made by those of skill in the art; for example, see Otaka et al., Tetrahedron Letters 36:927-930 (1995). Examples of phosphotyrosine mimics include, but are not limited to, phosphonomethylphenylalanine, difluorophosphonomethylphenylalanine, fluoro-O-malonyltyrosine and O-malonyltyrosine. (See, for example, Akamatsu et. al., Bioorg Med Chem 1997 January;5(1):157-63).

In another preferred embodiment, X1 is one or more molecules comprising an aromatic ring. In one preferred embodiment, the one or molecules comprising an aromatic ring are amino acids, and X1 is (F/Y/W), wherein "z" is 1-5 amino acids. Thus, for example, X1 can be 1 or 2 amino acid residues of any combination of F, Y, and W, such as F, FF, Y, YY, W, WW, FY, FW, YF, YW, WY, and WF. Alternatively, X1 an be a 3, 4, or 5 amino acid combination of F, Y, and W. In another preferred embodiment, the molecule comprising an aromatic ring is selected from the group of molecules comprising one or more aromatic rings which can optionally be substituted with halogen, lower alkyl, lower alkylthio, trifluoromethyl, lower acyloxy, aryl, and heteroaryl. In a most preferred embodiment, the one or more molecule comprising one or more aromatic ring comprise 9-fluorenylmethyl (Fm). Examples of such molecules include, but are not limited to 9-fluorenylmethylcarbonyl, 9-fluorenylmethylcarbamates, 9-fluorenylmethylcarbonates, 9-fluorenylmethyl esters, 9-fluorenylmethylphosphates, and S-9-fluorenylmethyl thioethers. In embodiments wherein the molecule comprising an aromatic ring is not an amino acid, it can be attached to the polypeptide by methods known in the art, including but not limited to, standard Fmoc protection chemistry employed in peptide synthesis.

According to various embodiments of the polypeptides of general formula I, X3 is 0, 1, 2, 3, or 4 amino acids of the sequence WLRR (SEQ ID NO:1). If X3 consists of only one amino acid of the sequence, an "R" is present, since it is the carboxy-terminal amino acid of the sequence and it would be present at the amino terminus of the rest of the A(X4) APLP (SEQ ID NO: 2) sequence. If X3 consists of two amino acids of WLRR (SEQ ID NO:1), then the two amino acids added will be "RR". Other variations will be apparent to one of skill in the art based on the teachings herein.

Similarly, variations in the residues that can make up X5 will be apparent to one of skill in the art based on the teachings herein.

Thus, according to these various aspects, a representative sample of polypeptides according to general formula I include, but are not limited to the following: $(ASAPLP)_u$ (SEQ ID NO:3); $(ATAPLP)_u$ (SEQ ID NO:4); $(RASAPLP)_u$ (SEQ ID NO:5); $(RATAPLP)_u$ (SEQ ID NO:6); $(AYAPLP)_u$ (SEQ ID NO:7); $(RAYAPLP)_u$ (SEQ ID NO:8); $(RRASAPLP)_u$ (SEQ ID NO:9); $(LRRASAPLP)_u$ (SEQ ID NO:10); $(WLRRASAPLP)_u$; (SEQ ID NO:11) $(RRATAPLP)_u$ (SEQ ID NO:12); $(LRRATAPLP)_u$ (SEQ ID NO:13); $(WLRRATAPLP)_u$ (SEQ ID NO:14); $(RRAYAPLP)_u$ (SEQ ID NO:15); $(LRRAYAPLP)_u$ (SEQ ID NO:16); $(WLRRAYAPLP)_u$ (SEQ ID NO:17); $(RRASAPLPG)_u$ (SEQ ID NO:18); $(RRASAPLPD)_u$ (SEQ ID NO:19); $(RRASAPLPGL)_u$ (SEQ ID NO:20); $(RRASAPLPGK)_u$ (SEQ ID NO:21); $(RRASAPLPDL)_u$ (SEQ ID NO:22); $(RRASAPLPDK)_u$ (SEQ ID NO:23); $(RRASAPLPGLS)_u$ (SEQ ID NO:24); $(RRASAPLPGLT)_u$ (SEQ ID NO:25); $(RRASAPLPGKS)_u$ (SEQ ID NO:26); $(RRASAPLPGKT)_u$ (SEQ ID NO:27); $(RRASAPLPDLS)_u$ (SEQ ID NO:28); $RRASAPLPDLT)_u$ (SEQ ID NO:29); $(RRASAPLPDKS)_u$ (SEQ ID NO:30); $(RRASAPLPDKT)_u$ (SEQ ID NO:31); $(LRRASAPLPG)_u$ (SEQ ID NO:32); $(LRRASAPLPD)_u$ (SEQ ID NO:33); $(LRRASAPLPGL)_u$ (SEQ ID NO:34); $(LRRASAPLPGK)_u$ (SEQ ID NO:35); $(LRRASAPLPDL)_u$ (SEQ ID NO:36); $(LRRASAPLPDK)_u$ (SEQ ID NO:37); $(LRRASAPLPGLS)_u$ (SEQ ID NO:38); $(LRRASAPLPGLT)_u$ (SEQ ID NO:39); $(LRRASAPLPGKS)_u$ (SEQ ID NO:40); $(LRRASAPLPGKT)_u$ (SEQ ID NO:41); $(LRRASAPLPDLS)_u$ (SEQ ID NO:42); $(LRRASAPLPDLT)_u$ (SEQ ID NO:43); $(LRRASAPLPDKS)_u$ (SEQ ID NO:44); $(LRRASAPLPDKT)_u$ (SEQ ID NO:45); $(WLRRASAPLPG)_u$ (SEQ ID NO:46); $(WLRRASAPLPD)_u$ (SEQ ID NO:47); $(WLRRASAPLPGL)_u$ (SEQ ID NO:48); $(WLRRASAPLPGK)_u$ (SEQ ID NO:49); $(WLRRASAPLPDL)_u$ (SEQ ID NO:50); $(WLRRASAPLPDK)_u$ (SEQ ID NO:51); $(WLRRASAPLPGLS)_u$ (SEQ ID NO:52); $(WLRRASAPLPGLT)_u$ (SEQ ID NO:53); $(WLRRASAPLPGKS)_u$ (SEQ ID NO:54); $(WLRRASAPLPGKT)_u$ (SEQ ID NO:55); $(WLRRASAPLPDLS)_u$ (SEQ ID NO:56); $(WLRRASAPLPDLT)_u$ (SEQ ID NO:57); $(WLRRASAPLPDKS)_u$ (SEQ ID NO:58); $(WLRRASAPLPDKT)_u$ (SEQ ID NO:59); $(RRATAPLPG)_u$ (SEQ ID NO:60); $(RRATAPLPD)_u$ (SEQ ID NO:61); $(RRATAPLPGL)_u$ (SEQ ID NO:62); $(RRATAPLPGK)_u$ (SEQ ID NO:63); $(RRATAPLPDL)_u$ (SEQ ID NO:64); $(RRATAPLPDK)_u$ (SEQ ID NO:65); $(RRATAPLPGLS)_u$ (SEQ ID NO:66); $(RRATAPLPGLT)_u$ (SEQ ID NO:67); $(RRATAPLPGKS)_u$ (SEQ ID NO:68); $(RRATAPLPGKT)_u$ (SEQ ID NO:69); $(RRATAPLPDLS)_u$ (SEQ ID NO:70); (RRATAPLPDLT) (SEQ ID NO:71); (RRATAPLPDKS)$_u$ (SEQ ID NO:72); (RRATAPLPDKT)$_u$ (SEQ ID NO:73); (LRRATAPLPG)$_u$ (SEQ ID NO:74); (LRRATAPLPD)$_u$ (SEQ ID NO:75); (LRRATAPLPGL)$_u$ (SEQ ID NO:76); (LRRATAPLPGK)$_u$ (SEQ ID NO:77); (LRRATAPLPDL)$_u$ (SEQ ID NO:78); (LRRATAPLPDK)$_u$ (SEQ ID NO:79); (LRRATAPLPGLS)$_u$ (SEQ ID NO:80); (LRRATAPLPGLT)$_u$ (SEQ ID NO:81); (LRRATAPLPGKS)$_u$ (SEQ ID NO:82); (LRRATAPLPGKT)$_u$ (SEQ ID NO:83); (LRRATAPLPDLS)$_u$ (SEQ ID NO:84); (LRRATAPLPDLT)$_u$ (SEQ ID NO:85); (LRRATAPLPDKS)$_u$ (SEQ ID NO:86); (LRRATAPLPDKT) (SEQ ID NO:87); (WLRRATAPLPG) (SEQ ID NO:88); (WLRRATAPLPD)$_u$ (SEQ ID NO:89); (WLRRATAPLPGL) (SEQ ID NO:90); (WLRRATAPLPGK) (SEQ ID NO:91); (WLRRATAPLPDL)$_u$ (SEQ ID NO:92); (WLRRATAPLPDK)$_u$ (SEQ ID NO:93); (WLRRATAPLPGLS)$_u$ (SEQ ID NO:94); (WLRRATAPLPGLT)$_u$ (SEQ ID NO:95); (WLRRATAPLPGKS)$_u$ (SEQ ID NO:96); (WLRRATAPLPGKT)$_u$ (SEQ ID NO:97); (WLRRATAPLPDLS)$_u$ (SEQ ID NO:98); (WLRRATAPLPDLT)$_u$ (SEQ ID NO:99); (WLRRATAPLPDKS)$_u$ (SEQ ID NO:100); (WLRRATAPLPDKT) (SEQ ID NO:101); (RRAYAPLPG) (SEQ ID NO:102); (RRAYAPLPD)$_u$ (SEQ ID NO:103); (RRAYAPLPGL) (SEQ ID NO:104); (RRAYAPLPGK)$_u$ (SEQ ID NO:105); (RRAYAPLPDL)$_u$ (SEQ ID NO:106); (RRAYAPLPDK) (SEQ ID NO:107); (RRAYAPLPGLS) (SEQ ID NO:108); (RRAYAPLPGLT)$_u$ (SEQ ID NO:109); (RRAYAPLPGKS)$_u$ (SEQ ID NO:110); (RRAYAPLPGKT)$_u$ (SEQ ID NO:111); (RRAYAPLPDLS)$_u$ (SEQ ID NO:112); (RRAYAPLPDLT) (SEQ ID NO:113); (RRAYAPLPDKS)$_u$ (SEQ ID NO:114); (RRAYAPLPDKT)$_u$ (SEQ ID NO:115); (LRRAYAPLPG)$_u$ (SEQ ID NO:116); (LRRAYAPLPD)$_u$ (SEQ ID NO:117); (LRRAYAPLPGL)$_u$ (SEQ ID NO:118); (LRRAYAPLPGK)$_u$ (SEQ ID NO:119); (LRRAYAPLPDL)$_u$ (SEQ ID NO:120); (LRRAYAPLPDK)$_u$ (SEQ ID NO:121); (LRRAYAPLPGLS)$_u$ (SEQ ID NO:122); (LRRAYAPLPGLT)$_u$ (SEQ ID NO:123); (LRRAYAPLPGKS)$_u$ (SEQ ID NO:124); (LRRAYAPLPGKT)$_u$ (SEQ ID NO:125); (LRRAYAPLPDLS)$_u$ (SEQ ID NO:126); (LRRAYAPLPDLT)$_u$ (SEQ ID NO:127); (LRRAYAPLPDKS)$_u$ (SEQ ID NO:128); (LRRAYAPLPDKT)$_u$ (SEQ ID NO:129); (WLRRAYAPLPG)$_u$ (SEQ ID NO:130); (WLRRAYAPLPD)$_u$ (SEQ ID NO:131); (WLRRAYAPLPGL)$_u$ (SEQ ID NO:132); (WLRRAYAPLPGK)$_u$ (SEQ ID NO:133); (WLRRAYAPLPDL)$_u$ (SEQ ID NO:134); (WLRRAYAPLPDK)$_u$ (SEQ ID NO:135); (WLRRAYAPLPGLS)$_u$ (SEQ ID NO:136); (WLRRAYAPLPGLT)$_u$ (SEQ ID NO:137); (WLRRAYAPLPGKS)$_u$ (SEQ ID NO:138); (WLRRAYAPLPGKT)$_u$ (SEQ ID NO:139); (WLRRAYAPLPDLS)$_u$ (SEQ ID NO:140); (WLRRAYAPLPDLT)$_u$ (SEQ ID NO:141); (WLRRAYAPLPDKS)$_u$ (SEQ ID NO:142); and (WLRRAYAPLPDKT) (SEQ ID NO:143); ((F/Y/W)RRASAPLP) (SEQ ID NO:144); ((F/Y/W)LRRASAPLP)$_u$ (SEQ ID NO:145); ((F/Y/W)WLRRASAPLP)$_u$; (SEQ ID NO:146) ((F/Y/W)RRATAPLP)$_u$ (SEQ ID NO:147); ((F/Y/W)LRRATAPLP)$_u$ (SEQ ID NO:148); ((F/Y/W)WLRRATAPLP) (SEQ ID NO:149); ((F/Y/W)RRAYAPLP)$_u$ (SEQ ID NO:150); ((F/Y/W)LRRAYAPLP)$_u$ (SEQ ID NO:151); ((F/Y/W)WLRRAYAPLP)$_u$ (SEQ ID NO:152); ((F/Y/W)RRASAPLPG) (SEQ ID NO:153); ((F/Y/W)RRASAPLPD) (SEQ ID NO:154); ((F/Y/W)RRASAPLPGL) (SEQ ID NO:155); ((F/Y/W)RRASAPLPGK)$_u$ (SEQ ID NO:156); ((F/Y/W)RRASAPLPDL)$_u$ (SEQ ID NO:157); ((F/Y/W)RRASAPLPDK) (SEQ ID NO:158); ((F/Y/W)RRASAPLPGLS) (SEQ ID NO:159); ((F/Y/W)RRASAPLPGLT)$_u$ (SEQ ID NO:160); ((F/Y/W)RRASAPLPGKS)$_u$; (SEQ ID NO:161); ((F/Y/W)RRASAPLPGKT)$_u$ (SEQ ID NO:162); ((F/Y/W)RRASAPLPDLS)$_u$ (SEQ ID NO:163); ((F/Y/W)RRASAPLPDLT)$_u$ (SEQ ID NO:164); ((F/Y/W)RRASAPLPDKS) (SEQ ID NO:165); ((F/Y/W)RRASAPLPDKT)$_u$ (SEQ ID NO:166); ((F/Y/W)LRRASAPLPG) (SEQ ID NO:167); ((F/Y/W)LRRASAPLPD) (SEQ ID NO:168); ((F/Y/W))LRRASAPLPGL)$_u$ (SEQ ID NO:169); ((F/Y/W)LRRASAPLPGK)$_u$ (SEQ ID NO:170); ((F/Y/W)LRRASAPLPDL)$_u$ (SEQ ID NO:171); ((F/Y/W)LRRASAPLPDK) (SEQ ID NO:172); ((F/Y/W)LRRASAPLPGLS)$_u$ (SEQ ID NO:173); ((F/Y/W)LRRASAPLPGLT) (SEQ ID NO:174); ((F/Y/W)LRRASAPLPGKS)$_u$ (SEQ ID NO:175); ((F/Y/W)LRRASAPLPGKT)$_u$ (SEQ ID NO:176); ((F/Y/W)LRRASAPLPDLS)$_u$ (SEQ ID NO:177); ((F/Y/W)LRRASAPLPDLT)$_u$ (SEQ ID NO:178); ((F/Y/W)LRRASAPLPDKS)$_u$ (SEQ ID NO:179); ((F/Y/W)LRRASAPLPDKT)$_u$ (SEQ ID NO:180); ((F/Y/W)WLRRASAPLPG)$_u$ (SEQ ID NO:181); ((F/Y/W)WLRRASAPLPD)$_u$ (SEQ ID NO:182); ((F/Y/W)WLRRASAPLPGL)$_u$ (SEQ ID NO:183); ((F/Y/W)WLRRASAPLPGK)$_u$ (SEQ ID NO:184); ((F/Y/W)WLRRASAPLPDL)$_u$ (SEQ ID NO:185); ((F/Y/W)WLRRASAPLPDK)$_u$ (SEQ ID NO:186); ((F/Y/W)WLRRASAPLPGLS)$_u$ (SEQ ID NO:187); ((F/Y/W)WLRRASAPLPGLT)$_u$ (SEQ ID NO:188); ((F/Y/W)WLRRASAPLPGKS)$_u$ (SEQ ID NO:189); ((F/Y/W)WLRRASAPLPGKT)$_u$ (SEQ ID NO:190); ((F/Y/W)WLRRASAPLPDLS)$_u$ (SEQ ID NO:191); ((F/Y/W)WLRRASAPLPDLT)$_u$ (SEQ ID NO:192); ((F/Y/W)WLRRASAPLPDKS)$_u$ (SEQ ID NO:193); ((F/Y/W)WLRRASAPLPDKT)$_u$ (SEQ ID NO:194); ((F/Y/W)RRATAPLPG)$_u$ (SEQ ID NO:195); ((F/Y/W)RRATAPLPD)$_u$ (SEQ ID NO:196); ((F/Y/W)RRATAPLPGL)$_u$ (SEQ ID NO:197); ((F/Y/W)RRATAPLPGK)$_u$ (SEQ ID NO:198); ((F/Y/W)RRATAPLPDL)$_u$ (SEQ ID NO:199); ((F/Y/W)RRATAPLPDK)$_u$ (SEQ ID NO:200); ((F/Y/W)RRATAPLPGLS) (SEQ ID NO:201); ((F/Y/W)RRATAPLPGLT)$_u$ (SEQ ID NO:202); ((F/Y/W)RRATAPLPGKS)$_u$ (SEQ ID NO:203); ((F/Y/W)RRATAPLPGKT)$_u$ (SEQ ID NO:204); ((F/Y/W)RRATAPLPDLS)$_u$ (SEQ ID NO:205); ((F/Y/W)RRATAPLPDLT)$_u$ (SEQ ID NO:206); ((F/Y/W)RRATAPLPDKS) (SEQ ID NO:207); ((F/Y/W)RRATAPLPDKT)$_u$ (SEQ ID NO:208); ((F/Y/W)LRRATAPLPG)$_u$ (SEQ ID NO:209); ((F/Y/W)LRRATAPLPD)$_u$ (SEQ ID NO:210); ((F/Y/W)LRRATAPLPGL)$_u$ (SEQ ID NO:211); ((F/Y/W)LRRATAPLPGK)$_u$ (SEQ ID NO:212); ((F/Y/W)LRRATAPLPDL) (SEQ ID NO:213); ((F/Y/W)LRRATAPLPDK)$_u$ (SEQ ID NO:214); ((F/Y/W)LRRATAPLPGLS)$_u$ (SEQ ID NO:215); ((F/Y/W)LRRATAPLPGLT) (SEQ ID NO:216); ((F/Y/W)LRRATAPLPGKS)$_u$ (SEQ ID NO:217); ((F/Y/W)LRRATAPLPGKT)$_u$ (SEQ ID NO:218); ((F/Y/W)LRRATAPLPDLS)$_u$ (SEQ ID NO:219); ((F/Y/W)LRRATAPLPDLT)$_u$ (SEQ ID NO:220); ((F/Y/W)LRRATAPLPDKS)$_u$ (SEQ ID NO:221); ((F/Y/W)LRRATAPLPDKT) (SEQ ID NO:222); ((FIYIW)WLRRATAPLPG)$_u$ (SEQ ID NO:223); ((F/Y/W)WLRRATAPLPD)$_u$ (SEQ ID NO:224); ((F/Y/W)WLRRATAPLPGL)$_u$ (SEQ ID NO:225); ((F/Y/W)WLRRATAPLPGK)$_u$ (SEQ ID NO:226); ((F/Y/W)WLRRATAPLPDL)$_u$ (SEQ ID NO:227); ((F/Y/W)WLRRATAPLPDK)$_u$ (SEQ ID NO:228); ((F/Y/W)WLRRATAPLPGLS)$_u$ (SEQ ID NO:229); ((F/Y/W)WLRRATAPLPGLT)$_u$ (SEQ ID NO:230); ((F/Y/W)WLRRATAPLPGKS)$_u$ (SEQ ID NO:231); ((F/Y/W)WLRRATAPLPGKT)$_u$ (SEQ ID NO:232); ((F/Y/W)WLRRATAPLPDLS)$_u$ (SEQ ID NO:233); ((F/Y/W)WLRRATAPLPDLT)$_u$ (SEQ ID NO:234); ((F/Y/W)WLRRATAPLPDKS)$_u$ (SEQ ID NO:235); ((F/Y/W)WLRRATAPLPDKT)$_u$ (SEQ ID NO:236); ((F/Y/W)RRAYAPLPG)$_u$ (SEQ ID NO:237); ((F/Y/W)

| | | |
|---|---|---|
| RRAYAPLPD)ᵤ | (SEQ ID NO:238); | ((F/Y/W) |
| RRAYAPLPGL)ᵤ | (SEQ ID NO:239); | ((F/Y/W) |
| RRAYAPLPGK)ᵤ | (SEQ ID NO:240); | ((F/Y/W) |
| RRAYAPLPDL)ᵤ | (SEQ ID NO:241); | ((F/Y/W) |
| RRAYAPLPDK)ᵤ | (SEQ ID NO:242); | ((F/Y/W) |
| RRAYAPLPGLS)ᵤ | (SEQ ID NO:243); | ((F/Y/W) |
| RRAYAPLPGLT)ᵤ | (SEQ ID NO:244); | ((F/Y/W) |
| RRAYAPLPGKS)ᵤ | (SEQ ID NO:245); | ((F/Y/W) |
| RRAYAPLPGKT)ᵤ | (SEQ ID NO:246); | ((F/Y/W) |
| RRAYAPLPDLS)ᵤ | (SEQ ID NO:247); | ((F/Y/W) |
| RRAYAPLPDLT)ᵤ | (SEQ ID NO:248); | ((F/Y/W) |
| RRAYAPLPDKS)ᵤ | (SEQ ID NO:249); | ((F/Y/W) |
| RRAYAPLPDKT)ᵤ | (SEQ ID NO:250); | ((F/Y/W) |
| LRRAYAPLPG)ᵤ | (SEQ ID NO:251); | ((F/Y/W) |
| LRRAYAPLPD)ᵤ | (SEQ ID NO:252); | ((F/Y/W) |
| LRRAYAPLPGL)ᵤ | (SEQ ID NO:253); | ((F/Y/W) |
| LRRAYAPLPGK)ᵤ | (SEQ ID NO:254); | ((F/Y/W) |
| LRRAYAPLPDL)ᵤ | (SEQ ID NO:255); | ((F/Y/W) |
| LRRAYAPLPDK)ᵤ | (SEQ ID NO:256); | ((F/Y/W) |
| LRRAYAPLPGLS)ᵤ | (SEQ ID NO:257); | ((F/Y/W) |
| LRRAYAPLPGLT)ᵤ | (SEQ ID NO:258); | ((F/Y/W) |
| LRRAYAPLPGKS)ᵤ | (SEQ ID NO:259); | ((F/Y/W) |
| LRRAYAPLPGKT)ᵤ | (SEQ ID NO:260); | ((F/Y/W) |
| LRRAYAPLPDLS)ᵤ | (SEQ ID NO:261); | ((F/Y/W) |
| LRRAYAPLPDLT)ᵤ | (SEQ ID NO:262); | ((F/Y/W) |
| LRRAYAPLPDKS)ᵤ | (SEQ ID NO:263); | ((F/Y/W) |
| LRRAYAPLPDKT)ᵤ | (SEQ ID NO:264); | ((F/Y/W) |
| WLRRAYAPLPG)ᵤ | (SEQ ID NO:265); | ((F/Y/W) |
| WLRRAYAPLPD)ᵤ | (SEQ ID NO:266); | ((F/Y/W) |
| WLRRAYAPLPGL)ᵤ | (SEQ ID NO:267); | ((F/Y/W) |
| WLRRAYAPLPGK)ᵤ | (SEQ ID NO:268); | ((F/Y/W) |
| WLRRAYAPLPDL)ᵤ | (SEQ ID NO:269); | ((F/Y/W) |
| WLRRAYAPLPDK)ᵤ | (SEQ ID NO:270); | ((F/Y/W) |
| WLRRAYAPLPGLS)ᵤ | (SEQ ID NO:271); | ((F/Y/W) |
| WLRRAYAPLPGLT)ᵤ | (SEQ ID NO:272); | ((F/Y/W) |
| WLRRAYAPLPGKS)ᵤ | (SEQ ID NO:273); | ((F/Y/W) |
| WLRRAYAPLPGKT)ᵤ | (SEQ ID NO:274); | ((F/Y/W) |
| WLRRAYAPLPDLS)ᵤ | (SEQ ID NO:275); | ((F/Y/W) |
| WLRRAYAPLPDLT)ᵤ | (SEQ ID NO:276); | ((F/Y/W) |
| WLRRAYAPLPDKS)ᵤ | (SEQ ID NO:277); and | ((F/Y/W) |
| WLRRAYAPLPDKT)ᵤ | (SEQ ID NO:278) | | wherein "u" is as defined above, and (F/Y/W) means that the residue is selected from F, Y, and W. Other specific polypeptides falling within the scope of general formula I will be readily apparent to one of skill in the art based on the teachings herein.

In a further embodiment, the polypeptides of the present invention consist of a combination of different sequences from the region [X3-A(X4)APLP-X5-]ᵤ. In this embodiment, for example, the polypeptide can consist of 1 copy of SEQ ID NO:9 and 1 copy of SEQ ID NO:143. In a different example, the polypeptide could consist of 2 copies of SEQ ID NO:200 and 3 copies of SEQ ID NO:62. It will be apparent to one of skill in the art that many such combinations are possible based on the teachings of the present invention.

In a preferred embodiment, at least one of X2 and X6 comprises a transduction domain. As used herein, the term "transduction domain" means one or more amino acid sequence or any other molecule that can carry the active domain across cell membranes. These domains can be linked to other polypeptides to direct movement of the linked polypeptide across cell membranes. In some cases the transducing molecules do not need to be covalently linked to the active polypeptide (for example, see sequence ID 291). In a preferred embodiment, the transduction domain is linked to the rest of the polypeptide via peptide bonding. (See, for example, *Cell* 55: 1179-1188, 1988; *Cell* 55: 1189-1193, 1988; *Proc Natl Acad Sci USA* 91: 664-668, 1994; *Science* 285: 1569-1572, 1999; *J Biol Chem* 276: 3254-3261, 2001; and *Cancer Res* 61: 474-477, 2001) In this embodiment, any of the polypeptides as described above would include at least one transduction domain. In a further embodiment, both X2 and X6 comprise transduction domains. In a further preferred embodiment, the transduction domain(s) is/are selected from the group consisting of (R)₄₋₉ (SEQ ID NO:279); GRKKRRQRRRPPQ (SEQ ID NO:280); AYARAAARQARA (SEQ ID NO:281); DAATATRGR-SAASRPTERPRAPARSASRPRRPVE (SEQ ID NO:282); GWTLNSAGYLLGLINLKALAALAKKIL (SEQ ID NO:283); PLSSIFSRIGDP (SEQ ID NO:284); AAVALL-PAVLLALLAP (SEQ ID NO:285); AAVLLPVLLAAP (SEQ ID NO:286); VTVLALGALAGVGVG (SEQ ID NO:287); GALFLGWLGAAGSTMGAWSQP (SEQ ID NO:288); GWTLNSAGYLLGLINLKALAALAKKIL (SEQ ID NO:289); KLALKLALKALKAALKLA (SEQ ID NO:290); KETWWETWWTEWSQPKKKRKV (SEQ ID NO:291); KAFAKLAARLYRKAGC (SEQ ID NO:292); KAFAKLAARLYRAAGC (SEQ ID NO:293); AAFAK-LAARLYRKAGC (SEQ ID NO:294); KAFAALAAR-LYRKAGC (SEQ ID NO:295); KAFAKLAAQLYRKAGC (SEQ ID NO:296), and AGGGGYGRKKRRQRRR (SEQ ID NO:306).

In another embodiment, the present invention provides a polypeptide comprising a sequence according to general formula II:

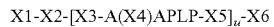

X1-X2-[X3-A(X4)APLP-X5]ᵤ-X6 wherein X1 is absent or is one or more molecules comprising one or more aromatic ring;

X2 is absent or comprises a cell transduction domain;

X3 is 0-14 amino acids of the sequence of heat shock protein 20 between residues 1 and 14 of SEQ ID NO:297;

X4 is selected from the group consisting of S, T, Y, D, E, hydroxylysine, hydroxyproline, phosphoserine analogs and phosphotyrosine analogs;

X5 is 0-140 amino acids of heat shock protein 20 between residues 21 and 160 of SEQ ID NO:297;

X6 is absent or comprises a cell transduction domain; and wherein at least one of X2 and X6 comprise a transduction domain.

Thus, in various preferred embodiments of the polypeptide of general formula II, X4 is S, T, Y, D, E, a phosphoserine analog, or a phosphotyrosine analog. In a preferred embodiment, X4 is S, T, or Y. In a more preferred embodiment, X4 is S or T. In a most preferred embodiment, X4 is S.

In these embodiments where X4 is S, T, or Y, it is most preferred that X4 is phosphorylated. When X4 is D or E, these residues have a negative charge that mimics the phosphorylated state. The polypeptides of the invention are optimally effective in the methods of the invention when X4 is phosphorylated, is a phosphoserine or phosphotyrosine mimic, or is another mimic of a phosphorylated amino acid residue, such as a D or E residue.

In a further preferred embodiment, X1 is one or more molecules comprising one or more aromatic ring, as disclosed above, with preferred embodiments as disclosed above.

According to these embodiments, the polypeptide comprises at least one transduction domain. In a further embodiment, both X2 and X6 comprise a transduction domain. Preferred embodiments of such transduction domains are as described above.

One preferred embodiment of the polypeptide of general formula II comprises full length HSP20 (X1-X2-SEQ ID NO:297-X6).

Met Glu Ile Pro Val Pro Val Gln Pro Ser Trp Leu Arg Arg Ala Ser Ala Pro Leu Pro Gly Leu Ser Ala Pro Gly Arg Leu Phe Asp Gln Arg Phe Gly Glu Gly Leu Leu Glu Ala Glu Leu Ala Ala Leu Cys Pro Thr Thr Leu Ala Pro Tyr Tyr Leu Arg Ala Pro Ser Val Ala Leu Pro Val Ala Gln Val Pro Thr Asp Pro Gly His Phe Ser Val Leu Leu Asp Val Lys His Phe Ser Pro Glu Glu Ile Ala Val Lys Val Val Gly Glu His Val Glu Val His Ala Arg His Glu Glu Arg Pro Asp Glu His Gly Phe Val Ala Arg Glu Phe His Arg Arg Tyr Arg Leu Pro Pro Gly Val Asp Pro Ala Ala Val Thr Ser Ala Leu Ser Pro Glu Gly Val Leu Ser Ile Gln Ala Ala Pro Ala Ser Ala Gln Ala Pro Pro Pro Ala Ala Ala Lys. (SEQ ID NO:297)

Another preferred embodiment of the polypeptide of general formula II comprises full length HSP20 with the serine at position 16 substitute with aspartic acid (X1-X2-SEQ ID NO:298-X6):

Met Glu Ile Pro Val Pro Val Gln Pro Ser Trp Leu Arg Arg Ala Asp Ala Pro Leu Pro Gly Leu Ser Ala Pro Gly Arg Leu Phe Asp Gln Arg Phe Gly Glu Gly Leu Leu Glu Ala Glu Leu Ala Ala Leu Cys Pro Thr Thr Leu Ala Pro Tyr Tyr Leu Arg Ala Pro Ser Val Ala Leu Pro Val Ala Gln Val Pro Thr Asp Pro Gly His Phe Ser Val Leu Leu Asp Val Lys His Phe Ser Pro Glu Glu Ile Ala Val Lys Val Val Gly Glu His Val Glu Val His Ala Arg His Glu Glu Arg Pro Asp Glu His Gly Phe Val Ala Arg Glu Phe His Arg Arg Tyr Arg Leu Pro Pro Gly Val Asp Pro Ala Ala Val Thr Ser Ala Leu Ser Pro Glu Gly Val Leu Ser Ile Gln Ala Ala Pro Ala Ser Ala Gln Ala Pro Pro Pro Ala Ala Ala Lys. (SEQ ID NO:298)

Another preferred embodiment of the polypeptide of general formula II comprises full length HSP20 with the serine at position 16 substitute with glutamic acid (X1-X2-SEQ ID NO:299-X6):

Met Glu Ile Pro Val Pro Val Gln Pro Ser Trp Leu Arg Arg Ala Glu Ala Pro Leu Pro Gly Leu Ser Ala Pro Gly Arg Leu Phe Asp Gln Arg Phe Gly Glu Gly Leu Leu Glu Ala Glu Leu Ala Ala Leu Cys Pro Thr Thr Leu Ala Pro Tyr Tyr Leu Arg Ala Pro Ser Val Ala Leu Pro Val Ala Gln Val Pro Thr Asp Pro Gly His Phe Ser Val Leu Leu Asp Val Lys His Phe Ser Pro Glu Glu Ile Ala Val Lys Val Val Gly Glu His Val Glu Val His Ala Arg His Glu Glu Arg Pro Asp Glu His Gly Phe Val Ala Arg Glu Phe His Arg Arg Tyr Arg Leu Pro Pro Gly Val Asp Pro Ala Ala Val Thr Ser Ala Leu Ser Pro Glu Gly Val Leu Ser Ile Gln Ala Ala Pro Ala Ser Ala Gln Ala Pro Pro Pro Ala Ala Ala Lys. (SEQ ID NO:299)

Other preferred embodiments according to general formula II are the peptides disclosed above as embodiments of general formula I with the required transduction domain at either X2 or X6, or both. Still further preferred embodiments according to general formula II are the following:

X1-X2-SEQ ID NO:300-X6, wherein (SEQ ID NO: 300) is Trp Leu Arg Arg Ala Ser Ala Pro Leu Pro Gly Leu Lys;

X1-X2-SEQ ID NO:301-X6, wherein (SEQ ID NO: 301) is Trp Leu Arg Arg Ala Asp Ala Pro Leu Pro Gly Leu Lys;. and X1-X2-SEQ ID NO:302-X6, wherein (SEQ ID NO: 302) is Trp Leu Arg Arg Ala Glu Ala Pro Leu Pro Gly Leu Lys.

In these embodiments of the polypeptides according to general formula II, it is preferred that the polypeptides are phosphorylated, most preferably at residue 16, or contain phosphorylation mimics at the position of amino acid residue 16.

In a further aspect, the present invention provides a composition, comprising one or more polypeptides of the present invention, and an inhibitor of HSP27. HSP27 is closely related to HSP20; the two proteins often co-exist in macromolecular aggregates, and both are actin-associated proteins. Increases in the phosphorylation of HSP27 are associated with smooth muscle contraction, and transfection of cells with dominant active phosphorylated mutants of HSP27 leads to stress fiber formation (*Mol Cell Biol* 15: 505-516, 1995). Furthermore, increases in the phosphorylation of HSP27 are associated with smooth muscle cell migration. HSP20, in contrast, promotes vasorelaxation, and the data presented herein demonstrates that phosphorylated analogues of HSP20 lead to a loss of stress fiber formation, and inhibit smooth muscle cell proliferation and migration (See the examples below). Thus, the data indicate that HSP20 and HSP27 have opposing functions. Therefore, the combined use of one or more polypeptides of the invention and an inhibitor of HSP27 will have enhanced efficacy in carrying out the methods of the invention for inhibiting smooth muscle cell proliferation and/or migration, for promoting smooth muscle relaxation, and for inhibiting smooth muscle spasm (see below).

As used herein, an "inhibitor" of HSP27 includes HSP27 antibodies, anti-sense HSP27 nucleic acids, or small molecule inhibitors of the phosphorylation of HSP27, such as SB203580 (available from SmithKline Beecham).

The polypeptides may be subjected to conventional pharmaceutical operations such as sterilization and/or may contain conventional adjuvants, such as preservatives, stabilizers, wetting agents, emulsifiers, buffers etc.

In another aspect, the present invention provides pharmaceutical compositions, comprising one or more of the polypeptides disclosed herein, and a pharmaceutically acceptable carrier. Such pharmaceutical compositions are especially useful for carrying out the methods of the invention described below.

For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The polypeptides or pharmaceutical compositions thereof may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Preferred embodiments for administration vary with respect to the condition being treated, and are described in detail below.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

In another aspect, the present invention provides an isolated nucleic acid sequence encoding a polypeptide of the present invention. Appropriate nucleic acid sequences according to this aspect of the invention will be apparent to one of skill in the art based on the disclosure provided herein and the general level of skill in the art. One example of such a nucleic acid sequence is provided as SEQ ID NO:320.

In another aspect, the present invention provides an expression vector comprising DNA control sequences operably linked to the isolated nucleic acid molecules of the present invention, as disclosed above. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites.

Such expression vectors can be of any type known in the art, including but not limited plasmid and viral-based expression vectors.

In a further aspect, the present invention provides genetically engineered host cells comprising the expression vectors of the invention. Such host cells can be prokaryotic cells or eukaryotic cells, and can be either transiently or stably transfected, or can be transduced with viral vectors.

In another aspect, the invention provides improved biomedical devices, wherein the biomedical devices comprise one or more of the polypeptides of the present invention disposed on or in the biomedical device. In a preferred embodiment, the one or more polypeptides are phosphorylated, as discussed above.

As used herein, a "biomedical device" refers to a device to be implanted into a subject, for example, a human being, in order to bring about a desired result. Particularly preferred biomedical devices according to this aspect of the invention include, but are not limited to, stents, grafts, shunts, stent grafts, fistulas, angioplasty devices, balloon catheters and any implantable drug delivery device.

As used herein, the term "grafts" refers to both natural and prosthetic grafts and implants. In a most preferred embodiment, the graft is a vascular graft.

As used herein, the term "stent" includes the stent itself, as well as any sleeve or other component that may be used to facilitate stent placement.

As used herein, "disposed on or in" means that the one or more polypeptides can be either directly or indirectly in contact with an outer surface, an inner surface, or embedded within the biomedical device. "Direct" contact refers to disposition of the polypeptides directly on or in the device, including but not limited to soaking a biomedical device in a solution containing the one or more polypeptides, spin coating or spraying a solution containing the one or more polypeptides onto the device, implanting any device that would deliver the polypeptide, and administering the polypeptide through a catheter directly on to the surface or into any organ.

"Indirect" contact means that the one or more polypeptides do not directly contact the biomedical device. For example, the one or more polypeptides may be disposed in a matrix, such as a gel matrix or a viscous fluid, which is disposed on the biomedical device. Such matrices can be prepared to, for example, modify the binding and release properties of the one or more polypeptides as required.

In a further embodiment, the biomedical device further comprises an inhibitor of the small heat shock protein HSP27 disposed on or in the biomedical device. In a preferred embodiment, such inhibitors are selected from HSP27 antibodies, anti-sense HSP27 nucleic acids, or small molecule inhibitors of the phosphorylation of HSP27, such as SB203580.

In another aspect, the invention provides methods for inhibiting smooth muscle cell proliferation and/or migration, comprising contacting the smooth muscle cells with an amount effective to inhibit smooth muscle cell proliferation and/or migration of HSP20, or functional equivalents thereof, such as one or more polypeptide according to general formula I or II. In a most preferred embodiment, the one or more polypeptides are phosphorylated as disclosed above. In a further embodiment, the method further comprises contacting the smooth muscle cells with an amount effective to inhibit smooth muscle cell proliferation and/or migration of an inhibitor of the small heat shock protein HSP27. In a further embodiment, the method further comprises contacting the cells with an amount of PKG sufficient to stimulate HSP20 phosphorylation, wherein the contacting comprises transfecting the cells with an expression vector that is capable of directing the expression of PKG, or by transducing the cells with a PKG-transduction domain chimera.

Intimal hyperplasia is a complex process that leads to graft failure, and is the most common cause of failure of arterial bypass grafts. While incompletely understood, intimal hyperplasia is mediated by a sequence of events that include endothelial cell injury and subsequent vascular smooth muscle proliferation and migration from the media to the intima. This process is associated with a phenotypic modulation of the smooth muscle cells from a contractile to a synthetic phenotype. The "synthetic" smooth muscle cells secrete extracellular matrix proteins, which leads to pathologic narrowing of the vessel lumen leading to graft stenoses and ultimately graft failure. Such endothelial cell injury and subsequent smooth muscle cell proliferation and migration into the intima also characterizes restenosis, most commonly after angioplasty to clear an obstructed blood vessel. As discussed below, HSP20, and functional equivalents thereof, such as the polypeptides of general formula I and II, inhibit smooth muscle cell proliferation and migration.

In this aspect, the method can be in vitro or in vivo. In one embodiment, the method is in vitro, wherein a vein or arterial graft is contacted with HSP20 or a functional equivalent(s) thereof, prior to grafting in a patient, in order to inhibit smooth muscle cell proliferation and/or migration, and thus to inhibit subsequent intimal hyperplasia and stenosis after placement of the graft, which could lead to graft failure. This can be accomplished, for example, by delivering the recombinant expression vectors (most preferably a viral vector, such as an adenoviral vector) of the invention to the site, and transfecting the smooth muscle cells. More preferably, delivery into smooth muscle cells is accomplished by using the polypeptides of general formula I or II that include at least one transduction domain to facilitate entry into the smooth muscle cells. The examples below demonstrate the ability of the polypeptides of the invention that contain at least one transduction domain to be delivered into smooth muscle cells.

In a more preferred in vitro embodiment, the method comprises contacting the graft with one or more of the polypeptides of the invention that include at least one transduction domain. Upon placement of the graft, it is preferred that the subject receiving be treated systemically with heparin, as heparin has been shown to bind to protein transduction domains and prevent them from transducing into cells. This approach will lead to localized protein transduction of the graft alone, and not into peripheral tissues.

In various other preferred embodiments of this aspect, the method is performed in vivo, and is used to treat or prevent a disorder selected from the group consisting of intimal hyperplasia, stenosis, restenosis, and atherosclerosis. In these embodiments, the contacting may be direct, by contacting a blood vessel in a subject being treated with HSP20 or a functional equivalent(s) thereof, such as the polypeptides according to general formula I or II. For example, a liquid preparation of HSP20 or a functional equivalent(s) thereof, such as the polypeptides according to general formula I or II, can be forced through a porous catheter, or otherwise injected through a catheter to the injured site, or a gel or viscous liquid containing the one or more polypeptides could be spread on the injured site. In these embodiment of direct delivery, it is most preferred that the HSP20 or a functional equivalent(s) thereof, such as the polypeptides according to general formula I or II be delivered into smooth muscle cells at the site of injury or intervention. This can be accomplished, for example, by delivering the recombinant expression vectors (most preferably a viral vector, such as an adenoviral vector) of the invention to the site. More preferably, delivery into smooth muscle cells is accomplished by using the polypeptides of general formula I or II that include at least one transduction domain to facilitate entry into the smooth muscle cells. The examples below demonstrate the ability of the polypeptides of the invention that contain at least one transduction domain to be delivered into smooth muscle cells.

In various other preferred embodiments of this aspect of the invention, the method is performed on a subject who has undergone, is undergoing, or will undergo a procedure selected from the group consisting of angioplasty, vascular stent placement, endarterectomy, atherectomy, bypass surgery (such as coronary artery bypass surgery; peripheral vascular bypass surgeries), vascular grafting, organ transplant, prosthetic device implanting, microvascular reconstructions, plastic surgical flap construction, and catheter emplacement.

In a further embodiment of this aspect of the invention, the method is used to treat smooth muscle cell tumors. In a preferred embodiment, the tumor is a leiomyosarcoma, which is defined as a malignant neoplasm that arises from muscle. Since leiomyosarcomas can arise from the walls of both small and large blood vessels, they can occur anywhere in the body, but peritoneal, uterine, and gastro-intestinal (particularly esophageal) leiomyosarcomas are more common. Alternatively, the smooth muscle tumor can be a leiomyoma, a non-malignant smooth muscle neoplasm. In a most preferred embodiment, the one or more polypeptides are phosphorylated as disclosed above. In a further embodiment, the method further comprises contacting the smooth muscle cells with an amount effective to inhibit smooth muscle cell proliferation and/or migration of an inhibitor of the small heat shock protein HSP27.

As further discussed in the examples below, HSP20, and functional equivalents thereof, such as the polypeptides of general formula I and II, also disrupt actin stress fiber formation and adhesion plaques, each of which have been implicated in intimal hyperplasia. The data further demonstrate a direct inhibitory effect of the polypeptides of the present invention on intimal hyperplasia. Thus, in another aspect, the present invention further provides methods for treating or inhibiting one or more disorder selected from the group consisting of intimal hyperplasia, stenosis, restenosis, and atherosclerosis, comprising contacting a subject in need thereof with an amount effective to treat or inhibit intimal hyperplasia, stenosis, restenosis, and/or atherosclerosis of HSP20, or a functional equivalent thereof, such as one or more polypeptides according to general formula I or II. Delivery of the HSP20, or a functional equivalent thereof, such as one or more polypeptides according to general formula I or II, in this aspect are as disclosed above. In a most preferred embodiment, the one or more polypeptides are phosphorylated as disclosed above. In a further embodiment, the method further comprises contacting the smooth muscle cells with an amount effective to inhibit smooth muscle cell proliferation and/or migration of an inhibitor of the small heat shock protein HSP27.

In various other preferred embodiments of this aspect of the invention, the method is performed on a subject who has undergone, is undergoing, or will undergo a procedure selected from the group consisting of angioplasty, vascular stent placement, endarterectomy, atherectomy, bypass surgery, vascular grafting, microvascular reconstructions, plastic surgical flap construction, organ transplant, and catheter emplacement.

In a further aspect, the present invention provides methods to treat smooth muscle cell tumors, comprising administering to a subject in need thereof of an amount effective of HSP20, or a functional equivalent thereof, such as one or more polypeptides according to general formula I or II, to inhibit smooth muscle tumor growth and/or metastasis. In a preferred embodiment, the tumor is a leiomyosarcomas. Alternatively, the smooth muscle tumor can be a leiomyoma. In a further embodiment, the method further comprises contacting the smooth muscle cells with an amount effective to inhibit smooth muscle cell proliferation and/or migration of an inhibitor of the small heat shock protein HSP27.

In a further aspect, the present invention provides a method for treating or preventing smooth muscle spasm, comprising contacting a subject or graft in need thereof with an amount effective to inhibit smooth muscle spasm of HSP20, or a functional equivalent thereof, such as one or more polypeptides according to general formula I or II. In a most preferred embodiment, the one or more polypeptides are phosphorylated as disclosed above. In a further embodiment, the method further comprises contacting the smooth muscle with an amount effective to inhibit smooth muscle cell proliferation and/or migration of an inhibitor of the small heat shock protein HSP27. In a further embodiment, the method further comprises contacting the smooth muscle with an amount effective of PKG to stimulate HSP20 phosphorylation, as described above.

The examples below demonstrate that HSP20, and equivalents thereof, such as the polypeptides according to general formula I and II, are effective at inhibiting smooth muscle spasm, such as vasospasm. While not being limited by a specific mechanism of action, it is believed that HSP20, and equivalents thereof, such as the polypeptides according to general formula I and II, exert their anti-smooth muscle spasm effect by promoting smooth muscle vasorelaxation and inhibiting contraction.

Smooth muscles are found in the walls of blood vessels, airways, the gastrointestinal tract, and the genitourinary tract. Pathologic tonic contraction of smooth muscle constitutes spasm. Many pathological conditions are associated with spasm of vascular smooth muscle ("vasospasm"), the smooth muscle that lines blood vessels. This can cause symptoms such as angina and ischemia (if a heart artery is involved), or stroke as in the case of subarachnoid hemorrhage induced vasospasm if a brain vessel is involved. Hypertension (high blood pressure) is caused by excessive vasoconstriction, as well as thickening, of the vessel wall, particularly in the smaller vessels of the circulation.

Thus, in one embodiment of this aspect of the invention, the muscle cell spasm comprises a vasospasm, and the method is used to treat or inhibit vasospasm. Preferred embodiments of the method include, but are not limited to, methods to treat or inhibit angina, coronary vasospasm, Prinzmetal's angina (episodic focal spasm of an epicardial coronary artery), ischemia, stroke, bradycardia, and hypertension.

In another embodiment of this aspect of the invention, smooth muscle spasm is inhibited by treatment of a graft, such as a vein or arterial graft, with HSP20, or a functional equivalent thereof, such as one or more polypeptides according to general formula I or II, as described above. One of the ideal conduits for peripheral vascular and coronary reconstruction is the greater saphenous vein. However, the surgical manipulation during harvest of the conduit often leads to vasospasm. The exact etiology of vasospasm is complex and most likely multifactorial. Most investigations have suggested that vasospasm is either due to enhanced constriction or impaired relaxation of the vascular smooth muscle in the media of the vein. Numerous vasoconstricting agents such as endothelin-1 and thromboxane are increased during surgery and result in vascular smooth muscle contraction. Other vasoconstrictors such as norepinephrine, 5-hydroxytryptamine, acetylcholine, histamine, angiotensin II, and phenylephrine have been implicated in vein graft spasm. Papaverine is a smooth muscle vasodilator that has been used. In circumstances where spasm occurs even in the presence of papaverine, surgeons use intraluminal mechanical distension to break the spasm. This leads to injury to the vein graft wall and subsequent intimal hyperplasia. Intimal hyperplasia is the leading cause of graft failure.

Thus, in this embodiment, the graft can be contacted with HSP20 or a functional equivalent(s) thereof, during harvest from the graft donor, subsequent to harvest (before implantation), and/or during implantation into the graft recipient. This can be accomplished, for example, by delivering the recombinant expression vectors (most preferably a viral vector, such as an adenoviral vector) of the invention to the site, and transfecting the smooth muscle cells. More preferably, delivery into smooth muscle is accomplished by using the polypeptides of general formula I or II that include at least one transduction domain to facilitate entry into the smooth muscle cells. The examples below demonstrate the ability of the polypeptides of the invention that contain at least one transduction domain to be delivered into smooth muscle cells. During graft implantation, it is preferred that the subject receiving be treated systemically with heparin, as heparin has been shown to bind to protein transduction domains and prevent them from transducing into cells. This approach will lead to localized protein transduction of the graft alone, and not into peripheral tissues. The methods of this embodiment of the invention inhibit vein graft spasm during harvest and/or implantation of the graft, and thus improve both short and long term graft success.

In various other embodiments, the muscle cell spasm is associated with a disorder including, but not limited to pulmonary (lung) hypertension, asthma (bronchospasm), toxemia of pregnancy, pre-term labor, pre-eclampsia/eclampsia, Raynaud's disease or phenomenon, hemolyticuremia, non-occlusive mesenteric ischemia (ischemia of the intestines that is caused by inadequate blood flow to the intestines), anal fissure (which is caused by persistent spasm of the internal anal sphincter), achalasia (which is caused by persistent spasm of the lower esophageal sphincter), impotence (which is caused by a lack of relaxation of the vessels in the penis, erection requires vasodilation of the corpra cavernosal (penile) blood vessels), migraine (which is caused by spasm of the intracranial blood vessels), ischemic muscle injury associated with smooth muscle spasm, and vasculopathy, such as transplant vasculopathy (a reaction in the transplanted vessels which is similar to atherosclerosis, it involves constrictive remodeling and ultimately obliteration of the transplanted blood vessels, this is the leading cause of heart transplant failure).

Preferred routes of delivery for these various indications of the different aspects of the invention vary. Topical administration is preferred for methods involving treatment or inhibition of vein graft spasm, intimal hyperplasia, restenosis, prosthetic graft failure due to intimal hyperplasia, stent, stent graft failure due to intimal hyperplasia/constrictive remodeling, microvascular graft failure due to vasospasm, transplant vasculopathy, and male and female sexual dysfunction. As used herein, "topical administration" refers to delivering the polypeptide onto the surface of the organ.

Intrathecal administration, defined as delivering the polypeptide into the cerebrospinal fluid is the preferred route of delivery for treating or inhibiting stroke and subarachnoid hemorrhage induced vasospasm. Intraperitoneal administration, defined as delivering the polypeptide into the peritoneal cavity, is the preferred route of delivery for treating or inhibiting non-occlusive mesenteric ischemia. Oral administration is the preferred route of delivery for treating or inhibiting achalasia. Intravenous administration is the preferred route of delivery for treating or inhibiting hypertension and bradycardia. Administration via suppository is preferred for treating or inhibiting anal fissure. Aerosol delivery is preferred for treating or inhibiting asthma (ie: bronchospasm). Intrauterine administration is preferred for treating or inhibiting pre-term labor and pre-eclampsia/eclampsia.

In practicing these various aspects of the invention, the amount or dosage range of the polypeptides or pharmaceutical compositions employed is one that effectively teats or inhibits one or more of smooth muscle cell proliferation, smooth muscle cell migration, smooth muscle spasm; and/or that promotes smooth muscle relaxation. Such an inhibiting (or promoting in the case of smooth muscle relaxation) amount of the polypeptides that can be employed ranges generally between about 0.01 µg/kg body weight and about 10 mg/kg body weight, preferably ranging between about 0.05 µg/kg and about 5 mg/kg body weight.

The present invention may be better understood with reference to the accompanying examples that are intended for purposes of illustration only and should not be construed to limit the scope of the invention, as defined by the claims appended hereto.

EXAMPLES

Example 1

This Example illustrates a study of cyclic nucleotide-dependent phosphorylation of HSP20 in mesangial cells. The contractile phenotype and expression of PKG is lost as smooth muscle cells are passaged in culture. Mesangial cells have been shown to maintain a contractile phenotype in culture. To determine if mesangial cells in culture continue to express PKG and HSP20, multiply passaged mesangial cells were compared to multiply passaged vascular smooth muscle cells and smooth muscle cells that had been stably transfected with PKG. The cells were homogenized and immunoblots were performed using rabbit polyclonal antibodies against PKG and HSP20. Multiply passaged vascular smooth muscle cells did not express PKG or HSP20. However, smooth muscle cells that had been stably transfected with PKG express PKG and HSP20. Cultured mesangial cells expressed similar amounts of both PKG and HSP20 as the PKG transfected vascular smooth muscle cells. These data suggest that the expression of PKG and the PKG substrate protein, HSP20, are coordinately regulated and that the expression of these proteins may be important for maintaining the cells in a contractile phenotype. Since phenotypic modulation from a contractile to a synthetic phenotype has been implicated in the response to injury model of atherogenesis and in the development of intimal hyperplasia, we propose that introducing HSP20 either via protein transduction or by gene transfection will provide a novel therapeutic approach to maintain cells in a contractile phenotype and prevent intimal hyperplasia.

Example 2

This Example illustrates the production of the HSP20 S16A mutant wherein the phosphorylation site (serine 16) was mutated to an alanine. The cDNA for HSP20 was cloned into pEGFP-C2 expression vector (commercially available from Clontech, Inc.) For production of the HSP20 S16A mutant, a single nucleotide mutation was introduced in the HSP20 cDNA sequence using a two complimentary oligonucleotide strategy with Pfu polumerase (commercially available from Stratagene, La Jolla, Calif.). All sequences were confirmed for orientation, the presence of the appropriate mutations, and the absence of other mutations, using a 377 Perkin-Elmer ABI Prism DNA sequencer (Foster City, Calif.). Similar techniques can be used to mutate the serine 16 for an aspartic or glutamic acid.

Example 3

This experiment illustrates that genetic manipulation of muscle like cells can alter their ability to contract. Specifically, engineering the cells to overexpress HSP20 prevents them from contracting (going into a state of spasm). If the cells overexpress a mutated form of HSP20 that cannot be phosphorylated, they remain contracted (in spasm) even when treated with potent agents which cause relaxation. This experiment demonstrates that the phosphorylation of HSP20 is the seminal event required for muscles to relax.

The experiment was performed in the following fashion: Mesangial cells were transfected with vectors containing green fluorescent protein (GFP) alone, GFP fused to the 5' end of the wild type cDNA for HSP20 (WT), or GFP fused to an HSP20 construct in which the PKA phosphorylation site was mutated to an alanine (S16A-HSP20) (MUT). The cells were plated on a silicone rubber substrata in the presence of serum for 48 hours. The plates were then placed on the stage of a Zeiss Inverted Fluorescence Microscope with DeltaVision image acquisition and deconvolution software (Applied Precision, Issaquah, Wash.). The DeltaVision software was configured to eight different cells (x and y axis) on each plate with 7 z-axis images taken at 2 nm intervals. Fluorescent and phase contrast images were obtained such that the cells and silicone membrane were imaged in close succession. During the scanning process, the z-axis of each cell was monitored to assure that the imaging stacks were maintained at the appropriate level as the cells relaxed on the silicone membrane. Baseline images were acquired for one hour. The cells were then treated with the cells were treated with dibutyryl cAMP (10 ΦM) for 0 minutes, 30 minutes, 60 minutes, or 90 minutes, and the results are illustrated in FIG. 1.

The control cells expressing the green fluorescent protein (GFP) in which the HSP20 was not changed relaxed over time (the wrinkles under the cells disappeared) when treated with dibutyryl cAMP. The cells over expressing HSP20 tagged to GFP (WT) did not form wrinkles; they were unable to contract or go into spasm. The cells expressing the mutated form of HSP20 that could not be phosphorylated (S16A-HSP20) (MUT) formed abundant wrinkles (contracted) but did not relax (remained in spasm) in response to dibutyryl cAMP. This figure is representative of 6 separate transfections in which at least 12 cells were imaged with each construct and the aggregate data is illustrated graphically (*=p<0.05 compared to the initial number of wrinkles). Similar findings were observed when cyclic nucleotide-dependent signaling pathways were activated with sodium nitroprusside (10 μM), dibutyryl cGMP (10 μM), or forskolin (10 μM) (data not shown). There were no changes in the wrinkles in the substrata in untreated cells imaged for 90 minutes (data not shown). These data demonstrate that over expression of wild type HSP20 inhibits contraction of the cells and expression of the S16A-HSP20 mutated protein inhibits relaxation. Thus, these data show that the phosphorylation of HSP20 is necessary and sufficient for the relaxation of smooth muscles, and suggests that phosphorylation of HSP20 represents a point in which the cyclic nucleotide signaling pathways converge to prevent contraction or cause relaxation.

Example 4

Figure 2:
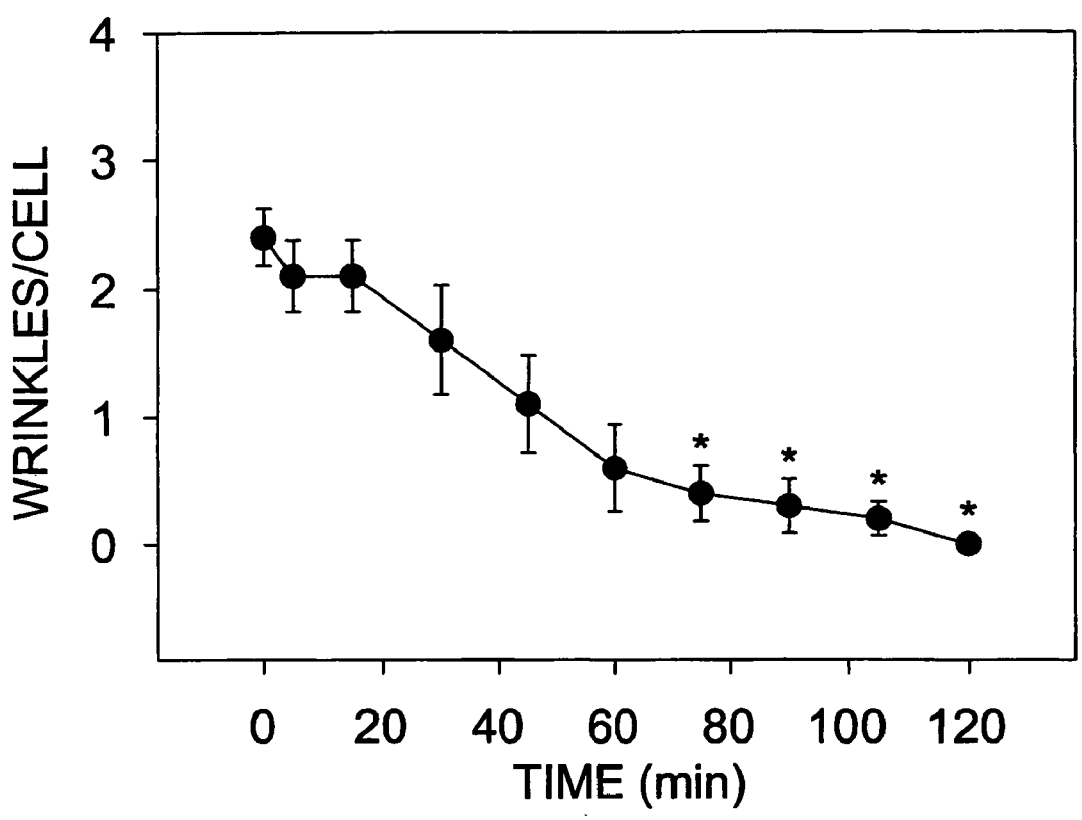
FIG. 2. Mesangial cells were transduced with FITC-TAT-HSP20 and the number of wrinkles under the cells was determined at the time points indicated using phase contrast microscopy (n=10, *=p<0.05 compared to time 0).

This experiment demonstrates that transduction of peptide analogues of phosphorylated HSP20 relaxes muscle-like cells. Phosphopeptide analogues of HSP20 were synthesized containing the TAT sequence (NH$_2$-βAGGGGYGRKKRRQRRRWLRRAS*APLPGLK-COOH) (referred to as FITC-TAT-HSP20) (SEQ ID NO:304) (the asterisk indicates that the "S" residue is phosphorylated). Mesangial cells were plated on a silicone substrata in the presence of serum and after 48 hours the cells were treated with the FITC-TAT-HSP20 phosphopeptide (50 μM). The number of wrinkles under the cells was determined at the time points indicated using phase contrast microscopy (n=10, *=p<0.05 compared to time 0). Results of this Experiment are illustrated in FIG. 2. Treatment of the cells with the phosphopeptide analogue of HSP20 led to a time dependent loss of wrinkles (relaxation of the cells). This experiment demonstrates that transduction of phosphopeptide analogues of HSP20 also relaxes the cells.

Example 5

This experiment demonstrates that transduction of phosphopeptide analogues of HSP20 relax and prevent spasm in intact strips of vascular smooth muscle. Transverse strips of bovine carotid artery smooth muscle, denuded of endothelium, were suspended in a muscle bath containing bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), equilibrated with 95% $O_2$/5% $CO_2$, at 37° C. at one gram of tension for 2 hours. The muscles were pre-contracted with serotonin (1 μM for 10 minutes) and cumulative doses of FITC-phosphoHSP20-TAT, FITC-scrambled phosphoHSP20-TAT (FITC-$NH_2$-βAGGGGYGRKKRRQRRRPRKS*LWALGRPLA-COOH, open circles) (SEQ ID NO:305), or FITC-TAT (FITC-$NH_2$-βAGGGGYGRKKRRQRRR, closed triangles) (SEQ ID NO:306) were added every 10 minutes. The force is depicted as a percentage of the maximal serotonin contraction (n=5, *=p<0.05 compared to 0 peptide added). Representative strips were fixed in 4% paraformaldehyde and examined under fluorescence microscopy (40× magnification). The internal elastic lamina (IEL) autofluoresced, and the media and adventitia (ADV) also displayed fluorescence(not shown).

Figure 3:
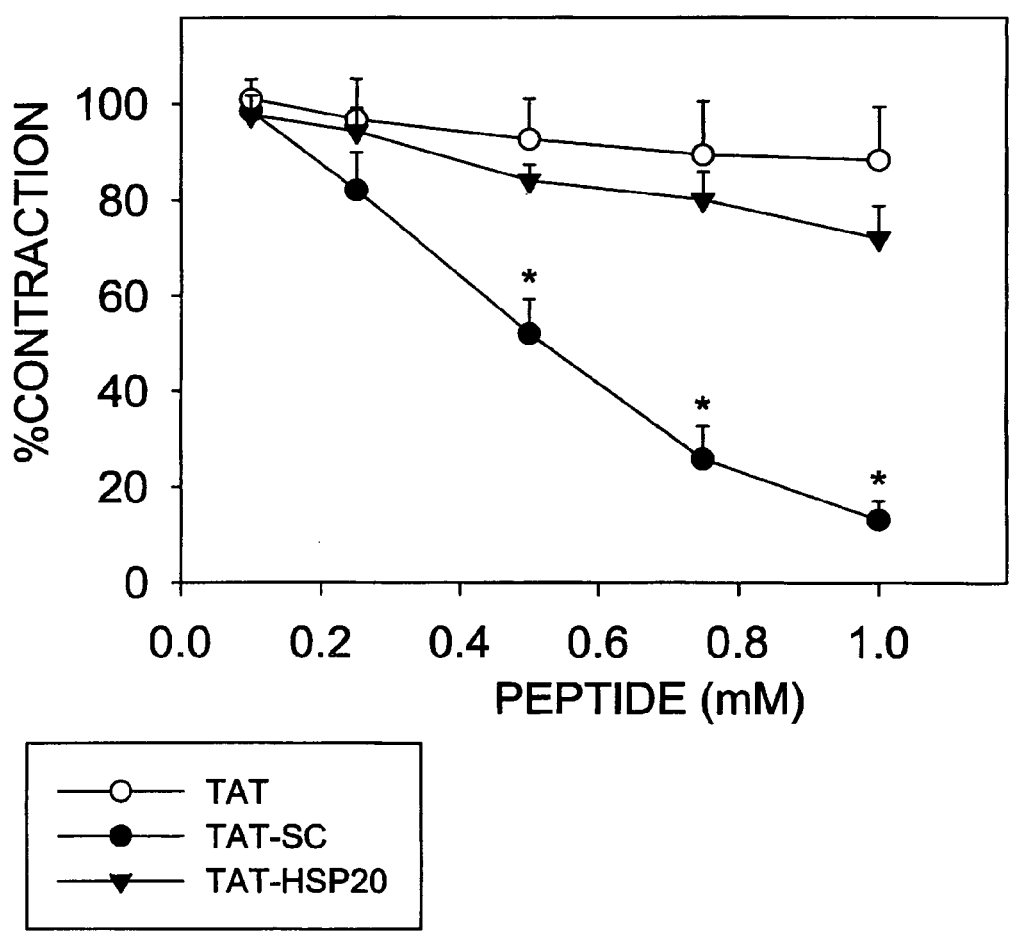
FIG. 3. Transverse strips of bovine carotid artery smooth muscle, denuded of endothelium, were pre-contracted with serotonin (1 μM for 10 minutes), cumulative doses of FITC-phospho-HSP20-TAT, FITC-scrambled phosphoHSP20-TAT (FITC-NH$_2$-βAGGGGYGRKKRRQRRRPRKS*LWALGRPLA-COOH, open circles) (SEQ ID NO:305), or FITC-TAT (FITC-NH$_2$-βAGGGGYGRKKRRQRRR, closed triangles) (SEQ ID NO:306) were added every 10 minutes, and the percent contraction was calculated. The force is depicted as a percentage of the maximal serotonin contraction(n=5, *=p<0.05 compared to 0 peptide added).

The results of this Experiment are illustrated in FIG. 3. Transduction of pre-contracted strips of intact bovine corotid artery smooth muscle with the FITC-TAT-HSP20 phosphopeptide led to a dose dependent decrease in serotonin pre-contracted muscles. Peptides containing the scrambled sequence or FITC-TAT alone had no significant effect on contractile force. This shows that the phosphopeptide analogues relax and prevent spasm in intact vascular smooth muscles. There was a diffuse fluorescence staining pattern of the muscle strips after transduction with the FITC-TAT-HSP20 phosphopeptide which shows that the peptides enter the muscles.

Example 6

This experiment shows that a different transducing peptide can introduce the HSP20 phosphopeptide analogues. In addition, it demonstrates that phosphopeptide analogues of HSP20 relax and prevent spasm in smooth muscles from a different vascular bed in a different species. Finally, it shows that transduction of HSP20 analogues relax and prevent spasm in muscles in which an intact endothelium is present.

Figure 4:
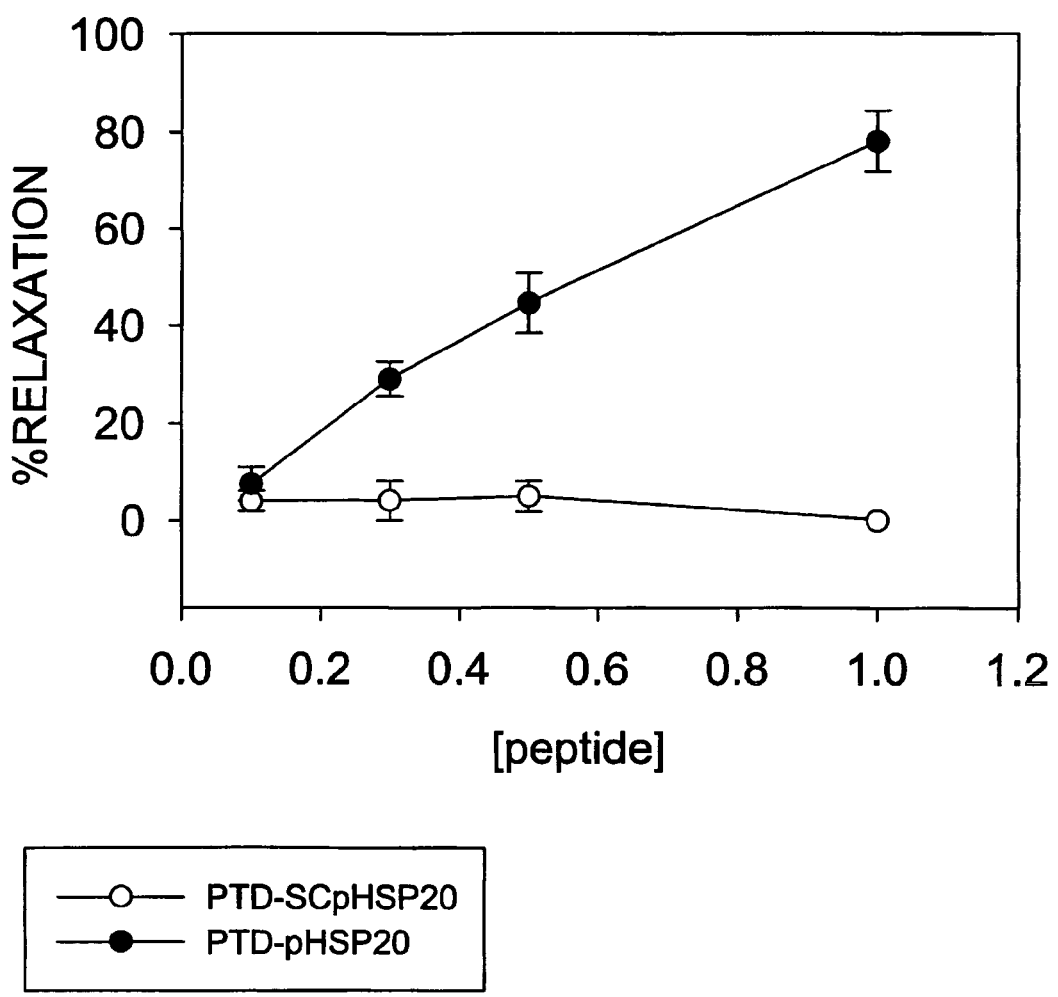
FIG. 4. Rings of porcine coronary artery in which the endothelium was not denuded, were pre-contracted with serotonin (1 μM for 10 minutes), cumulative doses of PTD-pHSP20 (NH$_2$-βAYARRAAARQARAWLRRAS*APLPGLK-COOH, closed circles) (SEQ ID NO:307) or PTD-scrambled-pHSP20 (NH$_2$-βAYARRAAARQARAPRKS*LWALGRPLA-COOH open circles) (SEQ ID NO:308) were added every 10 minutes, and the percentage of relaxation was calculated as a percentage of the maximal serotonin contraction (n=5, *=p<0.05 compared to 0 peptide added). The concentrations of peptide used are depicted on the x axis.

Rings of porcine coronary artery in which the endothelium was not denuded, were suspended in a muscle bath containing bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), equilibrated with 95% $O_2$/5% CO2, at 37° C. at one gram of tension for 2 hours. The muscles were pre-contracted with serotonin (1 μM for 10 minutes) and cumulative doses of PTD-pHSP20 ($NH_2$-βAYARRAAARQARAWLRRAS*APLPGLK-COOH, closed circles) (SEQ ID NO:307) or PTD-scrambled-pHSP20 ($NH_2$-βAYARRAAARQARAPRKS*LWALGRPLA-COOH open circles) (SEQ ID NO:308) were added every 10 minutes (FIG. 4). The percentage of relaxation is depicted as a percentage of the maximal serotonin contraction (n=5, *=p<0.05 compared to 0 peptide added). The concentrations of peptide used are depicted on the x axis. Representative rings were treated with peptides (1 mM final concentration) linked to FITC (15 minutes at 37° C.), fixed in 4% paraformaldehyde and examined under fluorescence microscopy (40× magnification).

The results of this experiment are illustrated in FIG. 4. This shows that phosphopeptide analogues of HSP20 relax and prevent spasm in muscles from a different species and different vascular bed. There was marked fluorescence in the strips treated with protein transduction analogues. This demonstrates that a protein transduction peptide that is different than TAT can transduce the phosphopeptide analogue and relax and prevent spasm in muscles.

Example 7

This experiment shows that protein transduction of phosphopeptide analogues of HSP20 can relax and prevent spasm in non-vascular smooth muscles.

The internal anal sphincter was obtained from a human pathology specimen after an abdominal perineal resection for cancer. The smooth muscles were equilibrated in a muscle bath as described in example 6. The muscles developed tonic sustained contractions when warmed in the bicarbonate buffer. These contractions relaxed with the addition of the guanylate cyclase activator, sodium nitroprusside (SNP). When the sodium nitroprusside was washed out of the bath, the muscles again contracted spontaneously. The muscles were then treated with the PTD-phosphopeptide analogues of $HSP_2$-($NH_2$-βAYARRAAARQARAWLRRAS*APLPGLK-COOH, 1 mM final concentration) (SEQ ID NO:307). The muscles relaxed and spasm was prevented in response to the phosphopeptide analogues and the relaxation was sustained.

Intestinal smooth muscle was obtained from the tinea coli of a pig. These muscles were equilibrated in a muscle bath as described in example 6. The muscles produced transient contractions in response to high extracellular potassium chloride (KCl 110 mM) and in response to carbachol ($10^{-6}$ M). The muscles were then treated with a dextran gel containing the PTD-phosphopeptide analogues of HSP20 ($NH_2$-βAYARRAAARQARAWLRRAS*APLPGLK-COOH, 1 mM final concentration) (SEQ ID NO:307) and treated with carbachol. Treatment with the phosphopeptide analogues significantly attenuated the contractile response to carbachol.

Tracheal and corpra cavernosal smooth muscles were obtained from a New Zealand White rabbits after sacrifice. The muscles were equilibrated in a muscle bath as described in example 6. The tracheal muscles were pre-contracted with carbachol and the corpra cavernosal smooth muscles were pre-contracted with norepinephrine. The muscles were then treated with the PTD-phosphopeptide analogues of HSP20 (NH2-βAYARRAAARQARAWLRRAS*APLPGLK-COOH) (SEQ ID NO:307). Both the tracheal and the corpra cavernosal muscles relaxed and spasm was prevented in response to the phosphopeptide analogues.

The results of these experiments show that the phosphopeptide analogues of HSP20 relax and prevent spasm in human anal sphincter smooth muscles, porcine intestinal smooth muscle, rabbit tracheal smooth muscles, and rabbit corpra cavernosal smooth muscles.

Example 8

This experiment shows that protein transduction of phosphopeptide analogues of HSP20 can relax and prevent spasm in human saphenous vein smooth muscles.

Human saphenous vein was obtained from remnants that were discarded after vascular bypass operations. Rings of the saphenous vein were equilibrated in a muscle bath as described in experiment 4. The rings were treated with a 7.5% dextran gel alone, or a 7.5% dextran gel containing the phosphopeptide analogues of HSP20 (NH$_2$-βAYARRAAARQARAWLRRAS*APLPGLK-COOH) (SEQ ID NO:307). The rings were then treated with serotonin (1 uM). The rings treated with the 7.5% dextran gel alone contracted in response to serotonin. However, the rings treated with the 7.5% dextran gel that contained the HSP20 phosphopeptide analogues did not contract in response to serotonin.

These results show that the phosphopeptide analogues of HSP20 prevent spasm (contraction) of human saphenous vein smooth muscles.

Example 9

This experiment was performed to demonstrate that smaller peptide analogues of phosphorylated HSP20 relax and prevent spasm of smooth muscles even more effectively than the larger analogues.

Rings of rabbit aorta in which the endothelium was not denuded, were suspended in a muscle bath containing bicarbonate buffer (120 mM NaCl, 4.7 mM KCl, 1.0 mM MgSO$_4$, 1.0 mM NaH$_2$PO$_4$, 10 mM glucose, 1.5 mM CaCl$_2$, and 25 mM Na$_2$HCO$_3$, pH 7.4), equilibrated with 95% O$_2$/5% CO$_2$, at 37° C. at one gram of tension for 2 hours. The rings were pre-contracted with norepinephrine ($10^{-7}$ M) and treated with RRRRRRApSAPLP (SEQ ID NO:309) or RRRRWLRRApSAPLP (SEQ ID NO:310). Both peptides caused rapid and complete relaxation and inhibition of spasm of the muscles, and the relaxation was faster and the muscles remained in a relaxed state for longer than when the longer peptides were used. The peptides used were prepared by Fmoc-based peptide synthesis, and the peptides retained the Fmoc moiety at the amino terminus of the peptide.

These data show that poly arginine sequences can transduce the HSP20 analogues and induce relaxation and that the smaller sequence ApSAPLP (SEQ ID NO:3) (where "p" indicates that the S residue is phosphorylated) causes rapid and complete relaxation and inhibition of spasm.

Example 10

This experiment illustrates that HSP20 is expressed in mesangial cells and in rat aortic smooth muscle cells that have been stably transfected with PKG. It also illustrates that relaxation of mesangial cells is associated with increases in the phosphorylation of HSP20.

Figure 5A:
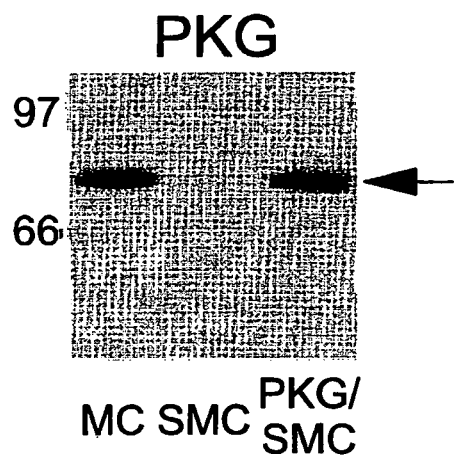
FIG. 5. Homogenates of mesangial cells (lane 1), rat aortic smooth muscle cells (lane 2), and PKG transfected rat aortic smooth muscle cells (lane 3) were immunoblotted for PKG (panel A) or HSP20 (panel B). In a separate experiment, mesangial cells were untreated (panel C) or treated with dibutyryl cAMP (10 μM, 15 minutes, panel D). The proteins were separated by 2-dimensional electrophoresis, transferred to immobilon and probed with anti-HSP20 antibodies. Increases in the phosphorylation of HSP20 leads to a shift in the electrophoretic mobility of the protein to a more acidic isoform (arrow).
Figure 5B:
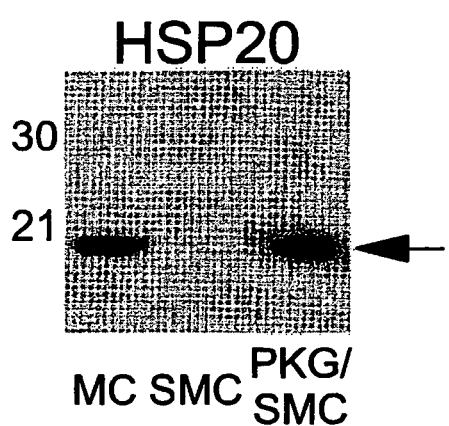
Figure 5C:
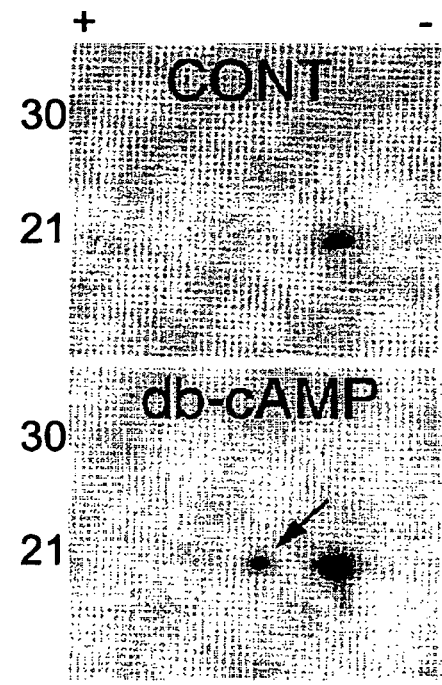

Homogenates of mesangial cells (FIG. 5, lane 1), rat aortic smooth muscle cells (FIG. 5, lane 2), and PKG transfected rat aortic smooth muscle cells (FIG. 5, lane 3) were immunoblotted for PKG (FIG. 5, panel A) or HSP20 (FIG. 5, panel B). In a separate experiment, mesangial cells were untreated (FIG. 5, panel C) or treated with dibutyryl cAMP (10 μM, 15 minutes, FIG. 5, panel D). The proteins were separated by 2-dimensional electrophoresis, transferred to immobilon and probed with anti-HSP20 antibodies. Increases in the phosphorylation of HSP20 lead to a shift in the electrophoretic mobility of the protein to a more acidic isoform (arrow).

These data show that activation of cyclic nucleotide-dependent signaling pathways in mesangial cells (as shown in FIG. 2) is associated with phosphorylation of HSP20.

Example 11

This experiment illustrates that cells expressing HSP20 (stably PKG transfected cells) are able to contract.

Rat aortic smooth muscle cells that are multiply passaged or that stably express PKG were cultured on a silicone substrata in the presence of serum. The cells were imaged with phase contrast microscopy (10×magnification). The multiply passaged cells did not form wrinkles on the substrata whereas the PKG transfected cells formed wrinkles. To determine if the wrinkles were reversible, PKG transfected cells were treated with dibutyryl cAMP (10 uM) for 30 minutes. Dibutyryl cAMP led to a decrease in wrinkle formation.

Taken together with example 10, these results show that the expression of HSP20 is associated with a contractile phenotype. Vascular smooth muscle cells exist in widely divergent phenotypes. In the normal vessel wall, the smooth muscle cells are in a well differentiated contractile phenotype and are capable of generating force. In response to injury, or cell culture conditions, the cells modulate to a synthetic or secretory phenotype. These cells proliferate and secrete matrix proteins contributing to intimal hyperplasia. Phenotypic modulation is associated with changes in gene expression, protein expression, morphology, and physiologic responses. This leads to pathologic narrowing of the vessel lumen which occurs in atherosclerosis and intimal hyperplasia. This leads to stenotic lesions and ultimately occlusion of the vessel. Thus, maintaining expression of HSP20 is important for the maintenance of the contractile phenotype.

Example 12

Cellular processes such as cell adhesion, cytokinesis, cell motility, migration, and contraction all require dynamic reorganization of the actin cytoskeleton These experiments show that the phosphorylation of HSP20 modulates changes in these actin filaments.

Figure 6:
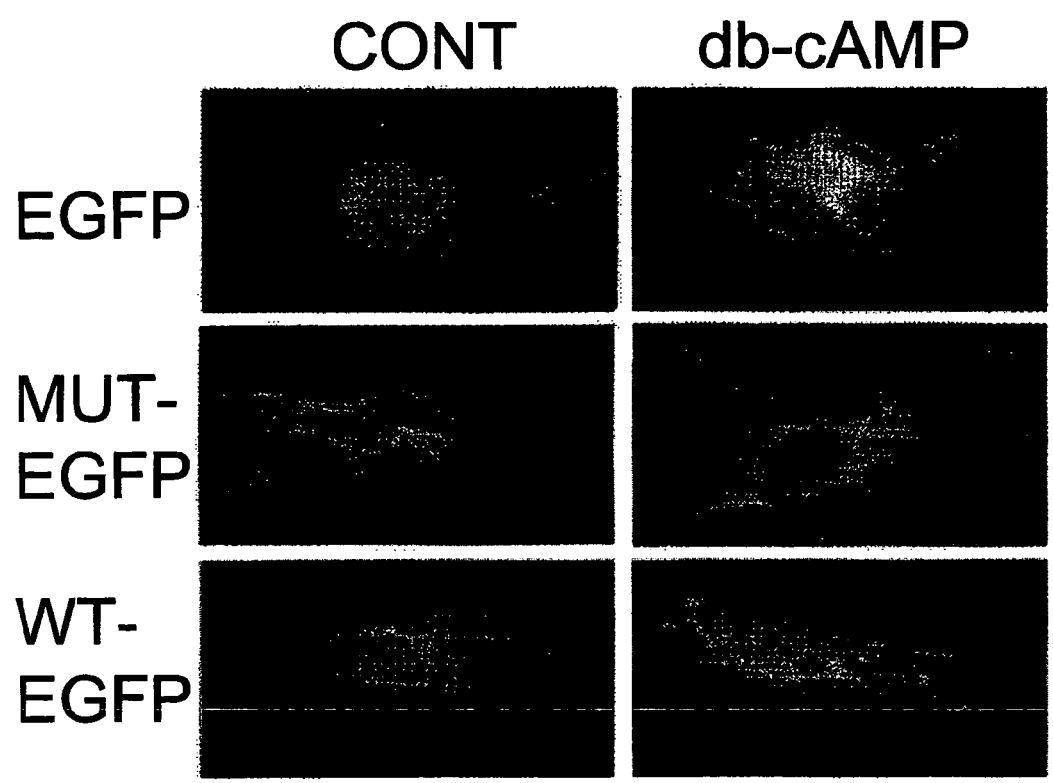
FIG. 6. Transfected mesangial cells were fixed, and the actin filaments were stained with fluorescent-labeled phalloidin. Mesangial cells were transfected with EGFP alone (EGFP), S16A-HSP20 (MUT-EGFP), or wild type HSP20 (WT-EGFP). The cells were plated on a glass slides, and not treated (CONT) or treated with dibutyryl cAMP (10 μM, for 30 minutes, db-cAMP). The cells were fixed and stained with rhodamine phalloidin. Dibutyryl cAMP led to a loss of central actin stress fibers in EGFP but not S16A-HSP20 cells. In the cells overexpressing HSP20 the actin fibers were peripherally localized.

Transfected mesangial cells were fixed and the actin filaments were stained with fluorescent-labeled phalloidin. Mesangial cells were transfected with EGFP alone (EGFP), S16A-HSP20 (MUT-EGFP, or wild type HSP20 (WT-EGFP). The cells were plated on a glass slides, and not treated (CONT) or treated with dibutyryl cAMP (10 μM, for 30 minutes, db-cAMP). The cells were fixed and stained with rhodamine phalloidin. Dibutyryl cAMP led to a loss of central actin stress fibers in EGFP but not S 16A-HSP20 cells. In the cells overexpressing HSP20 the actin fibers were peripherally localized. The results of this experiment are illustrated in FIG. 6.

These experiments show that activation of cyclic nucleotide-dependent signaling pathways, which lead to increases in the phosphorylation of HSP20, are associated with a loss of central actin stress fibers. Over-expression of HSP20 was also associated with a loss of actin stress fibers. In cells overexpressing a mutated form of HSP20 in which the serine has been replaced with an alanine (S16A-HSP20) and cannot be phosphorylated, there is no loss of these central actin fibers with activation of cyclic nucleotide-dependent signaling pathways. These studies demonstrate that phosphorylation of HSP20 is associated with changes in actin fiber formation.

Example 13

This experiment shows that protein transduction of smooth muscle cells with phosphopeptide analogues of HSP20 also leads to changes in actin fiber formation.

Rat aortic smooth muscle cells were treated with lyophosphatidic acid (LPA) in the presence and absence of FITC-TAT-pHSP20 (FITC-NH$_2$-βAGGGGYGRKKRRQRRRWLRRAS*APLPGLK-COOH, 50 uM) (SEQ ID NO:307) Lysophosphatidic acid (LPA) is a substance which promotes actin fiber formation. Inhibition of the actions of LPA have been shown to inhibit intimal hyperplasia.

The cells were fixed and stained with phalloidin and images were obtained with confocal microscopy. LPA led to robust actin stress fiber formation, whereas there was a loss of central actin stress fibers in the cells treated with LPA in the presence of the FITC-TAT-pHSP20 peptide. These studies show that protein transduction with the phosphopeptide analogues of HSP20 inhibit LPA-induced actin fiber formation. These studies confirm that HSP20 has a direct role in modulating actin fiber formation.

Example 14

Cell adhesion formation involves the interaction between integrins and extracellular matrix substrates. This induces integrin clustering. The cells then form actin microfilaments and the cells spread. If the appropriate signals are provided by the matrix, the cells proceed to organize their cytoskeleton as characterized by the formation of focal adhesions and actin-containing stress fibers. Cell adhesion is a dynamic reversible process integral to cell migration. Activation of cGMP leads to focal adhesion disassembly. These studies show that phosphopeptide analogues of HSP20 mediate focal adhesion disassembly.

Figure 7:
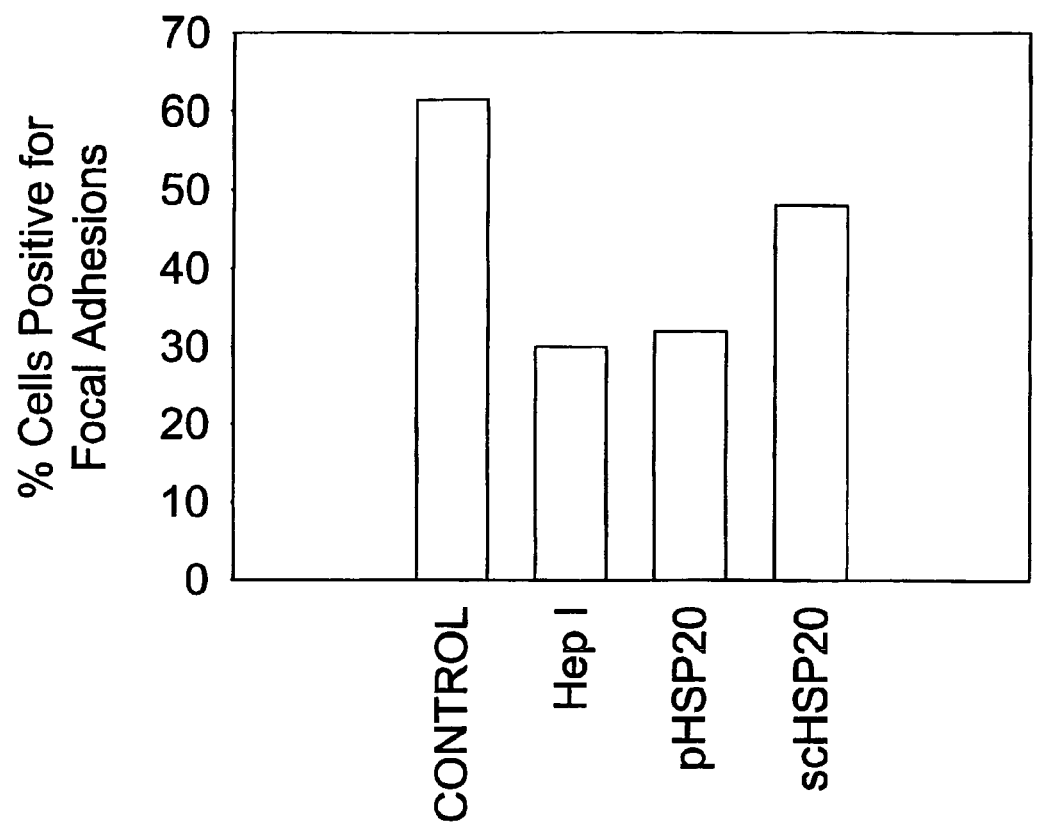
FIG. 7. Bovine aortic endothelial cells were plated on glass coverslips (80K-100K cells) in DMEM plus 10% FBS over night (24 wells plate). The cells were serum starved (no serum) for one hour and incubated in the presence of the peptide analogues of HSP20 [NH$_2$-βAYARRAAARQARAWLRRAS*APLPGLK-COOH-pHSP20 (10 uM) (SEQ ID NO:307) or scrambled analogues of HSP20 [NH$_2$-βAYARRAAARQARAPRKS*LWALGRPLA-COOH-scHSP20 (10 uM)] (SEQ ID NO:308) for 30 minutes. The cells were fixed with 3% glutaraldehyde and the number of focal adhesions was detected with interference reflection microscopy. The Hep I peptide was used as a positive control.

Bovine aortic endothelial cells were plated on glass coverslips (80K-100K cells) in DMEM plus 10% FBS over night (24 wells plate). The cells were serum starved (no serum) for one hour and incubated in the presence of the peptide analogues of HSP20 [NH$_2$-βAYARRAAARQARAWLRRAS*APLPGLK-COOH-pHSP20 (10 uM) (SEQ ID NO:307) or scrambled analogues of HSP20 [NH$_2$-βAYARRAAARQARAPRKS*LWALGRPLA-COOH-scHSP20 (10 uM)] (SEQ ID NO:308) for 30 minutes. The cells were fixed with 3% glutaraldehyde and the number of focal adhesions was detected with interference reflection microscopy. The Hep I peptide was used as a positive control. This peptide binds to the heparin binding site of thrombospondin in induces focal adhesion disassembly. Both Hep I and pHSP20 led to focal adhesion disassembly. The results are illustrated in FIG. 7.

Treatment with PTD-pHSP20 led to a disassociation of focal adhesions similar to the disassociation induced by a peptide from the amino-terminal heparin-binding domain of thrombospondin 1 (Hep 1). The scrambled peptide had no significant effect on focal adhesion disassembly. These studies show that phosphorylated HSP20 mediates focal adhesion disassembly. This weakens cell attachment and prevents the formation of the attachments necessary for cell migration.

Example 15

This Experiment shows that the phosphorylated peptide analogues of HSP20 directly inhibit cell migration.

Figure 8A:
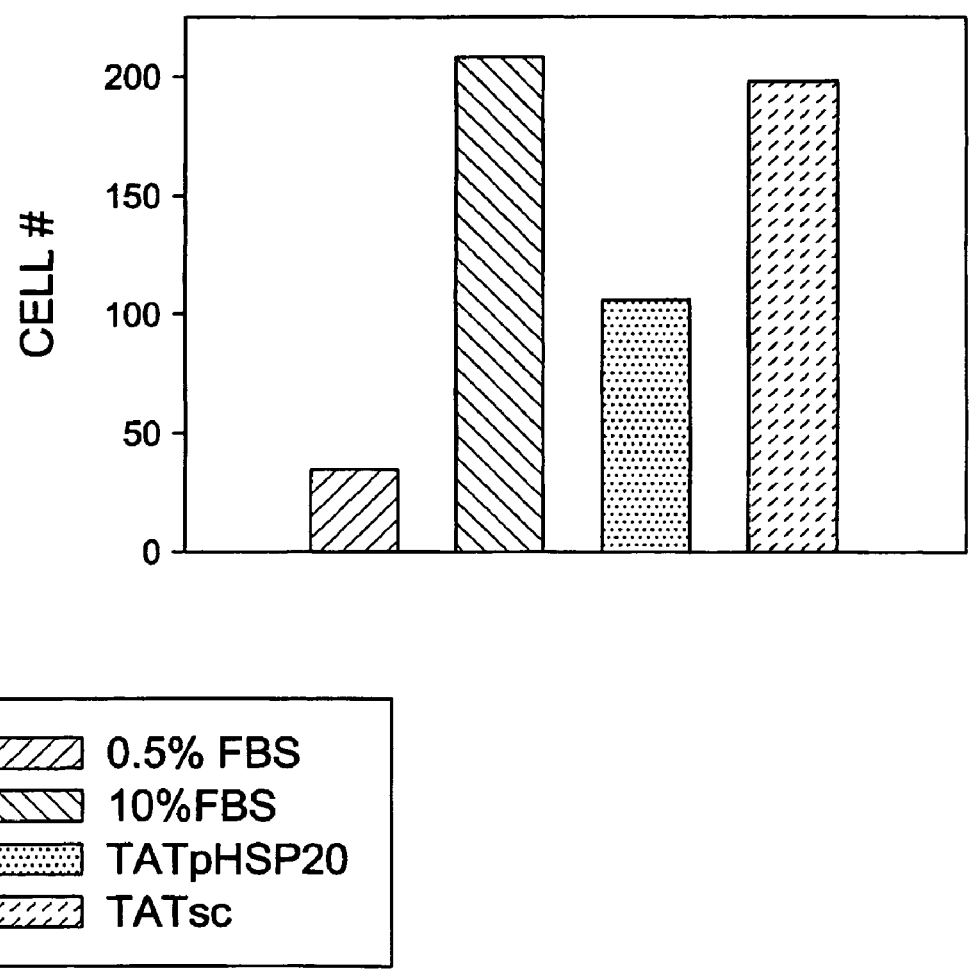
FIG. 8. Confluent A10 cells were serum starved (0.5% fetal bovine serum, FBS) for 48 hours. A linear wound was made in the smooth muscle cell monolayer using a rubber scraper and the scratched edges were marked using metal pins. The cells were changed to 10% FBS media containing PTD-pHSP20 (NH$_2$-βAYARRAAARQARAWLRRAS*APLPGLK-COOH (SEQ ID NO:307), or PTD-scrambled-pHSP20 (NH$_2$-βAYARRAAARQARAPRKS*LWALGRPLA-COOH (SEQ ID NO:308) (50 μM) and incubated for 24 hours. The cells were fixed and stained with hematoxylin. The number of cells migrating into a 1 cm$^2$ scratched area were counted as an index for migration. In additional experiments, the migration of A10 cells was determined in a Boyden chamber assay.
Figure 8B:
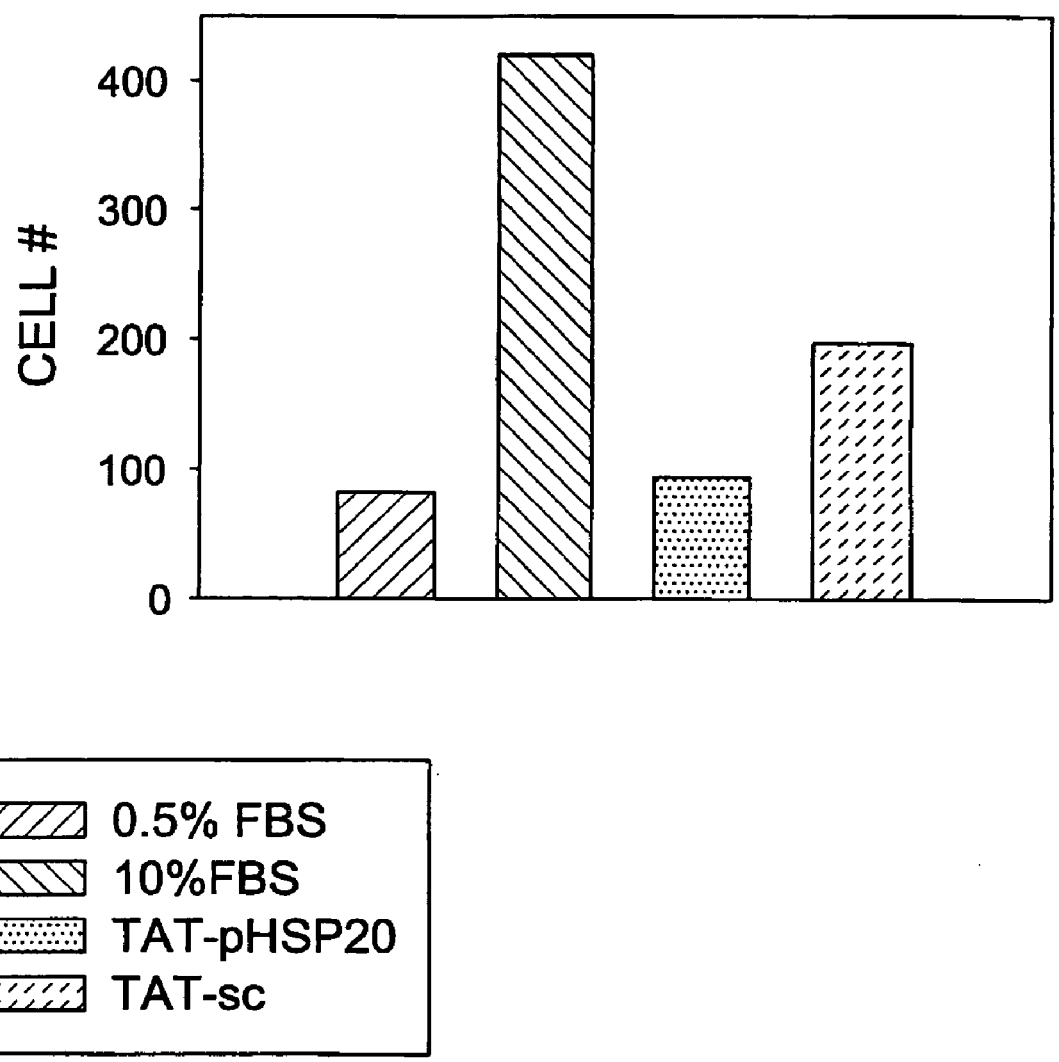

Confluent A10 cells were serum starved (0.5% fetal bovine serum, FBS) for 48 hours. A linear wound was made in the smooth muscle cell monolayer using a rubber scraper and the scratched edges were marked using metal pins. The cells were changed to 10% FBS media containing PTD-pHSP20 (NH$_2$-βAYARRAAARQARAWLRRAS*APLPGLK-COOH (SEQ ID NO:307), or PTD-scrambled-pHSP20 (NH$_2$-βAYARRAAARQARAPRKS*LWALGRPLA-COOH (SEQ ID NO:308) (50 μM) and incubated for 24 hours. The cells were fixed and stained with hematoxylin. The number of cells migrating into a 1 cm$^2$ scratched area were counted as an index for migration. In additional experiments, the migration of A10 cells was determined in a Boyden chamber assay. In both cases the phosphopeptide analogue of HSP20 led to inhibition of migration. FIG. 8 illustrates the results of these experiments.

These results show that transduction of phosphopeptide analogues of HSP20 inhibits serum-induced migration of smooth muscle cells.

Example 16

This experiment shows that transduction of phosphopeptide analogues of HSP20 inhibits serum-induced proliferation of smooth muscle cells.

Figure 9:
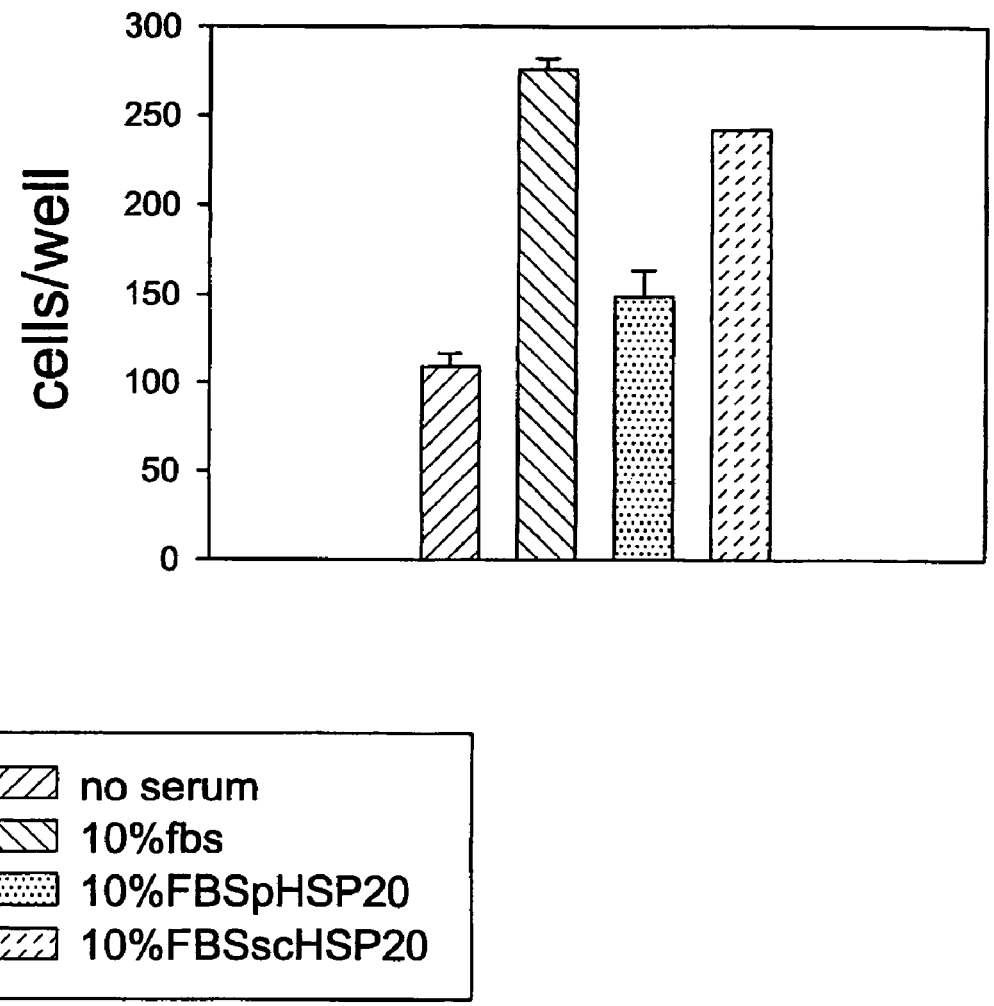
FIG. 9. A10 cells were serum starved for 3 days. The cells were then treated with media containing 10% fetal bovine serum, PTD-pHSP20 (NH$_2$-βAYARRAAARQARAWLRRAS*APLPGLK-COOH (SEQ ID NO:307), or PTD-scrambled-pHSP20 (NH$_2$-βAYARRAAARQARAPRKS*LWALGRPLA-COOH (SEQ ID NO:308) (50 μM). After 24 hours cell counts were performed.

A10 cells were serum starved for 3 days. The cells were then treated with media containing 10% fetal bovine serum, PTD-pHSP20 (NH$_2$-βAYARRAAARQARAWLRRAS*APLPGLK-COOH (SEQ ID NO:307), or PTD-scrambled-pHSP20 (NH$_2$-βAYARRAAARQARAPRKS*LWALGRPLA-COOH (SEQ ID NO:308) (50 μM). After 24 hours cell counts were performed. The number of cells per well in the serum starved plates averaged 109 cells/well (+/-7.4) compared to 276+/-6.1 in wells containing 10% fetal bovine serum (FBS). In the presence of FBS, the phosphopeptide analogues of HSP20 containing a transduction domain inhibited of smooth muscle proliferation, 149+/-14.6 compared to transduction of the scrambled phosphopeptide analogue of HSP20 (242.3+/-15.3 cells/well). The results of these experiments are illustrated in FIG. 9.

The results from these examples demonstrate that HSP20 is associated with a contractile phenotype and that transduction of phosphopeptide analogues of HSP20 inhibit actin fiber formation, focal adhesion formation, smooth muscle cell migration and smooth muscle proliferation. These are cellular processes that lead to intimal hyperplasia, and other disorders as discussed throughout the application.

Example 17

These experiments show that HSP20 inhibits intimal hyperplasia in human saphenous vein grafts.

Segments of human saphenous vein were cultured in media containing 30% fetal bovine serum. The segments were treated for 14 days with media containing serum alone, serum and the phosphopeptide analogue of HSP20 (PTD-pHSP20 (NH$_2$-βAYARRAAARQARAWLRRAS*APLPGLK-COOH, 10 :M) (SEQ ID NO:307), or the PTD-scrambled phosphopeptide analogue (NH$_2$-βAYARRAAARQARAPRKS*LWALGRPLA-COOH, 10 : μM). (SEQ ID NO:308) The rings were fixed in formalin, stained with hematoxylin and eosin, and the intimal area was measured morphometrically. There was a significant reduction in intimal area in the rings transduced with the phosphopeptide analogues of HSP20 compared to the rings treated with serum alone or serum and transduction of the scrambled analogue.

These results show that intimal hyperplasia can be inhibited in human saphenous vein segments by transduction of the phosphopeptide analogues of HSP20.

Example 18

This Experiment illustrates that plant cells can be engineered to produce recombinant HSP20.

Tobacco BY-2 cells were transformed with vector alone (vector transformed) or with His tagged HSP20 constructs (6Xhis-HSP20 transformed). Western blots were performed on cells lysates using anti-6Xhis monoclonal antibodies. There is immunoreactivity of a 20 kDa polypeptide in the HSP20 lysates but not the empty vector transformed lysates.

Optical sections from confocal immunofluorescence images of processed tobacco cells transiently-expressing either myc-epitope tagged HSP20, probed with anti-myc antibodies, HSP20, probed with anti-HSP20 antibodies, TAT-HSP20, probed with anti-HSP20 antibodies, or HISTAT-HSP20, probed with anti-his antibodies. Expression is present with all 4 constructs (bar=100 μm).

These data show that plants can be engineered to produce proteins that contain a protein transduction sequence and the HSP20 molecule. This represents an alternative source of production of HSP20.

We claim:

1. An isolated polypeptide consisting of a sequence according to general formula I:

X2-[X3-A(X4)APLP-X5-]-X6

Wherein X2 is absent or comprises a transduction domain, wherein the transduction domain comprises a polypeptide;
X3 is WLRR (SEQ ID NO:1);
X4 is selected from the group consisting of S, T, Y, D, E, phosphoserine analogs and phosphotyrosine analogs;
X5 is 0, 1, 2, or 3 amino acids of a sequence of genus Z1-Z2-Z3,
wherein Z1 is selected from the group consisting of G and D;
Z2 is selected from the group consisting of L and K; and
Z3 is selected from the group consisting of S and T;
X6 is absent or comprises a transduction domain, wherein the transduction domain comprises a polypeptide; and
wherein either X2 or X6 comprises a transduction domain.

2. The isolated polypeptide of claim 1 wherein X4 is phosphorylated.

3. A pharmaceutical composition, comprising one or more isolated polypeptides according to claim 1, and a pharmaceutically acceptable carrier.

4. An improved biomedical device, wherein the biomedical device comprises one or more isolated polypeptides according to claim 1 disposed on or in the biomedical device.

5. A composition comprising:
(a) an isolated polypeptide according to claim 1; and
(b) an inhibitor of HSP27.

6. An isolated polypeptide comprising a sequence according to the formula X2-SEQ ID NO:300-X6,
wherein X2 is absent or comprises a cell transduction domain, wherein the transduction domain comprises a polypeptide; and
X6 is absent or comprises a cell transduction domain, wherein the transduction domain comprises a polypeptide; and
wherein at least one of X2 and X6 comprise a transduction domain.

7. A pharmaceutical composition comprising the isolated polypeptide of claim 6 and a pharmaceutically acceptable carrier.

8. The isolated polypeptide of claim 2 wherein X4 is S.

9. The isolated polypeptide of claim 6 wherein X2 comprises a transduction domain.

10. The isolated polypeptide of claim 6 wherein the serine residue in SEQ ID NO:300 is phosphorylated.

11. A composition comprising:
(a) an isolated polypeptide according to claim 6; and
(b) an inhibitor of HSP27.

12. A pharmaceutical composition comprising the isolated polypeptide of claim 10 and a pharmaceutically acceptable carrier.

13. A composition comprising:
(a) an isolated polypeptide according to claim 10; and
(b) an inhibitor of HSP27.

14. The improved biomedical device of claim 13, wherein the biomedical device is selected from the group consisting of stents, grafts, shunts, stent grafts, fistulas, angioplasty devices, balloon catheters, and implantable drug delivery devices.

15. A composition comprising:
(a) an isolated polypeptide according to claim 8; and
(b) an inhibitor of HSP27.

16. A composition comprising the isolated polypeptide of claim 10 and a pharmaceutically acceptable carrier.

17. A composition comprising:
(a) an isolated polypeptide according to claim 10; and
(b) an inhibitor of HSP27.

18. A composition comprising an isolated polypeptide according to claim 1 and a heparin-containing gel.

19. A composition comprising an isolated polypeptide according to claim 9 and a heparin-containing gel.

20. A composition comprising an isolated polypeptide according to claim 6 and a heparin-containing gel.

21. A composition comprising an isolated polypeptide according to claim 10 and a heparin-containing gel.

22. The isolated polypeptide of claim 9 wherein the serine residue in SEQ ID NO:300 is phosphorylated.

23. A pharmaceutical composition, comprising the isolated polypeptide of claim 22, and a pharmaceutically acceptable carrier.

24. An improved biomedical device, wherein the biomedical device comprises the isolated polypeptide of claim 22 disposed on or in the biomedical device.

25. The improved biomedical device of claim 24, wherein the biomedical device is selected from the group consisting of stents, grafts, shunts, stent grafts, fistulas, angioplasty devices, balloon catheters, and implantable drug delivery devices.

26. A composition comprising the isolated polypeptide of claim 22 and a heparin-containing gel.

27. A composition comprising:
(a) the isolated polypeptide of claim 22; and
(b) an inhibitor of HSP27.

28. The isolated polypeptide of claim 8 wherein X2 comprises a transduction domain.

29. A pharmaceutical composition, comprising the isolated polypeptide of claim 28, and a pharmaceutically acceptable carrier.

30. An improved biomedical device, wherein the biomedical device comprises the isolated polypeptide of claim 28 disposed on or in the biomedical device.

31. The improved biomedical device of claim 30, wherein the biomedical device is selected from the group consisting of stents, grafts, shunts, stent grafts, fistulas, angioplasty devices, balloon catheters, and implantable drug delivery devices.

32. A composition comprising the isolated polypeptide of claim 28 and a heparin-containing gel.

33. A composition comprising:
(a) the isolated polypeptide of claim 28; and
(b) an inhibitor of HSP27.

* * * * *

SEQUENCE LISTING

```
<160> NUMBER OF SEQ ID NOS: 320

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Trp Leu Arg Arg
1

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is S, T, Y, D or E

<400> SEQUENCE: 2

Ala Xaa Ala Pro Leu Pro
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

Ala Ser Ala Pro Leu Pro
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Ala Thr Ala Pro Leu Pro
1               5
```

```
<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Arg Ala Ser Ala Pro Leu Pro
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic peptide

<400> SEQUENCE: 6

Arg Ala Thr Ala Pro Leu Pro
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Ala Tyr Ala Pro Leu Pro
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic peptide

<400> SEQUENCE: 8

Arg Ala Tyr Ala Pro Leu Pro
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Arg Arg Ala Ser Ala Pro Leu Pro
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic peptide

<400> SEQUENCE: 10

Leu Arg Arg Ala Ser Ala Pro Leu Pro
1               5
```

<210> SEQ ID NO 11
<211> LENGTH: 10
<212> TYPE: PRT
<213> ORGANISM: Artificial sequence
<220> FEATURE:
<223> OTHER INFORMATION: Synthetic peptide

<400> SEQUENCE: 11

Trp Leu Arg Arg Ala Ser Ala Pro Leu Pro
1               5                   10

<210> SEQ ID NO 12
<211> LENGTH: 8
<212> TYPE: PRT
<213> ORGANISM: Artificial sequence
<220> FEATURE:
<223> OTHER INFORMATION: Synthetic peptide

<400> SEQUENCE: 12

Arg Arg Ala Thr Ala Pro Leu Pro
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic peptide

<400> SEQUENCE: 13

Leu Arg Arg Ala Thr Ala Pro Leu Pro
1               5

<210> SEQ ID NO 14
<211> LENGTH: 10
<212> TYPE: PRT
<213> ORGANISM: Artificial sequence
<220> FEATURE:
<223> OTHER INFORMATION: Synthetic peptide

<400> SEQUENCE: 14

Trp Leu Arg Arg Ala Thr Ala Pro Leu Pro
1               5                   10

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Arg Arg Ala Tyr Ala Pro Leu Pro
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Leu Arg Arg Ala Tyr Ala Pro Leu Pro
1               5

<210> SEQ ID NO 17

```
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Trp Leu Arg Arg Ala Tyr Ala Pro Leu Pro
1               5                   10

<210> SEQ ID NO 18
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Arg Arg Ala Ser Ala Pro Leu Pro Gly
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Arg Arg Ala Ser Ala Pro Leu Pro Asp
1               5

<210> SEQ ID NO 20
<211> LENGTH: 10
<212> TYPE: PRT
<213> ORGANISM: Artificial sequence
<220> FEATURE:
<223> OTHER INFORMATION: Synthetic peptide

<400> SEQUENCE: 20

Arg Arg Ala Ser Ala Pro Leu Pro Gly Leu
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic peptide

<400> SEQUENCE: 21

Arg Arg Ala Ser Ala Pro Leu Pro Gly Lys
1               5                   10

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Arg Arg Ala Ser Ala Pro Leu Pro Asp Leu
1               5                   10

<210> SEQ ID NO 23
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 23

Arg Arg Ala Ser Ala Pro Leu Pro Asp Lys
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic peptide

<400> SEQUENCE: 24

Arg Arg Ala Ser Ala Pro Leu Pro Gly Leu Ser
1               5                   10

<210> SEQ ID NO 25
<211> LENGTH: 11
<212> TYPE: PRT
<213> ORGANISM: Artificial sequence
<220> FEATURE:
<223> OTHER INFORMATION: Synthetic peptide

<400> SEQUENCE: 25

Arg Arg Ala Ser Ala Pro Leu Pro Gly Leu Thr
1               5                   10

<210> SEQ ID NO 26
<211> LENGTH: 11
<212> TYPE: PRT
<213> ORGANISM: Artificial sequence
<220> FEATURE:
<223> OTHER INFORMATION: Synthetic peptide

<400> SEQUENCE: 26

Arg Arg Ala Ser Ala Pro Leu Pro Gly Lys Ser
1               5                   10

<210> SEQ ID NO 27
<211> LENGTH: 11
<212> TYPE: PRT
<213> ORGANISM: Artificial sequence
<220> FEATURE:
<223> OTHER INFORMATION: Synthetic peptide

<400> SEQUENCE: 27

Arg Arg Ala Ser Ala Pro Leu Pro Gly Lys Thr
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic peptide

<400> SEQUENCE: 28

Arg Arg Ala Ser Ala Pro Leu Pro Asp Leu Ser
1               5                   10

<210> SEQ ID NO 29
<211> LENGTH: 11
<212> TYPE: PRT
```

```
<213> ORGANISM: Artificial sequence
<220> FEATURE:
<223> OTHER INFORMATION: Synthetic peptide

<400> SEQUENCE: 29

Arg Arg Ala Ser Ala Pro Leu Pro Asp Leu Thr
1               5                   10

<210> SEQ ID NO 30
<211> LENGTH: 11
<212> TYPE: PRT
<213> ORGANISM: Artificial sequence
<220> FEATURE:
<223> OTHER INFORMATION: Synthetic peptide

<400> SEQUENCE: 30

Arg Arg Ala Ser Ala Pro Leu Pro Asp Lys Ser
1               5                   10

<210> SEQ ID NO 31
<211> LENGTH: 11
<212> TYPE: PRT
<213> ORGANISM: Artificial sequence
<220> FEATURE:
<223> OTHER INFORMATION: Synthetic peptide

<400> SEQUENCE: 31

Arg Arg Ala Ser Ala Pro Leu Pro Asp Lys Thr
1               5                   10

<210> SEQ ID NO 32
<211> LENGTH: 10
<212> TYPE: PRT
<213> ORGANISM: Artificial sequence
<220> FEATURE:
<223> OTHER INFORMATION: Synthetic peptide

<400> SEQUENCE: 32

Leu Arg Arg Ala Ser Ala Pro Leu Pro Gly
1               5                   10

<210> SEQ ID NO 33
<211> LENGTH: 10
<212> TYPE: PRT
<213> ORGANISM: Artificial sequence
<220> FEATURE:
<223> OTHER INFORMATION: Synthetic peptide

<400> SEQUENCE: 33

Leu Arg Arg Ala Ser Ala Pro Leu Pro Asp
1               5                   10

<210> SEQ ID NO 34
<211> LENGTH: 11
<212> TYPE: PRT
<213> ORGANISM: Artificial sequence
<220> FEATURE:
<223> OTHER INFORMATION: Synthetic peptide

<400> SEQUENCE: 34

Leu Arg Arg Ala Ser Ala Pro Leu Pro Gly Leu
1               5                   10

<210> SEQ ID NO 35
<211> LENGTH: 11
<212> TYPE: PRT
<213> ORGANISM: Artificial sequence
```

<220> FEATURE:
<223> OTHER INFORMATION: Synthetic peptide

<400> SEQUENCE: 35

Leu Arg Arg Ala Ser Ala Pro Leu Pro Gly Lys
1               5                   10

<210> SEQ ID NO 36
<211> LENGTH: 11
<212> TYPE: PRT
<213> ORGANISM: Artificial sequence
<220> FEATURE:
<223> OTHER INFORMATION: Synthetic peptide

<400> SEQUENCE: 36

Leu Arg Arg Ala Ser Ala Pro Leu Pro Asp Leu
1               5                   10

<210> SEQ ID NO 37
<211> LENGTH: 11
<212> TYPE: PRT
<213> ORGANISM: Artificial sequence
<220> FEATURE:
<223> OTHER INFORMATION: Synthetic peptide

<400> SEQUENCE: 37

Leu Arg Arg Ala Ser Ala Pro Leu Pro Asp Lys
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic peptide

<400> SEQUENCE: 38

Leu Arg Arg Ala Ser Ala Pro Leu Pro Gly Leu Ser
1               5                   10

<210> SEQ ID NO 39
<211> LENGTH: 12
<212> TYPE: PRT
<213> ORGANISM: Artificial sequence
<220> FEATURE:
<223> OTHER INFORMATION: Synthetic peptide

<400> SEQUENCE: 39

Leu Arg Arg Ala Ser Ala Pro Leu Pro Gly Leu Thr
1               5                   10

<210> SEQ ID NO 40
<211> LENGTH: 12
<212> TYPE: PRT
<213> ORGANISM: Artificial sequence
<220> FEATURE:
<223> OTHER INFORMATION: Synthetic peptide

<400> SEQUENCE: 40

Leu Arg Arg Ala Ser Ala Pro Leu Pro Gly Lys Ser
1               5                   10

<210> SEQ ID NO 41
<211> LENGTH: 12
<212> TYPE: PRT
<213> ORGANISM: Artificial sequence
<220> FEATURE:

-continued

```
<223> OTHER INFORMATION: Synthetic peptide

<400> SEQUENCE: 41

Leu Arg Arg Ala Ser Ala Pro Leu Pro Gly Lys Thr
1               5                   10

<210> SEQ ID NO 42
<211> LENGTH: 12
<212> TYPE: PRT
<213> ORGANISM: Artificial sequence
<220> FEATURE:
<223> OTHER INFORMATION: Synthetic peptide

<400> SEQUENCE: 42

Leu Arg Arg Ala Ser Ala Pro Leu Pro Asp Leu Ser
1               5                   10

<210> SEQ ID NO 43
<211> LENGTH: 12
<212> TYPE: PRT
<213> ORGANISM: Artificial sequence
<220> FEATURE:
<223> OTHER INFORMATION: Synthetic peptide

<400> SEQUENCE: 43

Leu Arg Arg Ala Ser Ala Pro Leu Pro Asp Leu Thr
1               5                   10

<210> SEQ ID NO 44
<211> LENGTH: 12
<212> TYPE: PRT
<213> ORGANISM: Artificial sequence
<220> FEATURE:
<223> OTHER INFORMATION: Synthetic peptide

<400> SEQUENCE: 44

Leu Arg Arg Ala Ser Ala Pro Leu Pro Asp Lys Ser
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic peptide

<400> SEQUENCE: 45

Leu Arg Arg Ala Ser Ala Pro Leu Pro Asp Lys Thr
1               5                   10

<210> SEQ ID NO 46
<211> LENGTH: 11
<212> TYPE: PRT
<213> ORGANISM: Artificial sequence
<220> FEATURE:
<223> OTHER INFORMATION: Synthetic peptide

<400> SEQUENCE: 46

Trp Leu Arg Arg Ala Ser Ala Pro Leu Pro Gly
1               5                   10

<210> SEQ ID NO 47
<211> LENGTH: 11
<212> TYPE: PRT
<213> ORGANISM: Artificial sequence
<220> FEATURE:
<223> OTHER INFORMATION: Synthetic peptide
```

-continued

<400> SEQUENCE: 47

Trp Leu Arg Arg Ala Ser Ala Pro Leu Pro Asp
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide

<400> SEQUENCE: 48

Trp Leu Arg Arg Ala Ser Ala Pro Leu Pro Gly Leu
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Trp Leu Arg Arg Ala Ser Ala Pro Leu Pro Gly Lys
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide

<400> SEQUENCE: 50

Trp Leu Arg Arg Ala Ser Ala Pro Leu Pro Asp Leu
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic peptide

<400> SEQUENCE: 51

Trp Leu Arg Arg Ala Ser Ala Pro Leu Pro Asp Lys
1               5                   10

<210> SEQ ID NO 52
<211> LENGTH: 13
<212> TYPE: PRT
<213> ORGANISM: Artificial sequence
<220> FEATURE:
<223> OTHER INFORMATION: Synthetic peptide

<400> SEQUENCE: 52

Trp Leu Arg Arg Ala Ser Ala Pro Leu Pro Gly Leu Ser
1               5                   10

<210> SEQ ID NO 53
<211> LENGTH: 13
<212> TYPE: PRT
<213> ORGANISM: Artificial sequence
<220> FEATURE:
<223> OTHER INFORMATION: Synthetic peptide

```
<400> SEQUENCE: 53

Trp Leu Arg Arg Ala Ser Ala Pro Leu Pro Gly Leu Thr
1               5                   10

<210> SEQ ID NO 54
<211> LENGTH: 13
<212> TYPE: PRT
<213> ORGANISM: Artificial sequence
<220> FEATURE:
<223> OTHER INFORMATION: Synthetic peptide

<400> SEQUENCE: 54

Trp Leu Arg Arg Ala Ser Ala Pro Leu Pro Gly Lys Ser
1               5                   10

<210> SEQ ID NO 55
<211> LENGTH: 13
<212> TYPE: PRT
<213> ORGANISM: Artificial sequence
<220> FEATURE:
<223> OTHER INFORMATION: Synthetic peptide

<400> SEQUENCE: 55

Trp Leu Arg Arg Ala Ser Ala Pro Leu Pro Gly Lys Thr
1               5                   10

<210> SEQ ID NO 56
<211> LENGTH: 13
<212> TYPE: PRT
<213> ORGANISM: Artificial sequence
<220> FEATURE:
<223> OTHER INFORMATION: Synthetic peptide

<400> SEQUENCE: 56

Trp Leu Arg Arg Ala Ser Ala Pro Leu Pro Asp Leu Ser
1               5                   10

<210> SEQ ID NO 57
<211> LENGTH: 13
<212> TYPE: PRT
<213> ORGANISM: Artificial sequence
<220> FEATURE:
<223> OTHER INFORMATION: Synthetic peptide

<400> SEQUENCE: 57

Trp Leu Arg Arg Ala Ser Ala Pro Leu Pro Asp Leu Thr
1               5                   10

<210> SEQ ID NO 58
<211> LENGTH: 13
<212> TYPE: PRT
<213> ORGANISM: Artificial sequence
<220> FEATURE:
<223> OTHER INFORMATION: Synthetic peptide

<400> SEQUENCE: 58

Trp Leu Arg Arg Ala Ser Ala Pro Leu Pro Asp Lys Ser
1               5                   10

<210> SEQ ID NO 59
<211> LENGTH: 13
<212> TYPE: PRT
<213> ORGANISM: Artificial sequence
<220> FEATURE:
<223> OTHER INFORMATION: Synthetic peptide

<400> SEQUENCE: 59
```

```
Trp Leu Arg Arg Ala Ser Ala Pro Leu Pro Asp Lys Thr
1               5                   10
```

<210> SEQ ID NO 60
<211> LENGTH: 9
<212> TYPE: PRT
<213> ORGANISM: Artificial sequence
<220> FEATURE:
<223> OTHER INFORMATION: Synthetic peptide

<400> SEQUENCE: 60

```
Arg Arg Ala Thr Ala Pro Leu Pro Gly
1               5
```

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

```
Arg Arg Ala Thr Ala Pro Leu Pro Asp
1               5
```

<210> SEQ ID NO 62
<211> LENGTH: 10
<212> TYPE: PRT
<213> ORGANISM: Artificial sequence
<220> FEATURE:
<223> OTHER INFORMATION: Synthetic peptide

<400> SEQUENCE: 62

```
Arg Arg Ala Thr Ala Pro Leu Pro Gly Leu
1               5                   10
```

<210> SEQ ID NO 63
<211> LENGTH: 10
<212> TYPE: PRT
<213> ORGANISM: Artificial sequence
<220> FEATURE:
<223> OTHER INFORMATION: Synthetic peptide

<400> SEQUENCE: 63

```
Arg Arg Ala Thr Ala Pro Leu Pro Gly Lys
1               5                   10
```

<210> SEQ ID NO 64
<211> LENGTH: 10
<212> TYPE: PRT
<213> ORGANISM: Artificial sequence
<220> FEATURE:
<223> OTHER INFORMATION: Synthetic peptide

<400> SEQUENCE: 64

```
Arg Arg Ala Thr Ala Pro Leu Pro Asp Leu
1               5                   10
```

<210> SEQ ID NO 65
<211> LENGTH: 10
<212> TYPE: PRT
<213> ORGANISM: Artificial sequence
<220> FEATURE:
<223> OTHER INFORMATION: Synthetic peptide

<400> SEQUENCE: 65

Arg Arg Ala Thr Ala Pro Leu Pro Asp Lys
1               5                   10

<210> SEQ ID NO 66
<211> LENGTH: 11
<212> TYPE: PRT
<213> ORGANISM: Artificial sequence
<220> FEATURE:
<223> OTHER INFORMATION: Synthetic peptide

<400> SEQUENCE: 66

Arg Arg Ala Thr Ala Pro Leu Pro Gly Leu Ser
1               5                   10

<210> SEQ ID NO 67
<211> LENGTH: 11
<212> TYPE: PRT
<213> ORGANISM: Artificial sequence
<220> FEATURE:
<223> OTHER INFORMATION: Synthetic peptide

<400> SEQUENCE: 67

Arg Arg Ala Thr Ala Pro Leu Pro Gly Leu Thr
1               5                   10

<210> SEQ ID NO 68
<211> LENGTH: 11
<212> TYPE: PRT
<213> ORGANISM: Artificial sequence
<220> FEATURE:
<223> OTHER INFORMATION: Synthetic peptide

<400> SEQUENCE: 68

Arg Arg Ala Thr Ala Pro Leu Pro Gly Lys Ser
1               5                   10

<210> SEQ ID NO 69
<211> LENGTH: 11
<212> TYPE: PRT
<213> ORGANISM: Artificial sequence
<220> FEATURE:
<223> OTHER INFORMATION: Synthetic peptide

<400> SEQUENCE: 69

Arg Arg Ala Thr Ala Pro Leu Pro Gly Lys Thr
1               5                   10

<210> SEQ ID NO 70
<211> LENGTH: 11
<212> TYPE: PRT
<213> ORGANISM: Artificial sequence
<220> FEATURE:
<223> OTHER INFORMATION: Synthetic peptide

<400> SEQUENCE: 70

Arg Arg Ala Thr Ala Pro Leu Pro Asp Leu Ser
1               5                   10

<210> SEQ ID NO 71
<211> LENGTH: 11
<212> TYPE: PRT
<213> ORGANISM: Artificial sequence
<220> FEATURE:
<223> OTHER INFORMATION: Synthetic peptide

<400> SEQUENCE: 71

Arg Arg Ala Thr Ala Pro Leu Pro Asp Leu Thr

<210> SEQ ID NO 72
<211> LENGTH: 11
<212> TYPE: PRT
<213> ORGANISM: Artificial sequence
<220> FEATURE:
<223> OTHER INFORMATION: Synthetic peptide

<400> SEQUENCE: 72

Arg Arg Ala Thr Ala Pro Leu Pro Asp Lys Ser
1               5                   10

<210> SEQ ID NO 73
<211> LENGTH: 11
<212> TYPE: PRT
<213> ORGANISM: Artificial sequence
<220> FEATURE:
<223> OTHER INFORMATION: Synthetic peptide

<400> SEQUENCE: 73

Arg Arg Ala Thr Ala Pro Leu Pro Asp Lys Thr
1               5                   10

<210> SEQ ID NO 74
<211> LENGTH: 10
<212> TYPE: PRT
<213> ORGANISM: Artificial sequence
<220> FEATURE:
<223> OTHER INFORMATION: Synthetic peptide

<400> SEQUENCE: 74

Leu Arg Arg Ala Thr Ala Pro Leu Pro Gly
1               5                   10

<210> SEQ ID NO 75
<211> LENGTH: 10
<212> TYPE: PRT
<213> ORGANISM: Artificial sequence
<220> FEATURE:
<223> OTHER INFORMATION: Synthetic peptide

<400> SEQUENCE: 75

Leu Arg Arg Ala Thr Ala Pro Leu Pro Asp
1               5                   10

<210> SEQ ID NO 76
<211> LENGTH: 11
<212> TYPE: PRT
<213> ORGANISM: Artificial sequence
<220> FEATURE:
<223> OTHER INFORMATION: Synthetic peptide

<400> SEQUENCE: 76

Leu Arg Arg Ala Thr Ala Pro Leu Pro Gly Leu
1               5                   10

<210> SEQ ID NO 77
<211> LENGTH: 11
<212> TYPE: PRT
<213> ORGANISM: Artificial sequence
<220> FEATURE:
<223> OTHER INFORMATION: Synthetic peptide

<400> SEQUENCE: 77

Leu Arg Arg Ala Thr Ala Pro Leu Pro Gly Lys
1               5                   10

```
<210> SEQ ID NO 78
<211> LENGTH: 11
<212> TYPE: PRT
<213> ORGANISM: Artificial sequence
<220> FEATURE:
<223> OTHER INFORMATION: Synthetic peptide

<400> SEQUENCE: 78

Leu Arg Arg Ala Thr Ala Pro Leu Pro Asp Leu
1               5                   10

<210> SEQ ID NO 79
<211> LENGTH: 11
<212> TYPE: PRT
<213> ORGANISM: Artificial sequence
<220> FEATURE:
<223> OTHER INFORMATION: Synthetic peptide

<400> SEQUENCE: 79

Leu Arg Arg Ala Thr Ala Pro Leu Pro Asp Lys
1               5                   10

<210> SEQ ID NO 80
<211> LENGTH: 12
<212> TYPE: PRT
<213> ORGANISM: Artificial sequence
<220> FEATURE:
<223> OTHER INFORMATION: Synthetic peptide

<400> SEQUENCE: 80

Leu Arg Arg Ala Thr Ala Pro Leu Pro Gly Leu Ser
1               5                   10

<210> SEQ ID NO 81
<211> LENGTH: 12
<212> TYPE: PRT
<213> ORGANISM: Artificial sequence
<220> FEATURE:
<223> OTHER INFORMATION: Synthetic peptide

<400> SEQUENCE: 81

Leu Arg Arg Ala Thr Ala Pro Leu Pro Gly Leu Thr
1               5                   10

<210> SEQ ID NO 82
<211> LENGTH: 12
<212> TYPE: PRT
<213> ORGANISM: Artificial sequence
<220> FEATURE:
<223> OTHER INFORMATION: Synthetic peptide

<400> SEQUENCE: 82

Leu Arg Arg Ala Thr Ala Pro Leu Pro Gly Lys Ser
1               5                   10

<210> SEQ ID NO 83
<211> LENGTH: 12
<212> TYPE: PRT
<213> ORGANISM: Artificial sequence
<220> FEATURE:
<223> OTHER INFORMATION: Synthetic peptide

<400> SEQUENCE: 83

Leu Arg Arg Ala Thr Ala Pro Leu Pro Gly Lys Thr
1               5                   10
```

```
<210> SEQ ID NO 84
<211> LENGTH: 12
<212> TYPE: PRT
<213> ORGANISM: Artificial sequence
<220> FEATURE:
<223> OTHER INFORMATION: Synthetic peptide

<400> SEQUENCE: 84

Leu Arg Arg Ala Thr Ala Pro Leu Pro Asp Leu Ser
1               5                   10

<210> SEQ ID NO 85
<211> LENGTH: 12
<212> TYPE: PRT
<213> ORGANISM: Artificial sequence
<220> FEATURE:
<223> OTHER INFORMATION: Synthetic peptide

<400> SEQUENCE: 85

Leu Arg Arg Ala Thr Ala Pro Leu Pro Asp Leu Thr
1               5                   10

<210> SEQ ID NO 86
<211> LENGTH: 12
<212> TYPE: PRT
<213> ORGANISM: Artificial sequence
<220> FEATURE:
<223> OTHER INFORMATION: Synthetic peptide

<400> SEQUENCE: 86

Leu Arg Arg Ala Thr Ala Pro Leu Pro Asp Lys Ser
1               5                   10

<210> SEQ ID NO 87
<211> LENGTH: 12
<212> TYPE: PRT
<213> ORGANISM: Artificial sequence
<220> FEATURE:
<223> OTHER INFORMATION: Synthetic peptide

<400> SEQUENCE: 87

Leu Arg Arg Ala Thr Ala Pro Leu Pro Asp Lys Thr
1               5                   10

<210> SEQ ID NO 88
<211> LENGTH: 11
<212> TYPE: PRT
<213> ORGANISM: Artificial sequence
<220> FEATURE:
<223> OTHER INFORMATION: Synthetic peptide

<400> SEQUENCE: 88

Trp Leu Arg Arg Ala Thr Ala Pro Leu Pro Gly
1               5                   10

<210> SEQ ID NO 89
<211> LENGTH: 11
<212> TYPE: PRT
<213> ORGANISM: Artificial sequence
<220> FEATURE:
<223> OTHER INFORMATION: Synthetic peptide

<400> SEQUENCE: 89

Trp Leu Arg Arg Ala Thr Ala Pro Leu Pro Asp
1               5                   10
```

<210> SEQ ID NO 90
<211> LENGTH: 12
<212> TYPE: PRT
<213> ORGANISM: Artificial sequence
<220> FEATURE:
<223> OTHER INFORMATION: Synthetic peptide

<400> SEQUENCE: 90

Trp Leu Arg Arg Ala Thr Ala Pro Leu Pro Gly Leu
1               5                   10

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Trp Leu Arg Arg Ala Thr Ala Pro Leu Pro Gly Lys
1               5                   10

<210> SEQ ID NO 92
<211> LENGTH: 12
<212> TYPE: PRT
<213> ORGANISM: Artificial sequence
<220> FEATURE:
<223> OTHER INFORMATION: Synthetic peptide

<400> SEQUENCE: 92

Trp Leu Arg Arg Ala Thr Ala Pro Leu Pro Asp Leu
1               5                   10

<210> SEQ ID NO 93
<211> LENGTH: 12
<212> TYPE: PRT
<213> ORGANISM: Artificial sequence
<220> FEATURE:
<223> OTHER INFORMATION: Synthetic peptide

<400> SEQUENCE: 93

Trp Leu Arg Arg Ala Thr Ala Pro Leu Pro Asp Lys
1               5                   10

<210> SEQ ID NO 94
<211> LENGTH: 13
<212> TYPE: PRT
<213> ORGANISM: Artificial sequence
<220> FEATURE:
<223> OTHER INFORMATION: Synthetic peptide

<400> SEQUENCE: 94

Trp Leu Arg Arg Ala Thr Ala Pro Leu Pro Gly Leu Ser
1               5                   10

<210> SEQ ID NO 95
<211> LENGTH: 13
<212> TYPE: PRT
<213> ORGANISM: Artificial sequence
<220> FEATURE:
<223> OTHER INFORMATION: Synthetic peptide

<400> SEQUENCE: 95

Trp Leu Arg Arg Ala Thr Ala Pro Leu Pro Gly Leu Thr
1               5                   10

<210> SEQ ID NO 96

<211> LENGTH: 13
<212> TYPE: PRT
<213> ORGANISM: Artificial sequence
<220> FEATURE:
<223> OTHER INFORMATION: Synthetic peptide

<400> SEQUENCE: 96

Trp Leu Arg Arg Ala Thr Ala Pro Leu Pro Gly Lys Ser
1               5                   10

<210> SEQ ID NO 97
<211> LENGTH: 13
<212> TYPE: PRT
<213> ORGANISM: Artificial sequence
<220> FEATURE:
<223> OTHER INFORMATION: Synthetic peptide

<400> SEQUENCE: 97

Trp Leu Arg Arg Ala Thr Ala Pro Leu Pro Gly Lys Thr
1               5                   10

<210> SEQ ID NO 98
<211> LENGTH: 13
<212> TYPE: PRT
<213> ORGANISM: Artificial sequence
<220> FEATURE:
<223> OTHER INFORMATION: Synthetic peptide

<400> SEQUENCE: 98

Trp Leu Arg Arg Ala Thr Ala Pro Leu Pro Asp Leu Ser
1               5                   10

<210> SEQ ID NO 99
<211> LENGTH: 13
<212> TYPE: PRT
<213> ORGANISM: Artificial sequence
<220> FEATURE:
<223> OTHER INFORMATION: Synthetic peptide

<400> SEQUENCE: 99

Trp Leu Arg Arg Ala Thr Ala Pro Leu Pro Asp Leu Thr
1               5                   10

<210> SEQ ID NO 100
<211> LENGTH: 13
<212> TYPE: PRT
<213> ORGANISM: Artificial sequence
<220> FEATURE:
<223> OTHER INFORMATION: Synthetic peptide

<400> SEQUENCE: 100

Trp Leu Arg Arg Ala Thr Ala Pro Leu Pro Asp Lys Ser
1               5                   10

<210> SEQ ID NO 101
<211> LENGTH: 13
<212> TYPE: PRT
<213> ORGANISM: Artificial sequence
<220> FEATURE:
<223> OTHER INFORMATION: Synthetic peptide

<400> SEQUENCE: 101

Trp Leu Arg Arg Ala Thr Ala Pro Leu Pro Asp Lys Thr
1               5                   10

<210> SEQ ID NO 102
<211> LENGTH: 9

<212> TYPE: PRT
<213> ORGANISM: Artificial sequence
<220> FEATURE:
<223> OTHER INFORMATION: Synthetic peptide

<400> SEQUENCE: 102

Arg Arg Ala Tyr Ala Pro Leu Pro Gly
1               5

<210> SEQ ID NO 103
<211> LENGTH: 9
<212> TYPE: PRT
<213> ORGANISM: Artificial sequence
<220> FEATURE:
<223> OTHER INFORMATION: Synthetic peptide

<400> SEQUENCE: 103

Arg Arg Ala Tyr Ala Pro Leu Pro Asp
1               5

<210> SEQ ID NO 104
<211> LENGTH: 10
<212> TYPE: PRT
<213> ORGANISM: Artificial sequence
<220> FEATURE:
<223> OTHER INFORMATION: Synthetic peptide

<400> SEQUENCE: 104

Arg Arg Ala Tyr Ala Pro Leu Pro Gly Leu
1               5                   10

<210> SEQ ID NO 105
<211> LENGTH: 10
<212> TYPE: PRT
<213> ORGANISM: Artificial sequence
<220> FEATURE:
<223> OTHER INFORMATION: Synthetic peptide

<400> SEQUENCE: 105

Arg Arg Ala Tyr Ala Pro Leu Pro Gly Lys
1               5                   10

<210> SEQ ID NO 106
<211> LENGTH: 10
<212> TYPE: PRT
<213> ORGANISM: Artificial sequence
<220> FEATURE:
<223> OTHER INFORMATION: Synthetic peptide

<400> SEQUENCE: 106

Arg Arg Ala Tyr Ala Pro Leu Pro Asp Leu
1               5                   10

<210> SEQ ID NO 107
<211> LENGTH: 10
<212> TYPE: PRT
<213> ORGANISM: Artificial sequence
<220> FEATURE:
<223> OTHER INFORMATION: Synthetic peptide

<400> SEQUENCE: 107

Arg Arg Ala Tyr Ala Pro Leu Pro Asp Lys
1               5                   10

<210> SEQ ID NO 108
<211> LENGTH: 11
<212> TYPE: PRT

```
<213> ORGANISM: Artificial sequence
<220> FEATURE:
<223> OTHER INFORMATION: Synthetic peptide

<400> SEQUENCE: 108

Arg Arg Ala Tyr Ala Pro Leu Pro Gly Leu Ser
1               5                   10

<210> SEQ ID NO 109
<211> LENGTH: 11
<212> TYPE: PRT
<213> ORGANISM: Artificial sequence
<220> FEATURE:
<223> OTHER INFORMATION: Synthetic peptide

<400> SEQUENCE: 109

Arg Arg Ala Tyr Ala Pro Leu Pro Gly Leu Thr
1               5                   10

<210> SEQ ID NO 110
<211> LENGTH: 11
<212> TYPE: PRT
<213> ORGANISM: Artificial sequence
<220> FEATURE:
<223> OTHER INFORMATION: Synthetic peptide

<400> SEQUENCE: 110

Arg Arg Ala Tyr Ala Pro Leu Pro Gly Lys Ser
1               5                   10

<210> SEQ ID NO 111
<211> LENGTH: 11
<212> TYPE: PRT
<213> ORGANISM: Artificial sequence
<220> FEATURE:
<223> OTHER INFORMATION: Synthetic peptide

<400> SEQUENCE: 111

Arg Arg Ala Tyr Ala Pro Leu Pro Gly Lys Thr
1               5                   10

<210> SEQ ID NO 112
<211> LENGTH: 11
<212> TYPE: PRT
<213> ORGANISM: Artificial sequence
<220> FEATURE:
<223> OTHER INFORMATION: Synthetic peptide

<400> SEQUENCE: 112

Arg Arg Ala Tyr Ala Pro Leu Pro Asp Leu Ser
1               5                   10

<210> SEQ ID NO 113
<211> LENGTH: 11
<212> TYPE: PRT
<213> ORGANISM: Artificial sequence
<220> FEATURE:
<223> OTHER INFORMATION: Synthetic peptide

<400> SEQUENCE: 113

Arg Arg Ala Tyr Ala Pro Leu Pro Asp Leu Thr
1               5                   10

<210> SEQ ID NO 114
<211> LENGTH: 11
<212> TYPE: PRT
<213> ORGANISM: Artificial sequence
```

```
<220> FEATURE:
<223> OTHER INFORMATION: Synthetic peptide

<400> SEQUENCE: 114

Arg Arg Ala Tyr Ala Pro Leu Pro Asp Lys Ser
1               5                   10

<210> SEQ ID NO 115
<211> LENGTH: 11
<212> TYPE: PRT
<213> ORGANISM: Artificial sequence
<220> FEATURE:
<223> OTHER INFORMATION: Synthetic peptide

<400> SEQUENCE: 115

Arg Arg Ala Tyr Ala Pro Leu Pro Asp Lys Thr
1               5                   10

<210> SEQ ID NO 116
<211> LENGTH: 10
<212> TYPE: PRT
<213> ORGANISM: Artificial sequence
<220> FEATURE:
<223> OTHER INFORMATION: Synthetic peptide

<400> SEQUENCE: 116

Leu Arg Arg Ala Tyr Ala Pro Leu Pro Gly
1               5                   10

<210> SEQ ID NO 117
<211> LENGTH: 10
<212> TYPE: PRT
<213> ORGANISM: Artificial sequence
<220> FEATURE:
<223> OTHER INFORMATION: Synthetic peptide

<400> SEQUENCE: 117

Leu Arg Arg Ala Tyr Ala Pro Leu Pro Asp
1               5                   10

<210> SEQ ID NO 118
<211> LENGTH: 11
<212> TYPE: PRT
<213> ORGANISM: Artificial sequence
<220> FEATURE:
<223> OTHER INFORMATION: Synthetic peptide

<400> SEQUENCE: 118

Leu Arg Arg Ala Tyr Ala Pro Leu Pro Gly Leu
1               5                   10

<210> SEQ ID NO 119
<211> LENGTH: 11
<212> TYPE: PRT
<213> ORGANISM: Artificial sequence
<220> FEATURE:
<223> OTHER INFORMATION: Synthetic peptide

<400> SEQUENCE: 119

Leu Arg Arg Ala Tyr Ala Pro Leu Pro Gly Lys
1               5                   10

<210> SEQ ID NO 120
<211> LENGTH: 11
<212> TYPE: PRT
<213> ORGANISM: Artificial sequence
<220> FEATURE:
```

<223> OTHER INFORMATION: Synthetic peptide

<400> SEQUENCE: 120

Leu Arg Arg Ala Tyr Ala Pro Leu Pro Asp Leu
1               5                   10

<210> SEQ ID NO 121
<211> LENGTH: 11
<212> TYPE: PRT
<213> ORGANISM: Artificial sequence
<220> FEATURE:
<223> OTHER INFORMATION: Synthetic peptide

<400> SEQUENCE: 121

Leu Arg Arg Ala Tyr Ala Pro Leu Pro Asp Lys
1               5                   10

<210> SEQ ID NO 122
<211> LENGTH: 12
<212> TYPE: PRT
<213> ORGANISM: Artificial sequence
<220> FEATURE:
<223> OTHER INFORMATION: Synthetic peptide

<400> SEQUENCE: 122

Leu Arg Arg Ala Tyr Ala Pro Leu Pro Gly Leu Ser
1               5                   10

<210> SEQ ID NO 123
<211> LENGTH: 12
<212> TYPE: PRT
<213> ORGANISM: Artificial sequence
<220> FEATURE:
<223> OTHER INFORMATION: Synthetic peptide

<400> SEQUENCE: 123

Leu Arg Arg Ala Tyr Ala Pro Leu Pro Gly Leu Thr
1               5                   10

<210> SEQ ID NO 124
<211> LENGTH: 12
<212> TYPE: PRT
<213> ORGANISM: Artificial sequence
<220> FEATURE:
<223> OTHER INFORMATION: Synthetic peptide

<400> SEQUENCE: 124

Leu Arg Arg Ala Tyr Ala Pro Leu Pro Gly Lys Ser
1               5                   10

<210> SEQ ID NO 125
<211> LENGTH: 12
<212> TYPE: PRT
<213> ORGANISM: Artificial sequence
<220> FEATURE:
<223> OTHER INFORMATION: Synthetic peptide

<400> SEQUENCE: 125

Leu Arg Arg Ala Tyr Ala Pro Leu Pro Gly Lys Thr
1               5                   10

<210> SEQ ID NO 126
<211> LENGTH: 12
<212> TYPE: PRT
<213> ORGANISM: Artificial sequence
<220> FEATURE:
<223> OTHER INFORMATION: Synthetic peptide

```
<400> SEQUENCE: 126

Leu Arg Arg Ala Tyr Ala Pro Leu Pro Asp Leu Ser
1               5                   10

<210> SEQ ID NO 127
<211> LENGTH: 12
<212> TYPE: PRT
<213> ORGANISM: Artificial sequence
<220> FEATURE:
<223> OTHER INFORMATION: Synthetic peptide

<400> SEQUENCE: 127

Leu Arg Arg Ala Tyr Ala Pro Leu Pro Asp Leu Thr
1               5                   10

<210> SEQ ID NO 128
<211> LENGTH: 12
<212> TYPE: PRT
<213> ORGANISM: Artificial sequence
<220> FEATURE:
<223> OTHER INFORMATION: Synthetic peptide

<400> SEQUENCE: 128

Leu Arg Arg Ala Tyr Ala Pro Leu Pro Asp Lys Ser
1               5                   10

<210> SEQ ID NO 129
<211> LENGTH: 12
<212> TYPE: PRT
<213> ORGANISM: Artificial sequence
<220> FEATURE:
<223> OTHER INFORMATION: Synthetic peptide

<400> SEQUENCE: 129

Leu Arg Arg Ala Tyr Ala Pro Leu Pro Asp Lys Thr
1               5                   10

<210> SEQ ID NO 130
<211> LENGTH: 11
<212> TYPE: PRT
<213> ORGANISM: Artificial sequence
<220> FEATURE:
<223> OTHER INFORMATION: Synthetic peptide

<400> SEQUENCE: 130

Trp Leu Arg Arg Ala Tyr Ala Pro Leu Pro Gly
1               5                   10

<210> SEQ ID NO 131
<211> LENGTH: 11
<212> TYPE: PRT
<213> ORGANISM: Artificial sequence
<220> FEATURE:
<223> OTHER INFORMATION: Synthetic peptide

<400> SEQUENCE: 131

Trp Leu Arg Arg Ala Tyr Ala Pro Leu Pro Asp
1               5                   10

<210> SEQ ID NO 132
<211> LENGTH: 12
<212> TYPE: PRT
<213> ORGANISM: Artificial sequence
<220> FEATURE:
<223> OTHER INFORMATION: Synthetic peptide
```

```
<400> SEQUENCE: 132

Trp Leu Arg Arg Ala Tyr Ala Pro Leu Pro Gly Leu
1               5                   10

<210> SEQ ID NO 133
<211> LENGTH: 12
<212> TYPE: PRT
<213> ORGANISM: Artificial sequence
<220> FEATURE:
<223> OTHER INFORMATION: Synthetic peptide

<400> SEQUENCE: 133

Trp Leu Arg Arg Ala Tyr Ala Pro Leu Pro Gly Lys
1               5                   10

<210> SEQ ID NO 134
<211> LENGTH: 12
<212> TYPE: PRT
<213> ORGANISM: Artificial sequence
<220> FEATURE:
<223> OTHER INFORMATION: Synthetic peptide

<400> SEQUENCE: 134

Trp Leu Arg Arg Ala Tyr Ala Pro Leu Pro Asp Leu
1               5                   10

<210> SEQ ID NO 135
<211> LENGTH: 12
<212> TYPE: PRT
<213> ORGANISM: Artificial sequence
<220> FEATURE:
<223> OTHER INFORMATION: Synthetic peptide

<400> SEQUENCE: 135

Trp Leu Arg Arg Ala Tyr Ala Pro Leu Pro Asp Lys
1               5                   10

<210> SEQ ID NO 136
<211> LENGTH: 13
<212> TYPE: PRT
<213> ORGANISM: Artificial sequence
<220> FEATURE:
<223> OTHER INFORMATION: Synthetic peptide

<400> SEQUENCE: 136

Trp Leu Arg Arg Ala Tyr Ala Pro Leu Pro Gly Leu Ser
1               5                   10

<210> SEQ ID NO 137
<211> LENGTH: 13
<212> TYPE: PRT
<213> ORGANISM: Artificial sequence
<220> FEATURE:
<223> OTHER INFORMATION: Synthetic peptide

<400> SEQUENCE: 137

Trp Leu Arg Arg Ala Tyr Ala Pro Leu Pro Gly Leu Thr
1               5                   10

<210> SEQ ID NO 138
<211> LENGTH: 13
<212> TYPE: PRT
<213> ORGANISM: Artificial sequence
<220> FEATURE:
<223> OTHER INFORMATION: Synthetic peptide

<400> SEQUENCE: 138
```

Trp Leu Arg Arg Ala Tyr Ala Pro Leu Pro Gly Lys Ser
1               5                   10

<210> SEQ ID NO 139
<211> LENGTH: 13
<212> TYPE: PRT
<213> ORGANISM: Artificial sequence
<220> FEATURE:
<223> OTHER INFORMATION: Synthetic peptide

<400> SEQUENCE: 139

Trp Leu Arg Arg Ala Tyr Ala Pro Leu Pro Gly Lys Thr
1               5                   10

<210> SEQ ID NO 140
<211> LENGTH: 13
<212> TYPE: PRT
<213> ORGANISM: Artificial sequence
<220> FEATURE:
<223> OTHER INFORMATION: Synthetic peptide

<400> SEQUENCE: 140

Trp Leu Arg Arg Ala Tyr Ala Pro Leu Pro Asp Leu Ser
1               5                   10

<210> SEQ ID NO 141
<211> LENGTH: 13
<212> TYPE: PRT
<213> ORGANISM: Artificial sequence
<220> FEATURE:
<223> OTHER INFORMATION: Synthetic peptide

<400> SEQUENCE: 141

Trp Leu Arg Arg Ala Tyr Ala Pro Leu Pro Asp Leu Thr
1               5                   10

<210> SEQ ID NO 142
<211> LENGTH: 13
<212> TYPE: PRT
<213> ORGANISM: Artificial sequence
<220> FEATURE:
<223> OTHER INFORMATION: Synthetic peptide

<400> SEQUENCE: 142

Trp Leu Arg Arg Ala Tyr Ala Pro Leu Pro Asp Lys Ser
1               5                   10

<210> SEQ ID NO 143
<211> LENGTH: 13
<212> TYPE: PRT
<213> ORGANISM: Artificial sequence
<220> FEATURE:
<223> OTHER INFORMATION: Synthetic peptide

<400> SEQUENCE: 143

Trp Leu Arg Arg Ala Tyr Ala Pro Leu Pro Asp Lys Thr
1               5                   10

<210> SEQ ID NO 144
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc_feature
<222> LOCATION: (1)..(1)

```
<223> OTHER INFORMATION: X is F, Y, or W

<400> SEQUENCE: 144

Xaa Arg Arg Ala Ser Ala Pro Leu Pro
1               5

<210> SEQ ID NO 145
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 145

Xaa Leu Arg Arg Ala Ser Ala Pro Leu Pro
1               5                   10

<210> SEQ ID NO 146
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 146

Xaa Trp Leu Arg Arg Ala Ser Ala Pro Leu Pro
1               5                   10

<210> SEQ ID NO 147
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 147

Xaa Arg Arg Ala Thr Ala Pro Leu Pro
1               5

<210> SEQ ID NO 148
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 148

Xaa Leu Arg Arg Ala Thr Ala Pro Leu Pro
1               5                   10

<210> SEQ ID NO 149
<211> LENGTH: 11
<212> TYPE: PRT
```

<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 149

Xaa Trp Leu Arg Arg Ala Thr Ala Pro Leu Pro
1               5                   10

<210> SEQ ID NO 150
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 150

Xaa Arg Arg Ala Tyr Ala Pro Leu Pro
1               5

<210> SEQ ID NO 151
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 151

Xaa Leu Arg Arg Ala Tyr Ala Pro Leu Pro
1               5                   10

<210> SEQ ID NO 152
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 152

Xaa Trp Leu Arg Arg Ala Tyr Ala Pro Leu Pro
1               5                   10

<210> SEQ ID NO 153
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 153

Xaa Arg Arg Ala Ser Ala Pro Leu Pro Gly

-continued

```
1               5                   10

<210> SEQ ID NO 154
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 154

Xaa Arg Arg Ala Ser Ala Pro Leu Pro Asp
1               5                   10

<210> SEQ ID NO 155
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 155

Xaa Arg Arg Ala Ser Ala Pro Leu Pro Gly Leu
1               5                   10

<210> SEQ ID NO 156
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 156

Xaa Arg Arg Ala Ser Ala Pro Leu Pro Gly Lys
1               5                   10

<210> SEQ ID NO 157
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 157

Xaa Arg Arg Ala Ser Ala Pro Leu Pro Asp Leu
1               5                   10

<210> SEQ ID NO 158
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

<222> LOCATION: (1)..(1)
<223> OTHER INFORMATION: X is F, Y, or W

<400> SEQUENCE: 158

Xaa Arg Arg Ala Ser Ala Pro Leu Pro Asp Lys
1               5                   10

<210> SEQ ID NO 159
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 159

Xaa Arg Arg Ala Ser Ala Pro Leu Pro Gly Leu Ser
1               5                   10

<210> SEQ ID NO 160
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 160

Xaa Arg Arg Ala Ser Ala Pro Leu Pro Gly Leu Thr
1               5                   10

<210> SEQ ID NO 161
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 161

Xaa Arg Arg Ala Ser Ala Pro Leu Pro Gly Lys Ser
1               5                   10

<210> SEQ ID NO 162
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 162

Xaa Arg Arg Ala Ser Ala Pro Leu Pro Gly Lys Thr
1               5                   10

<210> SEQ ID NO 163
<211> LENGTH: 12

```
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 163

Xaa Arg Arg Ala Ser Ala Pro Leu Pro Asp Leu Ser
1               5                   10

<210> SEQ ID NO 164
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 164

Xaa Arg Arg Ala Ser Ala Pro Leu Pro Asp Leu Thr
1               5                   10

<210> SEQ ID NO 165
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 165

Xaa Arg Arg Ala Ser Ala Pro Leu Pro Asp Lys Ser
1               5                   10

<210> SEQ ID NO 166
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 166

Xaa Arg Arg Ala Ser Ala Pro Leu Pro Asp Lys Thr
1               5                   10

<210> SEQ ID NO 167
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 167
```

```
Xaa Leu Arg Arg Ala Ser Ala Pro Leu Pro Gly
1               5                   10

<210> SEQ ID NO 168
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 168

Xaa Leu Arg Arg Ala Ser Ala Pro Leu Pro Asp
1               5                   10

<210> SEQ ID NO 169
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 169

Xaa Leu Arg Arg Ala Ser Ala Pro Leu Pro Gly Leu
1               5                   10

<210> SEQ ID NO 170
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 170

Xaa Leu Arg Arg Ala Ser Ala Pro Leu Pro Gly Lys
1               5                   10

<210> SEQ ID NO 171
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 171

Xaa Leu Arg Arg Ala Ser Ala Pro Leu Pro Asp Leu
1               5                   10

<210> SEQ ID NO 172
<211> LENGTH: 12
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: X is F, Y, or W

<400> SEQUENCE: 172

Xaa Leu Arg Arg Ala Ser Ala Pro Leu Pro Asp Lys
1               5                   10

<210> SEQ ID NO 173
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 173

Xaa Leu Arg Arg Ala Ser Ala Pro Leu Pro Gly Leu Ser
1               5                   10

<210> SEQ ID NO 174
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 174

Xaa Leu Arg Arg Ala Ser Ala Pro Leu Pro Gly Leu Thr
1               5                   10

<210> SEQ ID NO 175
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 175

Xaa Leu Arg Arg Ala Ser Ala Pro Leu Pro Gly Lys Ser
1               5                   10

<210> SEQ ID NO 176
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 176

Xaa Leu Arg Arg Ala Ser Ala Pro Leu Pro Gly Lys Thr
1               5                   10

<210> SEQ ID NO 177
```

```
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 177

Xaa Leu Arg Arg Ala Ser Ala Pro Leu Pro Asp Leu Ser
 1               5                  10

<210> SEQ ID NO 178
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 178

Xaa Leu Arg Arg Ala Ser Ala Pro Leu Pro Asp Leu Thr
 1               5                  10

<210> SEQ ID NO 179
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 179

Xaa Leu Arg Arg Ala Ser Ala Pro Leu Pro Asp Lys Ser
 1               5                  10

<210> SEQ ID NO 180
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 180

Xaa Leu Arg Arg Ala Ser Ala Pro Leu Pro Asp Lys Thr
 1               5                  10

<210> SEQ ID NO 181
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 181
```

```
Xaa Trp Leu Arg Arg Ala Ser Ala Pro Leu Pro Gly
1               5                   10

<210> SEQ ID NO 182
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 182

Xaa Trp Leu Arg Arg Ala Ser Ala Pro Leu Pro Asp
1               5                   10

<210> SEQ ID NO 183
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 183

Xaa Trp Leu Arg Arg Ala Ser Ala Pro Leu Pro Gly Leu
1               5                   10

<210> SEQ ID NO 184
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 184

Xaa Trp Leu Arg Arg Ala Ser Ala Pro Leu Pro Gly Lys
1               5                   10

<210> SEQ ID NO 185
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 185

Xaa Trp Leu Arg Arg Ala Ser Ala Pro Leu Pro Asp Leu
1               5                   10

<210> SEQ ID NO 186
<211> LENGTH: 13
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: X is F, Y, or W

<400> SEQUENCE: 186

Xaa Trp Leu Arg Arg Ala Ser Ala Pro Leu Pro Asp Lys
1               5                   10

<210> SEQ ID NO 187
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 187

Xaa Trp Leu Arg Arg Ala Ser Ala Pro Leu Pro Gly Leu Ser
1               5                   10

<210> SEQ ID NO 188
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 188

Xaa Trp Leu Arg Arg Ala Ser Ala Pro Leu Pro Gly Leu Thr
1               5                   10

<210> SEQ ID NO 189
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 189

Xaa Trp Leu Arg Arg Ala Ser Ala Pro Leu Pro Gly Lys Ser
1               5                   10

<210> SEQ ID NO 190
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 190

Xaa Trp Leu Arg Arg Ala Ser Ala Pro Leu Pro Gly Lys Thr
1               5                   10
```

```
<210> SEQ ID NO 191
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 191

Xaa Trp Leu Arg Arg Ala Ser Ala Pro Leu Pro Asp Leu Ser
1               5                   10

<210> SEQ ID NO 192
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 192

Xaa Trp Leu Arg Arg Ala Ser Ala Pro Leu Pro Asp Leu Thr
1               5                   10

<210> SEQ ID NO 193
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 193

Xaa Trp Leu Arg Arg Ala Ser Ala Pro Leu Pro Asp Lys Ser
1               5                   10

<210> SEQ ID NO 194
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 194

Xaa Trp Leu Arg Arg Ala Ser Ala Pro Leu Pro Asp Lys Thr
1               5                   10

<210> SEQ ID NO 195
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W
```

```
<400> SEQUENCE: 195

Xaa Arg Arg Ala Thr Ala Pro Leu Pro Gly
1               5                   10

<210> SEQ ID NO 196
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 196

Xaa Arg Arg Ala Thr Ala Pro Leu Pro Asp
1               5                   10

<210> SEQ ID NO 197
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 197

Xaa Arg Arg Ala Thr Ala Pro Leu Pro Gly Leu
1               5                   10

<210> SEQ ID NO 198
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 198

Xaa Arg Arg Ala Thr Ala Pro Leu Pro Gly Lys
1               5                   10

<210> SEQ ID NO 199
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 199

Xaa Arg Arg Ala Thr Ala Pro Leu Pro Asp Leu
1               5                   10

<210> SEQ ID NO 200
<211> LENGTH: 11
<212> TYPE: PRT
<213> ORGANISM: Artificial sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 200

Xaa Arg Arg Ala Thr Ala Pro Leu Pro Asp Lys
1               5                   10

<210> SEQ ID NO 201
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 201

Xaa Arg Arg Ala Thr Ala Pro Leu Pro Gly Leu Ser
1               5                   10

<210> SEQ ID NO 202
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 202

Xaa Arg Arg Ala Thr Ala Pro Leu Pro Gly Leu Thr
1               5                   10

<210> SEQ ID NO 203
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 203

Xaa Arg Arg Ala Thr Ala Pro Leu Pro Gly Lys Ser
1               5                   10

<210> SEQ ID NO 204
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 204

Xaa Arg Arg Ala Thr Ala Pro Leu Pro Gly Lys Thr
1               5                   10
```

```
<210> SEQ ID NO 205
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 205

Xaa Arg Arg Ala Thr Ala Pro Leu Pro Asp Leu Ser
1               5                   10

<210> SEQ ID NO 206
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 206

Xaa Arg Arg Ala Thr Ala Pro Leu Pro Asp Leu Thr
1               5                   10

<210> SEQ ID NO 207
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 207

Xaa Arg Arg Ala Thr Ala Pro Leu Pro Asp Lys Ser
1               5                   10

<210> SEQ ID NO 208
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 208

Xaa Arg Arg Ala Thr Ala Pro Leu Pro Asp Lys Thr
1               5                   10

<210> SEQ ID NO 209
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W
```

<400> SEQUENCE: 209

Xaa Leu Arg Arg Ala Thr Ala Pro Leu Pro Gly
1               5                   10

<210> SEQ ID NO 210
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 210

Xaa Leu Arg Arg Ala Thr Ala Pro Leu Pro Asp
1               5                   10

<210> SEQ ID NO 211
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 211

Xaa Leu Arg Arg Ala Thr Ala Pro Leu Pro Gly Leu
1               5                   10

<210> SEQ ID NO 212
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 212

Xaa Leu Arg Arg Ala Thr Ala Pro Leu Pro Gly Lys
1               5                   10

<210> SEQ ID NO 213
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 213

Xaa Leu Arg Arg Ala Thr Ala Pro Leu Pro Asp Leu
1               5                   10

<210> SEQ ID NO 214
<211> LENGTH: 12
<212> TYPE: PRT
<213> ORGANISM: Artificial sequence

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 214

Xaa Leu Arg Arg Ala Thr Ala Pro Leu Pro Asp Lys
1               5                   10

<210> SEQ ID NO 215
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 215

Xaa Leu Arg Arg Ala Thr Ala Pro Leu Pro Gly Leu Ser
1               5                   10

<210> SEQ ID NO 216
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 216

Xaa Leu Arg Arg Ala Thr Ala Pro Leu Pro Gly Leu Thr
1               5                   10

<210> SEQ ID NO 217
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 217

Xaa Leu Arg Arg Ala Thr Ala Pro Leu Pro Gly Lys Ser
1               5                   10

<210> SEQ ID NO 218
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 218

Xaa Leu Arg Arg Ala Thr Ala Pro Leu Pro Gly Lys Thr
1               5                   10
```

-continued

<210> SEQ ID NO 219
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 219

Xaa Leu Arg Arg Ala Thr Ala Pro Leu Pro Asp Leu Ser
1               5                   10

<210> SEQ ID NO 220
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 220

Xaa Leu Arg Arg Ala Thr Ala Pro Leu Pro Asp Leu Thr
1               5                   10

<210> SEQ ID NO 221
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 221

Xaa Leu Arg Arg Ala Thr Ala Pro Leu Pro Asp Lys Ser
1               5                   10

<210> SEQ ID NO 222
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 222

Xaa Leu Arg Arg Ala Thr Ala Pro Leu Pro Asp Lys Thr
1               5                   10

<210> SEQ ID NO 223
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)

<223> OTHER INFORMATION: X is F, Y, or W

<400> SEQUENCE: 223

Xaa Trp Leu Arg Arg Ala Thr Ala Pro Leu Pro Gly
1               5                   10

<210> SEQ ID NO 224
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 224

Xaa Trp Leu Arg Arg Ala Thr Ala Pro Leu Pro Asp
1               5                   10

<210> SEQ ID NO 225
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 225

Xaa Trp Leu Arg Arg Ala Thr Ala Pro Leu Pro Gly Leu
1               5                   10

<210> SEQ ID NO 226
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 226

Xaa Trp Leu Arg Arg Ala Thr Ala Pro Leu Pro Gly Lys
1               5                   10

<210> SEQ ID NO 227
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 227

Xaa Trp Leu Arg Arg Ala Thr Ala Pro Leu Pro Asp Leu
1               5                   10

<210> SEQ ID NO 228
<211> LENGTH: 13
<212> TYPE: PRT

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 228

Xaa Trp Leu Arg Arg Ala Thr Ala Pro Leu Pro Asp Lys
1               5                   10

<210> SEQ ID NO 229
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 229

Xaa Trp Leu Arg Arg Ala Thr Ala Pro Leu Pro Gly Leu Ser
1               5                   10

<210> SEQ ID NO 230
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 230

Xaa Trp Leu Arg Arg Ala Thr Ala Pro Leu Pro Gly Leu Thr
1               5                   10

<210> SEQ ID NO 231
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 231

Xaa Trp Leu Arg Arg Ala Thr Ala Pro Leu Pro Gly Lys Ser
1               5                   10

<210> SEQ ID NO 232
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 232

Xaa Trp Leu Arg Arg Ala Thr Ala Pro Leu Pro Gly Lys Thr
```

-continued

<210> SEQ ID NO 233
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 233

Xaa Trp Leu Arg Arg Ala Thr Ala Pro Leu Pro Asp Leu Ser
1               5                   10

<210> SEQ ID NO 234
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 234

Xaa Trp Leu Arg Arg Ala Thr Ala Pro Leu Pro Asp Leu Thr
1               5                   10

<210> SEQ ID NO 235
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 235

Xaa Trp Leu Arg Arg Ala Thr Ala Pro Leu Pro Asp Lys Ser
1               5                   10

<210> SEQ ID NO 236
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 236

Xaa Trp Leu Arg Arg Ala Thr Ala Pro Leu Pro Asp Lys Thr
1               5                   10

<210> SEQ ID NO 237
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE

```
<222> LOCATION: (1)..(1)
<223> OTHER INFORMATION: X is F, Y, or W

<400> SEQUENCE: 237

Xaa Arg Arg Ala Tyr Ala Pro Leu Pro Gly
1               5                   10

<210> SEQ ID NO 238
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 238

Xaa Arg Arg Ala Tyr Ala Pro Leu Pro Asp
1               5                   10

<210> SEQ ID NO 239
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 239

Xaa Arg Arg Ala Tyr Ala Pro Leu Pro Gly Leu
1               5                   10

<210> SEQ ID NO 240
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 240

Xaa Arg Arg Ala Tyr Ala Pro Leu Pro Gly Lys
1               5                   10

<210> SEQ ID NO 241
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 241

Xaa Arg Arg Ala Tyr Ala Pro Leu Pro Asp Leu
1               5                   10

<210> SEQ ID NO 242
<211> LENGTH: 11
```

```
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 242

Xaa Arg Arg Ala Tyr Ala Pro Leu Pro Asp Lys
1               5                   10

<210> SEQ ID NO 243
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 243

Xaa Arg Arg Ala Tyr Ala Pro Leu Pro Gly Leu Ser
1               5                   10

<210> SEQ ID NO 244
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 244

Xaa Arg Arg Ala Tyr Ala Pro Leu Pro Gly Leu Thr
1               5                   10

<210> SEQ ID NO 245
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 245

Xaa Arg Arg Ala Tyr Ala Pro Leu Pro Gly Lys Ser
1               5                   10

<210> SEQ ID NO 246
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 246
```

-continued

Xaa Arg Arg Ala Tyr Ala Pro Leu Pro Gly Lys Thr
1               5                   10

<210> SEQ ID NO 247
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 247

Xaa Arg Arg Ala Tyr Ala Pro Leu Pro Asp Leu Ser
1               5                   10

<210> SEQ ID NO 248
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 248

Xaa Arg Arg Ala Tyr Ala Pro Leu Pro Asp Leu Thr
1               5                   10

<210> SEQ ID NO 249
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 249

Xaa Arg Arg Ala Tyr Ala Pro Leu Pro Asp Lys Ser
1               5                   10

<210> SEQ ID NO 250
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 250

Xaa Arg Arg Ala Tyr Ala Pro Leu Pro Asp Lys Thr
1               5                   10

<210> SEQ ID NO 251
<211> LENGTH: 11
<212> TYPE: PRT
<213> ORGANISM: Artificial sequence
<220> FEATURE:
<223> OTHER INFORMATION: Synthetic peptide
<220> FEATURE:

<221> NAME/KEY: MISC_FEATURE
<222> LOCATION: (1)..(1)
<223> OTHER INFORMATION: X is F, Y, or W

<400> SEQUENCE: 251

Xaa Leu Arg Arg Ala Tyr Ala Pro Leu Pro Gly
1               5                   10

<210> SEQ ID NO 252
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 252

Xaa Leu Arg Arg Ala Tyr Ala Pro Leu Pro Asp
1               5                   10

<210> SEQ ID NO 253
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 253

Xaa Leu Arg Arg Ala Tyr Ala Pro Leu Pro Gly Leu
1               5                   10

<210> SEQ ID NO 254
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 254

Xaa Leu Arg Arg Ala Tyr Ala Pro Leu Pro Gly Lys
1               5                   10

<210> SEQ ID NO 255
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 255

Xaa Leu Arg Arg Ala Tyr Ala Pro Leu Pro Asp Leu
1               5                   10

<210> SEQ ID NO 256

```
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 256

Xaa Leu Arg Arg Ala Tyr Ala Pro Leu Pro Asp Lys
1               5                   10

<210> SEQ ID NO 257
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 257

Xaa Leu Arg Arg Ala Tyr Ala Pro Leu Pro Gly Leu Ser
1               5                   10

<210> SEQ ID NO 258
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 258

Xaa Leu Arg Arg Ala Tyr Ala Pro Leu Pro Gly Leu Thr
1               5                   10

<210> SEQ ID NO 259
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 259

Xaa Leu Arg Arg Ala Tyr Ala Pro Leu Pro Gly Lys Ser
1               5                   10

<210> SEQ ID NO 260
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 260
```

Xaa Leu Arg Arg Ala Tyr Ala Pro Leu Pro Gly Lys Thr
1               5                   10

<210> SEQ ID NO 261
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 261

Xaa Leu Arg Arg Ala Tyr Ala Pro Leu Pro Asp Leu Ser
1               5                   10

<210> SEQ ID NO 262
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 262

Xaa Leu Arg Arg Ala Tyr Ala Pro Leu Pro Asp Leu Thr
1               5                   10

<210> SEQ ID NO 263
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 263

Xaa Leu Arg Arg Ala Tyr Ala Pro Leu Pro Asp Lys Ser
1               5                   10

<210> SEQ ID NO 264
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 264

Xaa Leu Arg Arg Ala Tyr Ala Pro Leu Pro Asp Lys Thr
1               5                   10

<210> SEQ ID NO 265
<211> LENGTH: 12
<212> TYPE: PRT
<213> ORGANISM: Artificial sequence
<220> FEATURE:
<223> OTHER INFORMATION: Synthetic peptide

```
<220> FEATURE:
<221> NAME/KEY: MISC_FEATURE
<222> LOCATION: (1)..(1)
<223> OTHER INFORMATION: X is F, Y, or W

<400> SEQUENCE: 265

Xaa Trp Leu Arg Arg Ala Tyr Ala Pro Leu Pro Gly
1               5                   10

<210> SEQ ID NO 266
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 266

Xaa Trp Leu Arg Arg Ala Tyr Ala Pro Leu Pro Asp
1               5                   10

<210> SEQ ID NO 267
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 267

Xaa Trp Leu Arg Arg Ala Tyr Ala Pro Leu Pro Gly Leu
1               5                   10

<210> SEQ ID NO 268
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 268

Xaa Trp Leu Arg Arg Ala Tyr Ala Pro Leu Pro Gly Lys
1               5                   10

<210> SEQ ID NO 269
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 269

Xaa Trp Leu Arg Arg Ala Tyr Ala Pro Leu Pro Asp Leu
1               5                   10
```

```
<210> SEQ ID NO 270
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 270

Xaa Trp Leu Arg Arg Ala Tyr Ala Pro Leu Pro Asp Lys
1               5                   10

<210> SEQ ID NO 271
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 271

Xaa Trp Leu Arg Arg Ala Tyr Ala Pro Leu Pro Gly Leu Ser
1               5                   10

<210> SEQ ID NO 272
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 272

Xaa Trp Leu Arg Arg Ala Tyr Ala Pro Leu Pro Gly Leu Thr
1               5                   10

<210> SEQ ID NO 273
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 273

Xaa Trp Leu Arg Arg Ala Tyr Ala Pro Leu Pro Gly Lys Ser
1               5                   10

<210> SEQ ID NO 274
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W
```

```
<400> SEQUENCE: 274

Xaa Trp Leu Arg Arg Ala Tyr Ala Pro Leu Pro Gly Lys Thr
 1               5                  10

<210> SEQ ID NO 275
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 275

Xaa Trp Leu Arg Arg Ala Tyr Ala Pro Leu Pro Asp Leu Ser
 1               5                  10

<210> SEQ ID NO 276
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 276

Xaa Trp Leu Arg Arg Ala Tyr Ala Pro Leu Pro Asp Leu Thr
 1               5                  10

<210> SEQ ID NO 277
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 277

Xaa Trp Leu Arg Arg Ala Tyr Ala Pro Leu Pro Asp Lys Ser
 1               5                  10

<210> SEQ ID NO 278
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F, Y, or W

<400> SEQUENCE: 278

Xaa Trp Leu Arg Arg Ala Tyr Ala Pro Leu Pro Asp Lys Thr
 1               5                  10

<210> SEQ ID NO 279
<211> LENGTH: 1
<212> TYPE: PRT
<213> ORGANISM: Artificial sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: X is (R)4-9

<400> SEQUENCE: 279

Xaa
1

<210> SEQ ID NO 280
<211> LENGTH: 13
<212> TYPE: PRT
<213> ORGANISM: Artificial sequence
<220> FEATURE:
<223> OTHER INFORMATION: Synthetic peptide

<400> SEQUENCE: 280

Gly Arg Lys Lys Arg Arg Gln Arg Arg Arg Pro Pro Gln
1               5                   10

<210> SEQ ID NO 281
<211> LENGTH: 12
<212> TYPE: PRT
<213> ORGANISM: Artificial sequence
<220> FEATURE:
<223> OTHER INFORMATION: Synthetic peptide

<400> SEQUENCE: 281

Ala Tyr Ala Arg Ala Ala Ala Arg Gln Ala Arg Ala
1               5                   10

<210> SEQ ID NO 282
<211> LENGTH: 34
<212> TYPE: PRT
<213> ORGANISM: Artificial sequence
<220> FEATURE:
<223> OTHER INFORMATION: Synthetic peptide

<400> SEQUENCE: 282

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 283
<211> LENGTH: 27
<212> TYPE: PRT
<213> ORGANISM: Artificial sequence
<220> FEATURE:
<223> OTHER INFORMATION: Synthetic peptide

<400> SEQUENCE: 283

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 284
<211> LENGTH: 12
<212> TYPE: PRT
<213> ORGANISM: Artificial sequence
<220> FEATURE:
<223> OTHER INFORMATION: Synthetic peptide
```

-continued

```
<400> SEQUENCE: 284

Pro Leu Ser Ser Ile Phe Ser Arg Ile Gly Asp Pro
1               5                   10

<210> SEQ ID NO 285
<211> LENGTH: 16
<212> TYPE: PRT
<213> ORGANISM: Artificial sequence
<220> FEATURE:
<223> OTHER INFORMATION: Synthetic peptide

<400> SEQUENCE: 285

Ala Ala Val Ala Leu Leu Pro Ala Val Leu Leu Ala Leu Leu Ala Pro
1               5                   10                  15

<210> SEQ ID NO 286
<211> LENGTH: 12
<212> TYPE: PRT
<213> ORGANISM: Artificial sequence
<220> FEATURE:
<223> OTHER INFORMATION: Synthetic peptide

<400> SEQUENCE: 286

Ala Ala Val Leu Leu Pro Val Leu Leu Ala Ala Pro
1               5                   10

<210> SEQ ID NO 287
<211> LENGTH: 15
<212> TYPE: PRT
<213> ORGANISM: Artificial sequence
<220> FEATURE:
<223> OTHER INFORMATION: Synthetic peptide

<400> SEQUENCE: 287

Val Thr Val Leu Ala Leu Gly Ala Leu Ala Gly Val Gly Val Gly
1               5                   10                  15

<210> SEQ ID NO 288
<211> LENGTH: 21
<212> TYPE: PRT
<213> ORGANISM: Artificial sequence
<220> FEATURE:
<223> OTHER INFORMATION: Synthetic peptide

<400> SEQUENCE: 288

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 289
<211> LENGTH: 27
<212> TYPE: PRT
<213> ORGANISM: Artificial sequence
<220> FEATURE:
<223> OTHER INFORMATION: Synthetic peptide

<400> SEQUENCE: 289

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 290
<211> LENGTH: 18
```

```
<212> TYPE: PRT
<213> ORGANISM: Artificial sequence
<220> FEATURE:
<223> OTHER INFORMATION: Synthetic peptide

<400> SEQUENCE: 290

Lys Leu Ala Leu Lys Leu Ala Leu Lys Ala Leu Lys Ala Ala Leu Lys
1               5                   10                  15

Leu Ala

<210> SEQ ID NO 291
<211> LENGTH: 21
<212> TYPE: PRT
<213> ORGANISM: Artificial sequence
<220> FEATURE:
<223> OTHER INFORMATION: Synthetic peptide

<400> SEQUENCE: 291

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 292
<211> LENGTH: 16
<212> TYPE: PRT
<213> ORGANISM: Artificial sequence
<220> FEATURE:
<223> OTHER INFORMATION: Synthetic peptide

<400> SEQUENCE: 292

Lys Ala Phe Ala Lys Leu Ala Ala Arg Leu Tyr Arg Lys Ala Gly Cys
1               5                   10                  15

<210> SEQ ID NO 293
<211> LENGTH: 16
<212> TYPE: PRT
<213> ORGANISM: Artificial sequence
<220> FEATURE:
<223> OTHER INFORMATION: Synthetic peptide

<400> SEQUENCE: 293

Lys Ala Phe Ala Lys Leu Ala Ala Arg Leu Tyr Arg Ala Ala Gly Cys
1               5                   10                  15

<210> SEQ ID NO 294
<211> LENGTH: 16
<212> TYPE: PRT
<213> ORGANISM: Artificial sequence
<220> FEATURE:
<223> OTHER INFORMATION: Synthetic peptide

<400> SEQUENCE: 294

Ala Ala Phe Ala Lys Leu Ala Ala Arg Leu Tyr Arg Lys Ala Gly Cys
1               5                   10                  15

<210> SEQ ID NO 295
<211> LENGTH: 16
<212> TYPE: PRT
<213> ORGANISM: Artificial sequence
<220> FEATURE:
<223> OTHER INFORMATION: Synthetic peptide

<400> SEQUENCE: 295

Lys Ala Phe Ala Ala Leu Ala Ala Arg Leu Tyr Arg Lys Ala Gly Cys
1               5                   10                  15
```

<210> SEQ ID NO 296
<211> LENGTH: 16
<212> TYPE: PRT
<213> ORGANISM: Artificial sequence
<220> FEATURE:
<223> OTHER INFORMATION: Synthetic peptide

<400> SEQUENCE: 296

Lys Ala Phe Ala Lys Leu Ala Ala Gln Leu Tyr Arg Lys Ala Gly Cys
1               5                   10                  15

<210> SEQ ID NO 297
<211> LENGTH: 160
<212> TYPE: PRT
<213> ORGANISM: Artificial sequence
<220> FEATURE:
<223> OTHER INFORMATION: Synthetic peptide

<400> SEQUENCE: 297

Met Glu Ile Pro Val Pro Val Gln Pro Ser Trp Leu Arg Arg Ala Ser
1               5                   10                  15

Ala Pro Leu Pro Gly Leu Ser Ala Pro Gly Arg Leu Phe Asp Gln Arg
            20                  25                  30

Phe Gly Glu Gly Leu Leu Glu Ala Glu Leu Ala Ala Leu Cys Pro Thr
        35                  40                  45

Thr Leu Ala Pro Tyr Tyr Leu Arg Ala Pro Ser Val Ala Leu Pro Val
    50                  55                  60

Ala Gln Val Pro Thr Asp Pro Gly His Phe Ser Val Leu Leu Asp Val
65                  70                  75                  80

Lys His Phe Ser Pro Glu Glu Ile Ala Val Lys Val Val Gly Glu His
                85                  90                  95

Val Glu Val His Ala Arg His Glu Glu Arg Pro Asp Glu His Gly Phe
            100                 105                 110

Val Ala Arg Glu Phe His Arg Arg Tyr Arg Leu Pro Pro Gly Val Asp
        115                 120                 125

Pro Ala Ala Val Thr Ser Ala Leu Ser Pro Glu Gly Val Leu Ser Ile
    130                 135                 140

Gln Ala Ala Pro Ala Ser Ala Gln Ala Pro Pro Ala Ala Ala Lys
145                 150                 155                 160

<210> SEQ ID NO 298
<211> LENGTH: 160
<212> TYPE: PRT
<213> ORGANISM: Artificial sequence
<220> FEATURE:
<223> OTHER INFORMATION: Synthetic peptide

<400> SEQUENCE: 298

Met Glu Ile Pro Val Pro Val Gln Pro Ser Trp Leu Arg Arg Ala Asp
1               5                   10                  15

Ala Pro Leu Pro Gly Leu Ser Ala Pro Gly Arg Leu Phe Asp Gln Arg
            20                  25                  30

Phe Gly Glu Gly Leu Leu Glu Ala Glu Leu Ala Ala Leu Cys Pro Thr
        35                  40                  45

Thr Leu Ala Pro Tyr Tyr Leu Arg Ala Pro Ser Val Ala Leu Pro Val
    50                  55                  60

Ala Gln Val Pro Thr Asp Pro Gly His Phe Ser Val Leu Leu Asp Val
65                  70                  75                  80

```
Lys His Phe Ser Pro Glu Glu Ile Ala Val Lys Val Val Gly Glu His
                85                  90                  95

Val Glu Val His Ala Arg His Glu Glu Arg Pro Asp Glu His Gly Phe
            100                 105                 110

Val Ala Arg Glu Phe His Arg Arg Tyr Arg Leu Pro Pro Gly Val Asp
        115                 120                 125

Pro Ala Ala Val Thr Ser Ala Leu Ser Pro Glu Gly Val Leu Ser Ile
    130                 135                 140

Gln Ala Ala Pro Ala Ser Ala Gln Ala Pro Pro Ala Ala Lys
145                 150                 155                 160

<210> SEQ ID NO 299
<211> LENGTH: 160
<212> TYPE: PRT
<213> ORGANISM: Artificial sequence
<220> FEATURE:
<223> OTHER INFORMATION: Synthetic peptide

<400> SEQUENCE: 299

Met Glu Ile Pro Val Pro Val Gln Pro Ser Trp Leu Arg Arg Ala Glu
1               5                   10                  15

Ala Pro Leu Pro Gly Leu Ser Ala Pro Gly Arg Leu Phe Asp Gln Arg
            20                  25                  30

Phe Gly Glu Gly Leu Leu Glu Ala Glu Leu Ala Ala Leu Cys Pro Thr
        35                  40                  45

Thr Leu Ala Pro Tyr Tyr Leu Arg Ala Pro Ser Val Ala Leu Pro Val
    50                  55                  60

Ala Gln Val Pro Thr Asp Pro Gly His Phe Ser Val Leu Leu Asp Val
65                  70                  75                  80

Lys His Phe Ser Pro Glu Glu Ile Ala Val Lys Val Val Gly Glu His
                85                  90                  95

Val Glu Val His Ala Arg His Glu Glu Arg Pro Asp Glu His Gly Phe
            100                 105                 110

Val Ala Arg Glu Phe His Arg Arg Tyr Arg Leu Pro Pro Gly Val Asp
        115                 120                 125

Pro Ala Ala Val Thr Ser Ala Leu Ser Pro Glu Gly Val Leu Ser Ile
    130                 135                 140

Gln Ala Ala Pro Ala Ser Ala Gln Ala Pro Pro Ala Ala Lys
145                 150                 155                 160

<210> SEQ ID NO 300
<211> LENGTH: 13
<212> TYPE: PRT
<213> ORGANISM: Artificial sequence
<220> FEATURE:
<223> OTHER INFORMATION: Synthetic peptide

<400> SEQUENCE: 300

Trp Leu Arg Arg Ala Ser Ala Pro Leu Pro Gly Leu Lys
1               5                   10

<210> SEQ ID NO 301
<211> LENGTH: 13
<212> TYPE: PRT
<213> ORGANISM: Artificial sequence
<220> FEATURE:
<223> OTHER INFORMATION: Synthetic peptide

<400> SEQUENCE: 301

Trp Leu Arg Arg Ala Asp Ala Pro Leu Pro Gly Leu Lys
```

-continued

<210> SEQ ID NO 302
<211> LENGTH: 13
<212> TYPE: PRT
<213> ORGANISM: Artificial sequence
<220> FEATURE:
<223> OTHER INFORMATION: Synthetic peptide

<400> SEQUENCE: 302

Trp Leu Arg Arg Ala Glu Ala Pro Leu Pro Gly Leu Lys
 1               5                  10

<210> SEQ ID NO 303
<211> LENGTH: 486
<212> TYPE: DNA
<213> ORGANISM: Artificial sequence
<220> FEATURE:
<223> OTHER INFORMATION: Sequence encoding rat HSP20

<400> SEQUENCE: 303
atggagatac gcgtgccggt acaacccagc tggctgcggc gtgcttccgc gccattacct      60
ggcttcagta cccccggacg attgtttgac cagaggtttg gggaaggttt acttgaggcg     120
gaattagcaa gtctatgtcc tgcagctata gcaccctact acctaagggc accatctgtc     180
gcgctcccaa ctgcccaagt gcccacggat ccaggctatt tcagcgttct gttagacgta     240
aagcatttta gtccagaaga aatttcagta aaagtagtgg agaccatgt cgaggtacat      300 gctagacacg aagagagacc tgatgaacac ggtttcatcg ctcgagagtt tcaccggcgt     360
tatcgcttgc cgccgggggt tgatcccgcg gccgtcacat cagcactcag tccggaggga     420
gttttatcca tacaagccac accggcctct gctcaggcct cgcttccatc gcctcctgcg     480
gcaaaa                                                                486

<210> SEQ ID NO 304
<211> LENGTH: 29
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (22)..(22)
<223> OTHER INFORMATION: S is phosphorylated

<400> SEQUENCE: 304

Ala Gly Gly Gly Gly Tyr Gly Arg Lys Lys Arg Arg Gln Arg Arg Arg
 1               5                  10                  15

Trp Leu Arg Arg Ala Ser Ala Pro Leu Pro Gly Leu Lys
            20                  25

<210> SEQ ID NO 305
<211> LENGTH: 29
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (20)..(20)
<223> OTHER INFORMATION: S is phosphorylated

<400> SEQUENCE: 305

Ala Gly Gly Gly Gly Tyr Gly Arg Lys Lys Arg Arg Gln Arg Arg Arg
 1               5                  10                  15

Pro Arg Lys Ser Leu Trp Ala Leu Gly Arg Pro Leu Ala
            20                  25

<210> SEQ ID NO 306
<211> LENGTH: 16
<212> TYPE: PRT
<213> ORGANISM: Artificial sequence
<220> FEATURE:
<223> OTHER INFORMATION: Synthetic peptide

<400> SEQUENCE: 306

Ala Gly Gly Gly Gly Tyr Gly Arg Lys Lys Arg Arg Gln Arg Arg Arg
1               5                   10                  15

<210> SEQ ID NO 307
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (19)..(19)
<223> OTHER INFORMATION: S is phosphorylated

<400> SEQUENCE: 307

Ala Tyr Ala Arg Arg Ala Ala Ala Arg Gln Ala Arg Ala Trp Leu Arg
1               5                   10                  15

Arg Ala Ser Ala Pro Leu Pro Gly Leu Lys
            20                  25

<210> SEQ ID NO 308
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (17)..(17)
<223> OTHER INFORMATION: S is phosphorylated

<400> SEQUENCE: 308

Ala Tyr Ala Arg Arg Ala Ala Ala Arg Gln Ala Arg Ala Pro Arg Lys
1               5                   10                  15

Ser Leu Trp Ala Leu Gly Arg Pro Leu Ala
            20                  25

<210> SEQ ID NO 309
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: S is phosphorylated

<400> SEQUENCE: 309

Arg Arg Arg Arg Arg Arg Ala Ser Ala Pro Leu Pro
1               5                   10

<210> SEQ ID NO 310
<211> LENGTH: 14
<212> TYPE: PRT
<213> ORGANISM: Artificial sequence

```
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: S is phosphorylated

<400> SEQUENCE: 310

Arg Arg Arg Arg Trp Leu Arg Arg Ala Ser Ala Pro Leu Pro
1               5                   10

<210> SEQ ID NO 311
<211> LENGTH: 3
<212> TYPE: PRT
<213> ORGANISM: Artificial sequence
<220> FEATURE:
<223> OTHER INFORMATION: Synthetic peptide

<400> SEQUENCE: 311

Leu Arg Arg
1

<210> SEQ ID NO 312
<211> LENGTH: 3
<212> TYPE: PRT
<213> ORGANISM: Artificial sequence
<220> FEATURE:
<223> OTHER INFORMATION: Synthetic peptide

<400> SEQUENCE: 312

Gly Leu Ser
1

<210> SEQ ID NO 313
<211> LENGTH: 3
<212> TYPE: PRT
<213> ORGANISM: Artificial sequence
<220> FEATURE:
<223> OTHER INFORMATION: Synthetic peptide

<400> SEQUENCE: 313

Gly Leu Thr
1

<210> SEQ ID NO 314
<211> LENGTH: 3
<212> TYPE: PRT
<213> ORGANISM: Artificial sequence
<220> FEATURE:
<223> OTHER INFORMATION: Synthetic peptide

<400> SEQUENCE: 314

Gly Lys Ser
1

<210> SEQ ID NO 315
<211> LENGTH: 3
<212> TYPE: PRT
<213> ORGANISM: Artificial sequence
<220> FEATURE:
<223> OTHER INFORMATION: Synthetic peptide

<400> SEQUENCE: 315

Gly Lys Thr
1

<210> SEQ ID NO 316
```

```
<211> LENGTH: 3
<212> TYPE: PRT
<213> ORGANISM: Artificial sequence
<220> FEATURE:
<223> OTHER INFORMATION: Synthetic peptide

<400> SEQUENCE: 316

Asp Leu Ser
1

<210> SEQ ID NO 317
<211> LENGTH: 3
<212> TYPE: PRT
<213> ORGANISM: Artificial sequence
<220> FEATURE:
<223> OTHER INFORMATION: Synthetic peptide

<400> SEQUENCE: 317

Asp Leu Thr
1

<210> SEQ ID NO 318
<211> LENGTH: 3
<212> TYPE: PRT
<213> ORGANISM: Artificial sequence
<220> FEATURE:
<223> OTHER INFORMATION: Synthetic peptide

<400> SEQUENCE: 318

Asp Lys Ser
1

<210> SEQ ID NO 319
<211> LENGTH: 3
<212> TYPE: PRT
<213> ORGANISM: Artificial sequence
<220> FEATURE:
<223> OTHER INFORMATION: Synthetic peptide

<400> SEQUENCE: 319

Asp Lys Thr
1

<210> SEQ ID NO 320
<211> LENGTH: 480
<212> TYPE: DNA
<213> ORGANISM: Artificial sequence
<220> FEATURE:
<223> OTHER INFORMATION: Sequence encoding human HSP20

<400> SEQUENCE: 320
atggaaattc ccgttccagt ccagcctagt tggctaagaa gagctagtgc gcctttgccg      60
ggtttgagtg cccccgggag gctatttgat caacgctttg gcgaggggtt actggaggct     120
gaattagcag cactttgtcc gaccacactc gcgccctatt accttagagc gccgtctgta     180
gccttaccag tcgctcaggt accaactgac ccaggccact tctccgtttt attagacgtg     240
aaacacttta gcccagaaga gatagcagtc aaagttgtag agagcatgt ggaagttcac      300 gcgagacatg aagagagacc agatgaacat ggtttcgtag cgagagaatt ccatcgacgg     360
tatcgtctgc cccaggagt cgatcctgca gctgtgacga gtgcattatc gcctgaggga      420
gtgctcagta tccaagcagc ccccgcgtca gcccaagccc cgcctccggc tgctgccaag     480
```